United States Patent [19]
Cournoyer et al.

[11] Patent Number: 5,952,362
[45] Date of Patent: Sep. 14, 1999

[54] 2-IMIDAZOLINE, 2-OXAZOLINE, 2-THIAZOLINE, AND 4-IMIDAZOLE DERIVATIVES OF METHYLPHENYL, METHOXYPHENYL, AND AMINOPHENYL ALKYLSULFONAMIDES AND UREAS AND THEIR USE

[75] Inventors: Richard Leo Cournoyer, San Francisco; Paul Francis Keitz, Redwood City; Counde O'Yang, Sunnyvale; Dennis Mitsugu Yasuda, Campbell, all of Calif.

[73] Assignee: Syntex (U.S.A) Inc., Palo Alto, Calif.

[21] Appl. No.: 09/089,779

[22] Filed: Jun. 3, 1998

Related U.S. Application Data

[60] Provisional application No. 60/075,978, Feb. 25, 1998, and provisional application No. 60/050,479, Jun. 23, 1997.

[51] Int. Cl.⁶ .................... A61K 31/415; C07D 233/64
[52] U.S. Cl. .................. 514/398; 514/399; 514/400; 548/339.5; 548/340.1; 548/341.1; 548/341.5; 548/342.1
[58] Field of Search .................... 514/398, 399, 514/400; 548/339.5, 340.1, 341.1, 341.5, 342.1

[56] References Cited

U.S. PATENT DOCUMENTS

| | | |
|---|---|---|
| 2,663,732 | 12/1953 | Weissberger et al. |
| 3,340,298 | 9/1967 | Wismayr et al. |
| 4,238,497 | 12/1980 | Black et al. |
| 4,343,808 | 8/1982 | Broersma, Jr. et al. |
| 4,414,223 | 11/1983 | Copp et al. |
| 4,492,709 | 1/1985 | Purcell |
| 4,665,085 | 5/1987 | Coquelet et al. |
| 4,665,095 | 5/1987 | Winn et al. |
| 4,956,388 | 9/1990 | Robertson et al. |
| 5,360,822 | 11/1994 | Morino et al. |

(List continued on next page.)

FOREIGN PATENT DOCUMENTS

| | | |
|---|---|---|
| 862022 | 6/1978 | Belgium . |
| 0086126 | 7/1985 | European Pat. Off. . |
| 0132190 | 1/1988 | European Pat. Off. . |
| 0535923 | 4/1993 | European Pat. Off. . |
| 135 016C | 10/1902 | Germany . |
| 1151331 | 7/1963 | Germany . |
| 2756638 | 6/1978 | Germany . |
| 3518604 | 11/1985 | Germany . |
| 19514579 | 10/1996 | Germany . |
| 236117 | 9/1992 | New Zealand . |
| 2160198 | 12/1985 | United Kingdom . |
| WO 93/16069 | 8/1993 | WIPO . |
| WO 94/08040 | 4/1994 | WIPO . |
| WO 96/04270 | 2/1996 | WIPO . |
| WO 96/17612 | 6/1996 | WIPO . |
| WO96/32939 | 10/1996 | WIPO . |
| WO 96/38143 | 12/1996 | WIPO . |
| WO 97/31636 | 9/1997 | WIPO . |
| WO 97/42956 | 11/1997 | WIPO . |

OTHER PUBLICATIONS

Morgan G.T. and Micklethwait F.M.G., Journal of the Chemical Society, vol. 89, 1906 pp. 1289–1300 "The Action of Nitrous Acid on the Aryl–sulphonylmetadiamines".

Blazak Z. Chem. Listy, vol. 42, No. 121, 1948, pp. 155–161, "Meziprodukty pro vyrobu barviv".

Brown S.M. et al, Journal of the Chemical Society No. 1, 1950, p. 1019, "p–Cymene–2–sulphonamides".

G.J. Atwell et al, Journal of Medicinal Chemistry, vol. 15, No. 6, Jun. 1972, pp. 611–615, "Potential Antitumor Agents. 12. 9–Anilinoacridines".

Hall C.M. et al, Journal of Medicinal Chemistry, vol. 17, No. 7, Jul. 1974, pp. 685–690, "Quinoline Derivatives as Anti-allergy Agents".

(List continued on next page.)

*Primary Examiner*—Johann Richter
*Assistant Examiner*—Ebenezer Sackey
*Attorney, Agent, or Firm*—Janet Pauline Clark; Janet K. Kaku

[57] ABSTRACT

The present invention concerns novel compounds represented by the Formula:

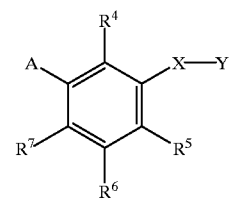

wherein: A is $R^1_q(R^3R^{60}N)_m(Z)(NR^2)_n$; m and q are each 0 or 1, with the proviso that when q is 1, m is 0 and when q is 0, m is 1; Z is C=O or $SO_2$; n is 1 with the proviso that, when Z is C=O, m is 1; X is —NH—, —$CH_2$—, or —$OCH_2$—; Y is 2-imidazoline, 2-oxazoline, 2-thiazoline, or 4-imidazole; $R^1$ is H, lower alkyl, or phenyl, with the proviso that, when $R^1$ is H, m is 1; $R^2$, $R^3$, $R^{60}$ are each independently H, lower alkyl, or phenyl; $R^4$, $R^5$, $R^6$, and $R^7$ are each independently hydrogen, lower alkyl, —$CF_3$, lower alkoxy, halogen, phenyl, lower alkeny, hydroxyl, lower alkylsulfonamido, or lower cycloalkyl, wherein $R^2$ and $R^7$ optionally may be taken together to form alkylene or alkenylene of 2 to 3 atoms in an unsubstituted or optionally substituted 5- or 6-membered ring, wherein the optional substituents on the ring are halo, lower alkyl, or —CN, with the proviso that, when $R^7$ is hydroxyl or lower alkylsulfonamido, then X is not —NH— when Y is 2-imidazoline. The compounds include pharmaceutically acceptable salts of the above. In the above formula A may be, for example, ($R^1SO_2NR^2$—), ($R^3R^{60}NSO_2NR^2$—), or ($R^3R^{60}NCONR^2$—). The invention also includes the use of the above compounds, and compositions containing them, as $alpha_{1A/1L}$ agonists in the treatment of various disease states such as urinary incontinence, nasal congestion, priapism, depression, anxiety, dementia, senility, Alzheimer's, deficiencies in attentiveness and cognition, and eating disorders such as obesity, bulimia, and anorexia.

85 Claims, No Drawings

U.S. PATENT DOCUMENTS

| | | |
|---|---|---|
| 5,403,847 | 4/1995 | Gluchowski et al. . |
| 5,541,210 | 7/1996 | Cupps et al. . |
| 5,556,753 | 9/1996 | Bard et al. . |
| 5,578,611 | 11/1996 | Gluchowski et al. . |
| 5,578,616 | 11/1996 | Aslanian et al. . |
| 5,597,823 | 1/1997 | Meyer et al. . |
| 5,610,174 | 3/1997 | Craig et al. . |
| 5,716,966 | 2/1998 | Cupps et al. . |

OTHER PUBLICATIONS

Denny W.A. et al, Journal of Medicinal Chemistry, vol. 25, No. 3, Mar. 1982, pp. 276–315, Potential Antitumor Agents. 26. Quantitative Relationships between Experimental Antitumor Activity, Toxicity, and Structure for the General Class of 9–Anilinoacridine Antitumor Agents.

Mekelburger H.–B. et al, Chemische Berichte, vol. 126, No. 5, 1993, pp. 1161–1169, "Repetitive Synthesis of Bulky Dendrimers—A Reversibly Photoactive Dendrimer with Six Azobenzene Side Chains".

Takeuchi Y. et al, Chemical & Pharmaceutical Bulletin, vol. 45, No. 2, Feb. 1997, pp. 406–411, "Synthesis and Antitumor Activity of Fused Quinoline Derivatives. IV. Novel 11–Aminoiindolo[3,2–b]quinolines".

Blade Pique J., Chemical Abstracts, vol. 67, No. 9, Aug. 28, 1967, No. 43813t, p. 4122, "Imidazole Derivatives".

Chemical Abstracts, vol. 69., No. 13, Sep. 23, 1968, No. 52140q, p. 4873, "6–tert–Butyl–3–(2–imidazolin–2–ylmethyl)–2,4–dimethyl–aniline".

Gh. Botez et al., *Chemical Abstract* 6834 (1964) (Abstract Only).

Wein, *Urologic Clinics of North America* (1995) 22:557–577.

Lundberg (editor), *JAMA* (1989) 261 (18):2685–2690.

Andersson and Sjögren, *Progress in Neurobiology* (1982) 19:71–89.

Sourander, *Gerontology* (1990) 36:19–26.

Hieble, et al., *Pharmacol. Revs.* (1995) 47:267–270.

Schwinn, et al., *J. Biol. Chem.* (1990) 265:8183–8189.

Ford, et al., *Trends Pharmacol. Sci.* (1994) 15:167–170.

Flavahan and Vanhoutte, *Trends Pharmacol. Sci.* (1986) 7:347–349.

Muramatsu, et al., *Br. J. Pharmacol.* (1990) 99:197–201.

Ford, et al., *Mol. Pharmacol.* (1996) 49;209–215.

Ford, et al., *Br. J. Pharmacol.* (1997) 121:1127–1135.

Forray, et al., Mol. Pharmacol. (1994) 45:703–708.

Latifpour, et al., *J.Pharmacol Exp. Ther.* (1990) 253:661–667.

Tsujimoto, et al., *J. Pharmacol. Exp. Ther.* (1986) 236:384–389.

Yoshida, et al., *J. Pharmacol. Exp. Ther.* (1991) 257:1100–1108.

Chess–Williams, et al., *J. Auton. Pharmacol.* (1994) 14:375–381.

Proctor, *Am. Rev. Resp. Dis.* (1977) 115:97–129.

Proctor, et al., *Pharmac. Ther. B.* (1976) 2:493–509.

Scadding, *Clin. Exp. Allergy* (1995) 25:391–394.

Langer, *Biochem. Pharmacol.* (1974) 23:1793–1800.

Ichimura and Chow, *Arch Otorhinolaryngol* (1988) 245:127–131.

Andersson, et al., *Ann. Otol. Rhinol. Laryngol.* (1984) 93:179–182.

Ichimura and Jackson, Arch Otolaryngol (1984) 110:647–651.

Lung, et al., *J. Physiol.* (1984) 349:535–551.

Empey et al., *Drugs* (1981) 21:438–443.

Minneman, et al., *Mol. Pharmacol.* (1994) 46:929–936.

Berridge, et al., *Br. J. Pharmacol.* (1986) 88:345–354.

Gonzalez–Cabrera et al., *FASEB J.* (1998) 12(4):2585 (Abstract Only).

2-IMIDAZOLINE, 2-OXAZOLINE, 2-THIAZOLINE, AND 4-IMIDAZOLE DERIVATIVES OF METHYLPHENYL, METHOXYPHENYL, AND AMINOPHENYL ALKYLSULFONAMIDES AND UREAS AND THEIR USE

CROSS-REFERENCE TO RELATED APPLICATIONS

This application claims benefit under 35 U.S.C. 119(e) to U.S. Provisional Patent Applications Ser. No. 60/075,978, filed Feb. 25, 1998 and Ser. No. 60/050,479, filed Jun. 23, 1997.

BACKGROUND OF THE INVENTION

1. Field of the Invention

This invention relates to various 2-imidazoline, 2-oxazoline, 2-thiazoline, and 4-imidazole derivatives of methylphenyl, methoxyphenyl, and aminophenyl alkylsulfonamides and ureas, and their use in the treatment of various disease states, such as urinary incontinence, nasal congestion, priapism, depression, anxiety, dementia, senility, Alzheimer's, deficiencies in attentiveness and cognition, and eating disorders such as obesity, bulimia, and anorexia.

2. Urinary Incontinence

The lower urinary tract consists of the urinary bladder and urethra. Normal lower urinary tract function requires a coordinated relaxation of the bladder (detrusor muscle) and increase in urethral smooth muscle tone during bladder filling. The expulsion of urine (micturition), in contrast, requires a coordinated contraction of the detrusor and relaxation of urethral smooth muscle. This coordination is achieved by the integration of afferent (sensory) and efferent (parasympathetic, sympathetic, and somatic) nerve activity in both the central and peripheral nervous centers.

Incontinence is a condition characterized by the involuntary loss of urine, which is objectively demonstrable. It is both a social and hygienic problem. Stated simply, incontinence results from the failure of the bladder and/or the urethra to work properly, or when the coordination of their functions is defective. It is estimated that at least ten million Americans suffer from incontinence. While the prevalence of incontinence is two-fold higher in females, with the greatest incidence in postmenopausal women, it also affects males.

Urinary incontinence can be classified into four basic types.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Genuine stress incontinence (outlet incompetence) is the involuntary loss of urine occurring when increases in intra-abdominal pressure cause a rise in intravesical pressure which exceeds the resistance offered by urethral closure mechanisms. Stress incontinent episodes can result from normal activities such as laughing, coughing, sneezing, exercise, or, in severe stress incontinent patients, standing or walking. Physiologically, stress incontinence is often characterized by a descensus of the bladder neck and funneling of the bladder outlet. This type of incontinence is most common in multiparous women, as pregnancy and vaginal delivery can cause loss of the vesicourethral angle and damage to the external sphincter. Hormonal changes associated with menopause may exacerbate this condition.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or $alpha_1$-adrenoceptor antagonists), or psychiatric problems such as depression.

The treatment of incontinence depends upon the type and severity. Of the four types of incontinence, pharmacotherapy is most effective in the treatment of urge incontinence. A variety of pharmacological agents such as anticholinergics, smooth muscle relaxants, calcium channel antagonists, and beta-adrenoceptor agonists are used to decrease the contractility of the bladder. Some patients appear to benefit from estrogen (postmenopausal women) and $alpha_1$-adrenoceptor agonists. These agents, however, most likely act at the level of the urethra to increase closure pressure and prevent the loss of urine.

Mild to moderate stress incontinence can be treated both pharmacologically and by conservative approaches such as physiotherapy (Kegel exercises) and functional electrical stimulation, both of which aim to strengthen the periurethral musculature. Surgery is indicated in severe stress incontinent patients. Surgical techniques seek to improve the alignment of the bladder, urethra, and surrounding structures.

Only a limited number of pharmaceutical agents have been employed, with varying success, to treat stress incontinence. In postmenopausal women, estrogen replacement therapy is thought to improve continence by increasing urethral length and mucosal thickness, thereby increasing urethral closure pressure. Estrogen may also contribute to an increase in $alpha_1$-adrenoceptor expression in urethra (Wein, *Urologic Clinics of North America* (1995) 22:557–577). The efficacy of estrogen therapy is not universally accepted.

Phenylpropanolamine and psuedoephrine are considered first-line therapy for mild to moderate stress incontinence (Wein, supra; Lundberg (editor), *JAMA* (1989) 261(18):2685–2690). These agents are believed to work both by direct activation of $alpha_1$-adrenoceptors and indirectly by displacement of endogenous norepinephrine from sympathetic neurons following uptake into the nerve terminal (Andersson and Sjogren, *Progress in Neurobiology* (1982) 19:71–89). Activation of $alpha_1$-adrenoceptors located on the smooth muscle cells of the proximal urethra and bladder neck (Sourander, *Gerontology* (1990) 36:19–26; Wein, supra) evokes contraction and an increase in urethral closure pressure.

The utility of phenylpropanolamine and pseudoephrine is limited by a lack of selectivity among the $alpha_1$-adrenoceptor subtypes and by the indirect action of these agents (i.e. activation of $alpha_1$-, $alpha_2$-, and beta-adrenoceptors in the central nervous system and periphery).

As a result, any desired therapeutic effect of these agents may be accompanied by undesirable side effects such as an increase in blood pressure. The increase in blood pressure is dose-dependent and therefore limits the ability to achieve therapeutically effective circulating concentrations of these agents (Andersson and Sjogren, supra). Furthermore, in some patients these agents produce insomnia, anxiety, and dizziness as a result of their central nervous system stimulant actions (Andersson and Sjogren, supra; Wein, supra).

Midodrine is a sympathomimetic agent which has been evaluated for the treatment of stress incontinence. This $alpha_1$-adrenoceptor agonist is a prodrug which is converted in vivo to the active phenylethylamine, ST-1059. The clinical efficacy of midodrine has not been demonstrated conclusively (Andersson and Siogren, supra). Like the above compounds, its beneficial effects may be limited by cross-reactivity with other adrenoceptors which may limit the maximum achievable dose. A better understanding of $alpha_1$-adrenoceptor subtypes and their involvement in various physiological processes may facilitate the development of more efficacious drugs for the treatment of both stress and possibly urge incontinence.

$Alpha_1$-adrenoceptors are specific neuroreceptor proteins located in the peripheral and central nervous systems and on tissues throughout the body. The receptors are important switches for controlling many physiological functions and, thus, represent important targets for drug development. Drugs which interact at these receptors comprise two main classes: agonists, which mimic the endogenous ligands (norepinephrine and epinephrine) in their ability to activate the adrenoceptors; and antagonists, which serve to block the actions of the endogenous ligands.

During the past 15 years, a more precise understanding of alpha-adrenoceptors and drugs targeting alpha-adrenoceptors has emerged. Prior to 1977, only one alpha-adrenoceptor was known to exist. Between 1977 and 1986, it was accepted by the scientific community that at least two alpha-adrenoceptors, $alpha_1$- and $alpha_2$-, existed in the central and peripheral nervous systems. New techniques have led to the identification of distinct adrenoceptor proteins which are distributed throughout the central and peripheral nervous systems.

To date, three human $alpha_1$-adrenoceptors have been cloned ($alpha_{1A}$, $alpha_{1B}$, and $alpha_{1D}$), expressed, and characterized pharmacologically (Hieble, et al., *Pharmacol. Revs.* (1995) 47:267–270). The absence of an $alpha_{1C}$-adrenoceptor appellation is a consequence of the history of $alpha_1$-adrenoceptor subclassification. In 1990, an $alpha_1$-adrenoceptor was cloned and designated the $alpha_{1C}$-adrenoceptor, as the mRNA for this clone could not be detected in animal tissues known to express pharmacologically-defined $alpha_{1A}$-adrenoceptors (Schwinn, et al, *J. Biol. Chem.* (1990) 265:8183–8189). The $alpha_{1C}$-adrenoceptor was later equated with the $alpha_{1A}$-adrenoceptor, resulting in the discontinuation of the $alpha_{1C}$ designation (Ford, et al., *Trends Pharmacol. Sci.* (1994) 15:167–170).

A fourth subtype, the $alpha_{1L}$-adrenoceptor, has been described pharmacologically, but a distinct gene product has not been found (Flavahan and Vahnoutte, *Trends Pharmacol. Sci.* (1986) 7:347–349; Muramatsu, et al., *Br. J. Pharmacol.* (1990) 99:197–201). Despite a preponderance of $alpha_{1A}$-adrenoceptor mRNA in lower urinary tract tissues, it is the antagonist "fingerprint" of the pharmacologically-defined $alpha_{1L}$-adrenoceptor that correlates best with the $alpha_1$-adrenoceptor mediating contraction of lower urinary tract smooth muscle (Ford, et al., *Mol. Pharmacol.* (1996) 49:209–215). Recently, insights into this apparent discrepancy have been made while studying the functional responses in cells transfected with the cloned $alpha_{1A}$-adrenoceptor.

In contrast to radioligand binding studies which are traditionally conducted in hypotonic buffers at subphysiological temperatures, functional studies in transfected cells have been conducted in a physiological buffer at physiological temperature. Using these conditions, the pharmacology of key antagonists closely resembled that of the $alpha_{1L}$-adrenoceptor (Ford, et al., *Br. J. Pharmacol.* (1997) 121:1127–1135). Thus, it appears that the cloned $alpha_{1A}$-adrenoceptor can express two distinct pharmacologies ($alpha_{1A}$- and $alpha_{1L}$-), depending upon the experimental conditions employed. It should be noted that this phenomenon is specific for the $alpha_{1A}$-adrenoceptor subtype, as altering the experimental conditions in a similar fashion does not alter the pharmacology of cloned $alpha_{1B}$- or $alpha_{1D}$-adrenoceptors (Ford, et al.,1997, supra). Until this observation is confirmed and the nomenclature of $alpha_1$-adrenoceptors resolved, it would seem prudent to refer to ligands selective for the cloned $alpha_{1A}$-adrenoceptor as $alpha_{1A/1L}$ selective unless selectivity for the $alpha_{1A}$ or $alpha_{1L}$ states can be demonstrated.

The precise role of each of the $alpha_1$-adrenoceptor subtypes in various physiological responses is only beginning to be understood, but it is clear that individual subtypes do mediate distinct physiological responses to agonists and antagonists. For example, it has been shown that norepinephrine-induced contractions of the human prostate are mediated by the cloned $alpha_{1A}$-adrenoceptor (pharmacological $alpha_{1L}$-adrenoceptor; Forray, et al, *Mol. Pharmacol.* (1994) 45:703–708; Ford, et al., *Mol. Pharmacol.* (1996) 49:209–215).

The role of the sympathetic adrenergic nervous system in the storage function of the bladder is well recognized (Wein, supra; Latifpour, et al., *J. Pharmacol Exp. Ther.* (1990) 253:661–667). Likewise, it is understood in the art that the study of adrenoceptor mechanisms in isolated urethra and bladder tissues is applicable to incontinence therapy (Latifpour, et al., supra; Tsujimoto, et al., *J. Pharmacol. Exp. Ther.* (1986) 236:384–389). Various groups have attempted to identify, through radioligand binding and functional studies, the $alpha_1$-adrenoceptor subtype(s) in urethrae of humans, rabbits, and rats (Yoshida, et al., *J. Pharmacol. Exp. Ther.* (1991) 257:1100–1108; Testa, et al., supra; Chess-Williams, et al., *J. Auton. Pharmacol.* (1994) 14:375–381). These efforts have, thus far, failed to provide conclusive evidence for a particular $alpha_1$-adrenoceptor subtype being responsible for the effects of adrenoceptor agonists in the urethra. It is also known that some $alpha_{1A}$-adrenoceptor (formally $alpha_{1C}$) agonists may be useful for the treatment of urinary incontinence (Craig, et al., WO 96/38143).

Nasal Congestion

Approximately one-half of the resistance to airflow into the lung is provided by the nose and nasal cavity (Proctor, *Am. Rev. Resp. Dis.* (1977) 115:97–129). The nasal cavity is lined by a continuous mucus membrane which is highly vascularized. Nasal mucosa vascular beds consist of precapillary resistance vessels, venous sinusoids comprising both circular and longitudinal smooth muscle bundles which drain into postcapillary venules, and arteriovenous anastomoses which allow blood to bypass the capillary-sinusoid network (Proctor, et al., *Pharmac. Ther. B* (1976) 2:493–509; Scadding, *Clin. Exp. Allergy* (1995) 25:391–394). This anatomical arrangement makes the nasal mucosa, especially that lining the middle and inferior turbinates and septum, erectile tissue (Proctor, et al., 1976, supra). Engorgement of venous erectile tissue alters airway resistance and is important to the functioning of the nose as an air conditioner.

Both resistance and capacitance vessels in the nasal mucosa are richly innervated with autonomic fibers. It has been known for several decades that alpha-adrenoceptors mediate contraction of nasal mucosa (Proctor, et al., 1976, supra). Indeed this has formed the basis of treatment of nasal congestion with sympathomimetic drugs. Subsequent to the identification of distinct alpha-adrenoceptor subtypes (Langer, Biochem. Pharmacol. (1974) 23:1793–1800), the presence of postjunctional $alpha_1$- and $alpha_2$-adrenoceptors have been shown in nasal mucosa (Ichimura, et al., Arch Otorhinolaryngol (1988) 245:127–131; Andersson, et al., Ann. Otol. Rhinol. Laryngol. (1984) 93:179–182). The presence of prejunctional inhibitory $alpha_2$-adrenoceptors has also been shown (Ichimura, et al., Arch Otolaryngol (1984) 10:647–651.) Both $alpha_1$- and $alpha_2$-adrenoceptors are thought to mediate vasoconstriction of nasal mucosa capacitance vessels (venous sinusoids), whereas only $alpha_2$-adrenoceptors are thought to mediate vasoconstriction of resistance vessels (Andersson, et al., supra; Scadding, supra). It is believed that constriction of capacitance vessels reduces nasal congestion directly by increasing the tone of the venous sinusoids whereas constriction of resistance vessels results in an indirect decrease in nasal congestion by increasing arterial resistance and thereby decreased filling of the venous sinusoids (Lung, et al., J. Physiol. (1984) 349:535–551).

Intranasal sympathomimetic agents used to treat nasal congestion fall into two basic chemical classes, namely certain β-phenylethylamines and imidazolines (Empey, et al., Drugs (1981)21:438–443). The non-selective $alpha_1$-adrenoceptor agonist, phenylephrine (Minneman, et al., Mol. Pharmacol. (1994) 46:929–936), and the mixed $alpha_1$/$alpha_2$-adrenoceptor agonist, oxymetazoline (Minneman, et al., supra), are currently used respresentatives of these chemical classes, respectively.

The greatest concern with intranasal sympathomimetics is rhinitis medicamentosa, a syndrome of "rebound" congestion associated with frequent and prolonged use (more than 7 to 10 days). Rhinitis medicamentosa is not a problem with oral decongestants but there is a greater risk of systemic side effects (Empey, et al., supra). Despite the prevelance of this syndrome, the exact cause has not been elucidated. Possible explanations for "rebound" include the following. Prolonged or preferential constriction of the resistance vessels, possibly mediated by $alpha_2$-adrenoceptors, may deprive nasal mucosa of oxygen and nutritients thereby resulting in a reactive hyperemia which leads to the release of vasoactive mediators to counteract the vasoconstriction (Berridge, et al., Br. J. Pharmacol. (1986) 88:345–354; Scadding, supra). Prolonged exposure to high concentrations of highly efficacious adrenergic agents may also cause down regulation or desensitization of adrenergic receptors. That is, a decrease in the number or sensitivity of adrenergic receptors could reduce the responsiveness to both exogenous and endogenous sympathomimetics (Scadding, supra). Chemical irritation caused by the active ingredient or an ingredient in the formulation could also evoke rhinitis medicamentosa (Scadding, supra).

A lack of selectivity of currently used sympathomimetics for a specific adrenoceptor subtype raises the possibility that an effective intranasal decongestant could be developed which would not cause rhinitis medicamentosa. For example, several of the imidazoline agonists (e.g. oxymetazoline) possess agonits activity at both $alpha_1$- and $alpha_2$-adrenoceptors (Minneman, et al., supra). Thus, an agonist selective for $alpha_1$-adrenoceptors may not evoke vasoconstriction of nasal mucosa resistance vessels which may be involved in the pathogenesis of rhinitis medicamentosa (Scadding, supra). Similarly, phenylephrine does not discriminate between $alpha_1$-adrenoceptor subtypes (Minneman, et al., supra) which have subdivided into $alpha_{1A}$-, $alpha_{1B}$-, and $alpha_{1D}$-adrenoceptor subtypes in the last decade (Ford, et al., Trends Pharmacol. Sci. (1994) 15:167–170). Thus, it is possible that a single $alpha_1$-adrenoceptor subtype may selectively mediate vasoconstriction of nasal mucosa venous sinusoids and thus be devoid of adverse effects which could be mediated by other $alpha_1$-adrenoceptor subtypes.

Additional Previous Disclosures

Esser, et al., DE 195 14 579 A1 (published Oct. 24, 1996), disclose certain phenylimino-imidazolidine compounds, which are $alpha_{1L}$-agonists, for the treatment of urinary incontinence.

Craig, et al., WO 96/38143 (published Dec. 5, 1996), discuss the use of $alpha_{1C}$-selective adrenoceptor agonists for the treatment of urinary incontinence.

Purcell, U.S. Pat. No. 4,492,709 (issued Jan. 8, 1985), discloses 2-[4(3)-amino-3(4)-hydroxyphenylimino]-imidazoles useful in the treatment of gastric hypersecretion and hyperacidity. A similar disclosure appears in corresponding European application 0 086 126 B1 (published Jul. 24, 1985).

Coquelet, et al., U.S. Pat. No. 4,665,085 (issued May 12, 1987), discuss preparation process and therapeutical application of certain amidines. A similar disclosure is found in European patent application 0 132 190 B1 (published Jan. 13, 1988).

Pesticidal anilinomethylimidazolines are disclosed in Copp, et al., U.S. Pat. No. 4,414,223 (issued Nov. 8, 1983).

Certain imidazolines active as pesticides are discussed in by Copp, et al., Offenlegungsschrift 27 56 638 (published Jun. 22, 1978), and in corresponding Brevet D'Invention No. 862,022 (published Jun. 19, 1978).

Sulfonamides of phenoxyacetic acids and imidazoline derivatives from sulfonamido compounds of phenoxyacetic acid and of cresoxyacetic acids and their hypotensive activity are described by Gh. Botez, et al., in Chemical Abstract 6834 (1964).

Broersma, et al., U.S. Pat. No. 4,343,808 (issued Aug. 10, 1982), disclose the inhibition of sickling of sickle erythrocytes using certain phenoxy-, phenylthio- or anilino-imidazoline compounds.

Reiter, et al., U.K. Patent Application GB 2 160 198 A (published Dec. 18, 1985), discuss certain imidazolines.

Jones, et al., WO 96/17612 A1 (published Jun. 13, 1996), disclose treating cerebral or cardiac ischaemia or convulsions and also sickle cell anemia using new or known phenyl-guanidine or amidine derivatives.

Black, et al., U.S. Pat. No. 4,238,497 (issued Dec. 9, 1980), discloses imidazoline derivatives, salts thereof, and their use as pesticides.

The use of $alpha_{1A}$-selective adrenoceptor agonists for the treatment of urinary incontinence is discussed in Craig, et al., U.S. Pat. No. 5,610,174 (issued Mar. 11, 1997).

Prasit, et al., European patent application 0 535 923 A1 (published Apr. 7, 1993), discloses (azaarylmethoxy)indoles as inhibitors of leukotriene biosynthesis.

(Azaaromaticalkoxy)indoles as inhibitors of leukotriene biosynthesis are discussed in Frenette, WO 93/16069 (published Aug. 19, 1993).

Aslanian, et al., U.S. Pat. No. 5,578,616 (issued Nov. 26, 1996), disclose certain phenylalkylimidazoles having pharmacological properties, particularly CNS activities and activity against inflammatory disease.

Morino, et al., U.S. Pat. No. 5,360,822 (issued Nov. 1, 1994), disclose certain sufonanilide derivatives useful as remedies for urinary incontinence.

Wismayr, et al., U.S. Pat. No. 3,340,298 (issued Sep. 5, 1967), disclose certain phenylalkanolamine derivatives useful for treating hypertensive conditions.

Winn, et al., U.S. Pat. No. 4,665,095 (issued May 12, 1987), disclose certain imidazolines useful for treating nasal congestion.

Robertson, et al., U.S. Pat. No. 4,956,388 (issued Sep. 11, 1990), disclose certain 3-aryloxy-3-substituted propanamines capable of inhibiting the uptake of serotonin and norepinephrine.

Gluchowski, et al., U.S. Pat. Nos. 5,403,847 (issued Apr. 4, 1995) and 5,578,611 (issued Nov. 26, 1996), disclose certain $\alpha_{1C}$ specific compounds useful for treating benign prostatic hyperplasia.

Cupps, et al., U.S. Pat. No. 5,541,210 (issued Jul. 30, 1996), disclose certain benzimidazole compounds useful as $\alpha_2$ adrenoceptor agonists for treating respiratory, ocular, and/or gastrointestinal disorders.

Bard, et al., U.S. Pat. No. 5,556,753 (Sep. 17, 1996), disclose certain human $\alpha_1$ adrenegric receptors and uses thereof. See also WO 94/08040 (published Apr. 14, 1994).

Meyer, et al., U.S. Pat. No. 5,597,823 (issued Jan. 28, 1997), disclose certain tricyclic substituted hexahydrobenz (E)isoindone alpha-1 adrenergic antagonists useful for treating benign prostatic hyperplasia.

Jeon, et al., WO 97/31636 (published Sep. 4, 1997), disclose certain indole and benzothiazole derivatives which are selective for cloned human $\alpha_2$ receptors.

Wong, et al., WO 97/42956 (published Nov. 20, 1997), disclose certain dihydropyrimidine compounds which are selective antagonists for human $\alpha_1$ receptors.

Jeon, et al., WO 96/04270 (published Feb. 15, 1996), disclose certain benzimidazole derivatives selective for cloned human alpha 2 receptors and which are useful as analgesic, sedative, or anaesthetic agents.

SUMMARY OF THE INVENTION

The invention concerns novel compounds represented by Formula 1:

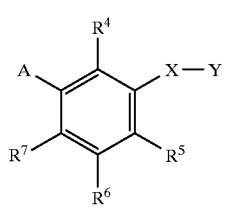

1 wherein: A is $R^1_q(R^3R^{60}N)_m(Z)(NR^2)_n$; m and q are each 0 or 1, with the proviso that when q is 1, m is 0 and when q is 0, m is 1; Z is C=O or $SO_2$; n is 1 with the proviso that, when Z is C=O, m is 1; X is —NH—, —CH$_2$—, or —OCH$_2$—; Y is 2-imidazoline, 2-oxazoline, 2-thiazoline, or 4-imidazole; $R^1$ is H, lower alkyl, or phenyl, with the proviso that, when $R^1$ is H, m is 1; $R^2$, $R^3$, and $R^{60}$ are each independently H, lower alkyl, or phenyl; $R^4$, $R^5$, $R^6$, and $R^7$ are each independently hydrogen, lower alkyl, —CF$_3$, lower alkoxy, halogen, phenyl, lower alkenyl, hydroxyl, lower alkylsulfonamido, or lower cycloalkyl, wherein $R^2$ and $R^7$ optionally may be taken together to form alkylene or alkenylene of 2 to 3 carbon atoms in an unsubstituted or optionally substituted 5- or 6-membered ring, wherein the optional substituents on the ring are halo, lower alkyl, or —CN, with the proviso that, when $R^7$ is hydroxyl or lower alkylsulfonamido, then X is not —NH— when Y is 2-imidazoline. The compounds include pharmaceutically acceptable salts of the above. In the above formula A may be, for example, ($R^1SO_2NR^2$—), ($R^3R^{60}NSO_2NR^2$—), or ($R^3R^{60}NCONR^2$—).

Preferred compounds of the present invention include compounds represented by Formula 2:

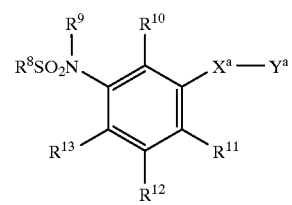

2 wherein: $X^a$ is —NH—, —CH$_2$—, or —OCH$_2$—; $Y^a$ is 2-imidazoline, 2-oxazoline, 2-thiazoline, or 4-imidazole; $R^8$ is lower alkyl, phenyl, or —NR$^{14}$R$^{15}$; $R^9$, $R^{14}$, and $R^{15}$ are each independently H or lower alkyl; $R^{10}$, $R^{11}$, $R^{12}$, and $R^{13}$ are each independently hydrogen, lower alkyl, —CF$_3$, lower alkoxy, halogen, phenyl, lower alkenyl, hydroxyl, lower alkylsulfonamido, or lower cycloalkyl, wherein $R^9$ and $R^{13}$ optionally may be taken together to form alkylene or alkenylene of 2 to 3 carbon atoms in a 5- or 6-membered ring, with the proviso that, when $R^{13}$ is hydroxyl or lower alkylsulfonamido, then X is not —NH— when Y is 2-imidazoline. The compounds include pharmaceutically acceptable salts of the above.

Preferred compounds of the present invention include compounds represented by Formula 3:

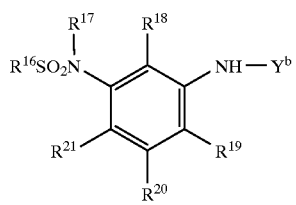

3 wherein: $Y^b$ is 2-imidazoline; $R^{16}$ is lower alkyl; $R^{17}$ is H or lower alkyl; $R^{18}$, $R^{19}$, $R^{20}$, and $R^{21}$ each independently hydrogen, lower alkyl, —CF$_3$, lower alkoxy, or halogen. The compounds include pharmaceutically acceptable salts of the above.

Preferred compounds of the present invention include compounds represented by Formula 4:

4

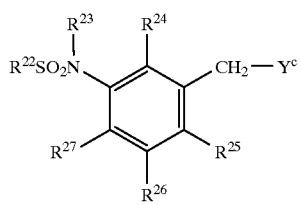

wherein: $Y^c$ is 2-imidazoline or 4-imidazole; $R^{22}$ is lower alkyl; $R^{23}$ is H or lower alkyl; $R^{24}$, $R^{25}$, $R^{26}$, and $R^{27}$ are each independently hydrogen, lower alkyl, lower alkoxy, halogen, phenyl, lower alkenyl, hydroxyl, or lower alkylsulfonamido. The compounds include pharmaceutically acceptable salts of the above.

Preferred compounds of the present invention include compounds represented by Formula 5:

5

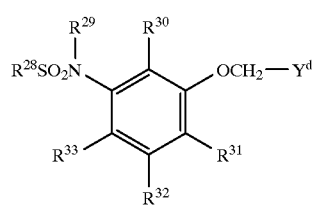

wherein: $Y^d$ is 2-imidazoline or 4-imidazole; $R^{28}$ is lower alkyl or phenyl; $R^{29}$ is H or lower alkyl; $R^{30}$, $R^{31}$, $R^{32}$, and $R^{33}$ are each independently hydrogen, lower alkyl, halogen, hydroxyl, or lower cycloalkyl. When $Y^d$ is 2-imidazoline and $R^{31}$ or $R^{32}$ are other than H, the invention includes a subset of compounds wherein $R^{30}$ or $R^{33}$ are other than H. The compounds include pharmaceutically acceptable salts of the above.

Preferred compounds of the present invention include compounds represented by Formula 6:

6

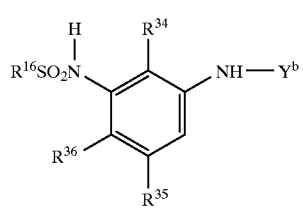

wherein: $Y^b$ is 2-imidazoline; $R^{16}$ is lower alkyl; $R^{34}$, $R^{35}$, and $R^{36}$ are each independently H, Cl, Br, F, or lower alkyl. The compounds include pharmaceutically acceptable salts of the above.

Preferred compounds of the present invention include compounds represented by Formula 7:

7

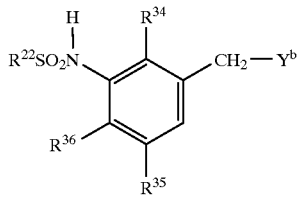

wherein: $Y^c$ is 2-imidazoline or 4-imidazole; $R^{22}$ is lower alkyl; $R^{34}$, $R^{35}$, and $R^{36}$ are each independently H, Cl, Br, F, or lower alkyl. The compounds include pharmaceutically acceptable salts of the above.

Preferred compounds of the present invention include compounds represented by Formula 8:

8

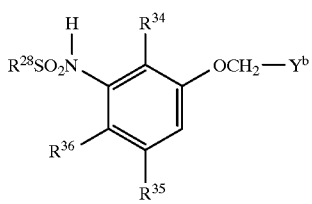

wherein: $Y^d$ is 2-imidazoline or 4-imidazole; $R^{28}$ is lower alkyl; $R^{34}$, $R^{35}$, and $R^{36}$ are each independently H, Cl, Br, F, or lower alkyl. The compounds include pharmaceutically acceptable salts of the above.

Preferred compounds of the present invention include compounds represented by Formula 76:

76

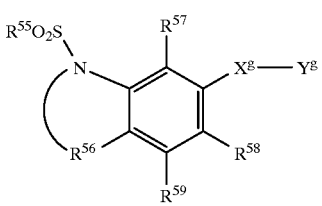

wherein: $X^g$ is —NH—, —CH$_2$—, or —OCH$_2$—; $Y^g$ is 2-imidazoline, 2-oxazoline, 2-thiazoline, or 4-imidazole; $R^{55}$ is lower alkyl or phenyl; $R^{56}$ forms part of an unsubstituted or optionally substituted 5- or 6-membered ring, wherein the optional substituents on the ring are halo, lower alkyl, or —CN and $R^{56}$ is (CH$_2$)$_k$ wherein k is 1 or 2, CH=CH, CH=CHCH$_2$, or CH$_2$CH=CH; $R^{57}$, $R^{58}$, and $R^{59}$ are each independently hydrogen, lower alkyl, —CF$_3$, lower alkoxy, halogen, phenyl, lower alkenyl, hydroxyl, lower alkylsulfonamido, or lower cycloalkyl. The compounds include pharmaceutically acceptable salts of the above.

Preferred compounds of the present invention include compounds represented by Formula 75:

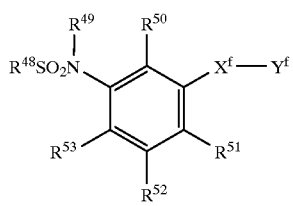

wherein: $X^f$ is —NH—, —CH$_2$—, or —OCH$_2$—; $Y^f$ is 2-oxazoline or 2-thiazoline; $R^{48}$ is lower alkyl; $R^{49}$ is H or lower alkyl; $R^{50}$, $R^{51}$, $R^{52}$, and $R^{53}$ are independently hydrogen, lower alkyl, —CF$_3$, lower alkoxy, halogen, phenyl, lower alkenyl, hydroxyl, lower alkylsulfonamido, or lower cycloalkyl, wherein $R^{49}$ and $R^{53}$ optionally may be taken together to form alkylene or alkenylene of 2 to 3 carbon atoms in a 5- or 6-membered ring. The compounds include pharmaceutically acceptable salts of the above.

Preferred compounds of the present invention include compounds represented by Formula 74:

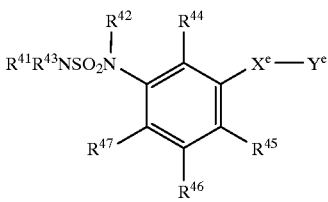

wherein: $X^e$ is —NH—, —CH$_2$—, or —OCH$_2$—; $Y^e$ is 2-imidazoline, 2-oxazoline, 2-thiazoline, or 4-imidazole; $R^{41}$, $R^{42}$, and $R^{43}$ are each independently H, phenyl, or lower alkyl; $R^{44}$, $R^{45}$, $R^{46}$, and $R^{47}$ are each independently hydrogen, lower alkyl, —CF$_3$, lower alkoxy, halogen, phenyl, lower alkenyl, hydroxyl, lower alkylsulfonamido, or lower cycloalkyl, wherein $R^{42}$ and $R^{47}$ optionally may be taken together to form alkylene or alkenylene of 2 to 3 carbon atoms in a 5- or 6-membered ring. The compounds include pharmaceutically acceptable salts of the above.

The present invention also includes compositions suitable for administration to a mammal, particularly a human, having a disease state that is alleviated by treatment with an alpha$_{1A/1L}$ adrenoceptor agonist, which composition comprises a therapeutically effective amount of a compound of the above formulae or a pharmaceutically acceptable salt thereof.

The present invention also concerns a method for treating a mammal, particularly a human, having a disease state that is alleviated by treatment with an alpha$_{1A/1L}$ adrenoceptor agonist, which comprises administering a therapeutically effective amount of a compound of the above formulae or a pharmaceutically acceptable salt thereof.

The present invention also includes a method for treating a mammal, particularly a human, having urinary incontinence, which comprises administering a therapeutically effective amount of a compound of the above formulae or a pharmaceutically acceptable salt thereof.

The present invention also includes a method for treating a mammal, particularly a human, having nasal congestion, which comprises administering a therapeutically effective amount of a compound of the above formulae or a pharmaceutically acceptable salt thereof.

The present invention also includes a method for treating a mammal, particularly a human, having priapism, depression, anxiety, dementia, senility, Alzheimer's, deficiencies in attentiveness and cognition, or eating disorders such as obesity, bulimia, and anorexia, which comprises administering a therapeutically effective amount of a compound of the above formulae or a pharmaceutically acceptable salt thereof.

The invention also relates to novel intermediates and to pharmaceutical compositions containing compounds of the above formulae in admixture with one or more pharmaceutically acceptable, non-toxic carriers.

DETAILED DESCRIPTION OF THE INVENTION

The present invention provides various 2-imidazoline, 2-oxazoline, 2-thiazoline, and 4-imidazole derivatives of methylphenyl, methoxyphenyl, and aminophenyl alkylsulfonamides and ureas, and their use in the treatment of various disease states, including urinary incontinence, nasal congestion, priapism, depression, anxiety, dementia, senility, Alzheimer's, deficiencies in attentiveness and cognition, and eating disorders such as obesity, bulimia, and anorexia. For example, the compounds of the present invention are selective, orally-active alpha$_{1A/L}$-adrenoceptor agonists for the medical treatment of mild to moderate genuine stress urinary incontinence. The compounds are selective in that they increase lower urinary tract smooth muscle tone with little or no effect on the vasculature (i.e., vasoconstriction), heart, or central nervous system (CNS).

Before proceeding further with a description of the preferred embodiments of the present inventions, a number of terms will be defined.

Definitions

As used herein:

"Alkyl" means a branched or unbranched saturated monovalent hydrocarbon radical containing 1 to 10 carbon atoms inclusive, such as methyl, ethyl, propyl, iso-propyl, tert-butyl, n-hexyl, n-octyl, and the like.

"Lower alkyl" means a branched or unbranched saturated monovalent hydrocarbon radical containing 1 to 6 carbon atoms inclusive, such as methyl, ethyl, propyl, iso-propyl, tert-butyl, butyl, n-pentyl, and the like.

"Lower alkoxy" means the group —O-(lower alkyl) wherein lower alkyl is as herein defined.

"Cycloalkyl" means a saturated monovalent monocyclic hydrocarbon radical containing 3 to 8 carbon atoms inclusive, such as cyclopropyl, cyclobutyl, cyclopentyl, cyclohexyl, cycloheptyl, cyclooctyl, and the like.

"Lower alkylene" means a branched or unbranched saturated divalent hydrocarbon radical containing 1 to 6 carbon atoms inclusive, such as methylene, ethylene, propylene, 2-methylpropylene, 1,2-dimethylpropylene, pentylene, and the like.

"Lower alkenyl" means a branched or unbranched unsaturated hydrocarbon radical containing at least one ethenylic bond and 2 to 6 carbon atoms inclusive, such as ethenyl, propenyl, n-butenyl, isopropenyl, isobutenyl, n-pentenyl, isopentenyl, and the like.

"Lower alkenylene" means a branched or unbranched unsaturated divalent hydrocarbon radical containing at least one ethenylic bond and 2 to 6 carbon atoms inclusive, such as ethenylene, propenylene, 2-methylpropenylene, 1,2-dimethylpropenylene, pentenylene, and the like.

"Inert organic solvent" or "inert solvent" mean a solvent inert under the conditions of the reaction being described in conjunction therewith, including, for example, benzene, toluene, acetonitrile, tetrahydrofuran ("THF"), dimethylformamide ("DMF"), chloroform ("CHCl$_3$"), methylene chloride (or dichloromethane or "$CH_2Cl_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

"Halogen" means fluorine, chlorine, bromine, or iodine.

"Halo" means fluoro, chloro, bromo, or iodo.

"Halide" means fluoride, chloride, bromide, or iodide.

"Phenyl" means all possible isomeric phenyl radicals optionally monosubstituted or disubstituted with a substituent selected from the group consisting of lower alkyl, lower alkoxy, and halogen.

"Phenyl lower alkyl" means phenyl as defined above attached to a lower alkyl group as defined above.

"2-imidazoline" means the moiety designated by the structure:

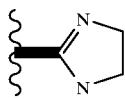

It is to be understood that the double bond in the 2-imidazoline may assume other resonance forms depending the nature of X in the above formulae. When X is —NH—, the resonance form that is stable is the following:

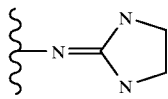

The term 2-imidazoline includes all such resonance forms.

"2-oxazoline" means the moiety designated by the structure:

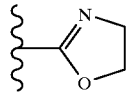

The term 2-oxazoline includes all resonance forms of the above.

"2-thiazoline" means the moiety designated by the structure:

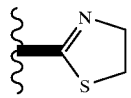

The term 2-thiazoline includes all resonance forms of the above.

"4-imidazole" means the moiety designated by the structure:

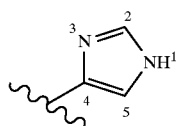

It should be understood that various numbering approaches have been used for the above moiety. The 4-position referred to above is based on the designation of the nitrogen in the above formula with the number 1. However, if one were to employ the following numbering approach, the position of attachment of the imidazole in the present compounds would be the 5-position:

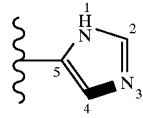

Another approach has been to designate the position of attachment as 4(5)-imidazole.

"Pharmaceutically acceptable salt" means those salts which retain the biological effectiveness and properties of the free bases and which are not biologically or otherwise undesirable, formed with inorganic acids such as hydrochloric acid, hydrobromic acid, sulfuric acid, nitric acid, phosphoric acid, and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. "Pharmaceutically acceptable salt" includes solvates, particularly hydrates, of such salts.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

"Isomers" are different compounds that have the same molecular formula.

"Treatment" means any treatment of any disease state in a mammal, particularly a human, and includes:

(i) preventing the disease from occurring in a subject which may be predisposed to the disease but has not yet been diagnosed as having it;

(ii) inhibiting the disease, i.e. arresting its development; and/or (iii) relieving the disease, i.e. causing regression of the disease.

"Disease state which is alleviated by treatment with an $alpha_1$-adrenoceptor agonist" as used herein is intended to cover all disease states which are generally acknowledged in the art to be usefully treated with $alpha_1$-adrenoceptor agonists in general, and those disease states which have been found to be usefully treated by the specific $alpha_1$-adrenoceptor agonists of the present invention, the compounds of the above formulae. Such disease states include, for example, urinary incontinence, particularly mild to moderate genuine stress urinary incontinence, nasal congestion, priapism, depression, anxiety, dementia, senility, Alzheimer's, deficiencies in attentiveness and cognition, and eating disorders such as obesity, bulimia, and anorexia.

"Therapeutically effective amount" means that amount which is sufficient to effect treatment, as defined above, when administered to a mammal in need of such treatment. The therapeutically effective amount will vary depending on the subject and disease state being treated, the severity of the affliction, and the manner of administration, and may be determined routinely by one of ordinary skill in the art.

Preferred Embodiments

Among the family of compounds of the present invention, a preferred group includes the following compounds of Formula 1:

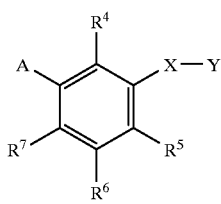

wherein: A is ($R^1SO_2NR^2-$), ($R^3R^{60}NSO_2NR^2-$), or ($R^3R^{60}NCONR^2-$); X is $-NH-$, $-CH_2-$, or $-OCH_2-$; Y is 2-imidazoline, 2-oxazoline, 2-thiazoline, or 4-imidazole; $R^1$ is H, lower alkyl, or phenyl; $R^2$, $R^3$, and $R^{60}$ are each independently H, lower alkyl, or phenyl; $R^4$, $R^5$, $R^6$, and $R^7$ are each independently hydrogen, lower alkyl, $-CF_3$, lower alkoxy, halogen, phenyl, lower alkenyl, hydroxyl, lower alkylsulfonamido, or lower cycloalkyl, wherein $R^2$ and $R^7$ optionally may be taken together to form alkylene or alkenylene of 2 to 3 carbon atoms in an unsubstituted or optionally substituted 5- or 6-membered ring, wherein the optional substituents on the ring are halo, lower alkyl, or $-CN$, with the proviso that, when $R^7$ is hydroxyl or lower alkylsulfonamido, then X is not $-NH-$ when Y is 2-imidazoline. The compounds include pharmaceutically acceptable salts of the above.

In Formula 1 above, other preferred embodiments include wherein $R^1$ is methyl, ethyl, propyl, or phenyl; or a pharmaceutically acceptable salt thereof. Other preferred embodiments include wherein all but one of $R^4$, $R^5$, $R^6$, and $R^7$ are hydrogen and the remaining one is selected from the group consisting of methyl, ethyl, $-CF_3$, methoxy, chlorine, bromine, fluorine, isopropyl, cyclopropyl, ethenyl, hydroxy, and methylsulfonamido; or a pharmaceutically acceptable salt thereof. Still other preferred embodiments include wherein all but two of $R^4$, $R^5$, $R^6$, and $R^7$ are hydrogen and the remaining two are each independently selected from the group consisting of methyl, ethyl, isopropyl, $-CF_3$, chlorine, bromine, and fluorine; or a pharmaceutically acceptable salt thereof. Still other preferred embodiments include wherein $R^2$ and $R^7$ are taken together to form ethenylene in an unsubstituted or substituted 5-membered ring, wherein the optional substituents on the ring are halo, lower alkyl, or $-CN$, preferably chloro, bromo, or $-CN$; or a pharmaceutically acceptable salt thereof.

In Formula 2 above, preferred embodiments include wherein $R^8$ is methyl, ethyl, propyl, phenyl, amino, methylamino, or dimethylamino; or a pharmaceutically acceptable salt thereof. Other preferred embodiments include wherein all but one of $R^{10}$, $R^{11}$, $R^{12}$, and $R^{13}$ are hydrogen and the remaining one is selected from the group consisting of methyl, ethyl, $-CF_3$, methoxy, chlorine, bromine, fluorine, isopropyl, cyclopropyl, ethenyl, hydroxy, and methylsulfonamido; or a pharmaceutically acceptable salt thereof. Still other preferred embodiments include wherein all but two of $R^{10}$, $R^{11}$, $R^{12}$, and $R^{13}$ are hydrogen and the remaining two are each independently selected from the group consisting of methyl, ethyl, isopropyl, $-CF_3$, chlorine, bromine, and fluorine; or a pharmaceutically acceptable salt thereof. Still other preferred embodiments include wherein $R^9$ and $R^{13}$ are taken together to form ethenylene in a 5-membered ring, or a pharmaceutically acceptable salt thereof.

In Formula 3 above, preferred embodiments include wherein $R^{16}$ is methyl, or a pharmaceutically acceptable salt thereof. Other preferred embodiments include wherein all but one of $R^{18}$, $R^{19}$, $R^{20}$, and $R^{21}$ are hydrogen and the remaining one is selected from the group consisting of methyl, ethyl, isopropyl, $-CF_3$, methoxy, fluorine, chlorine, and bromine; or a pharmaceutically acceptable salt thereof. Still other preferred embodiments wherein all but two of $R^{18}$, $R^{19}$, $R^{20}$, and $R^{21}$ are hydrogen and the remaining two are each independently selected from the group consisting of methyl, ethyl, isopropyl, $-CF_3$, methoxy, fluorine, chlorine, and bromine; or a pharmaceutically acceptable salt thereof. Still other preferred embodiments include wherein $R^{16}$ is methyl and $R^{17}$ is H; or a pharmaceutically acceptable salt thereof.

In Formula 4 above, preferred embodiments include wherein $R^{22}$ is methyl, ethyl, or isopropyl; or a pharmaceutically acceptable salt thereof. Other preferred embodiments include wherein $R^{23}$ is hydrogen or methyl; or a pharmaceutically acceptable salt thereof. Still other preferred embodiments include wherein all but one of $R^{24}$, $R^{25}$, $R^{26}$, and $R^{27}$ are hydrogen and the remaining one is selected from the group consisting of methyl, ethyl, isopropyl, ethenyl, $-CF_3$, methoxy, hydroxy, phenyl, fluorine, chlorine, bromine, and methylsulfonamido; or a pharmaceutically acceptable salt thereof. Still other preferred embodiments include wherein all but two of $R^{24}$, $R^{25}$, $R^{26}$, and $R^{27}$ are hydrogen and the remaining two are each independently selected from the group consisting of methyl, ethyl, chlorine, and bromine; or a pharmaceutically acceptable salt thereof. Still other preferred embodiments include wherein $Y^c$ is 2-imidazoline or 4-imidazole, $R^{22}$ is methyl, and $R^{23}$ is H; or a pharmaceutically acceptable salt thereof.

In Formula 5 above, preferred embodiments include wherein $R^{28}$ is methyl, ethyl, propyl, or phenyl; or a pharmaceutically acceptable salt thereof. Other preferred embodiments include wherein all but one of $R^{30}$, $R^{31}$, $R^{32}$, and $R^{33}$ are hydrogen and the remaining one is selected from the group consisting of cyclopropyl, chlorine, fluorine, hydroxy, methyl, and ethyl; or a pharmaceutically acceptable salt thereof. Still other preferred embodiments include wherein all but two of $R^{30}$, $R^{31}$, $R^{32}$, and $R^{33}$ are hydrogen and the remaining two are each independently selected from the group consisting of methyl, ethyl, chlorine, and bromine; or a pharmaceutically acceptable salt thereof. Still other preferred embodiments include wherein $Y^d$ is 2-imidazoline or 4-imidazole and $R^{28}$ is methyl; or a pharmaceutically acceptable salt thereof. Still other preferred embodiments include wherein $Y^d$ is 2-imidazoline, $R^{28}$ is methyl, $R^{30}$ is methyl, and $R^{33}$ is halogen; or a pharmaceutically acceptable salt thereof. Still other preferred embodiments include wherein $Y^d$ is 2-imidazoline, $R^{28}$ is methyl, $R^{30}$ is methyl, and is $R^{33}$ chlorine or bromine.

In Formula 6 above, preferred embodiments include wherein $R^{16}$ is methyl, or a pharmaceutically acceptable salt thereof. Other preferred embodiments include wherein no more than one of $R^{34}$, $R^{35}$, and $R^{36}$ is Cl, Br, or F; or a pharmaceutically acceptable salt thereof. Still other preferred embodiments include wherein $R^{34}$, $R^{35}$, and $R^{36}$ are each independently H, Cl, Br, F, methyl, or ethyl; or a pharmaceutically acceptable salt thereof.

In Formula 7 above, preferred embodiments include wherein $R^{22}$ is methyl, or a pharmaceutically acceptable salt thereof. Other preferred embodiments include wherein no more than one of $R^{34}$, $R^{35}$, and $R^{36}$ is Cl, Br, or F; or a pharmaceutically acceptable salt thereof. Still other preferred embodiments include wherein $R^{34}$, $R^{35}$, and $R^{36}$ are each independently H, Cl, Br, F, methyl, or ethyl; or a pharmaceutically acceptable salt thereof.

In Formula 8 above, preferred embodiments include wherein $R^{28}$ is methyl, or a pharmaceutically acceptable salt thereof. Other preferred embodiments include wherein no more than one of $R^{34}$, $R^{35}$, and $R^{36}$ is Cl, Br, or F; or a pharmaceutically acceptable salt thereof. Still other preferred embodiments include wherein $R^{34}$, $R^{35}$, and $R^{36}$ are each independently H, Cl, Br, F, methyl, or ethyl; or a pharmaceutically acceptable salt thereof.

In Formula 76 above, preferred embodiments include wherein $R^{56}$ is CH=CH, $R^{57}$, $R^{58}$ and $R^{59}$ are H, and $Y^g$ is imidazoliine; or a pharmaceutically acceptable salt thereof.

In Formula 75 above, preferred embodiments include wherein $X^f$ is —NH—, $Y^f$ is 2-oxaxoline, $R^{48}$ and $R^{50}$ are $CH_3$, and $R^{49}$, $R^{51}$, $R^{52}$, and $R^{53}$ are H; or a pharmaceutically acceptable salt thereof.

In Formula 74 above, preferred embodiments include wherein $X^e$ is —OCH$_2$—, $Y^e$ is 2-imidazoline, $R^{41}$ and $R^{43}$ are $CH_3$, and $R^{42}$, $R^{44}$, $R^{45}$, $R^{46}$, and $R^{47}$ are H; or a pharmaceutically acceptable salt thereof.

METHODS OF PREPARATION

The preparation of the compounds of Formula 1:

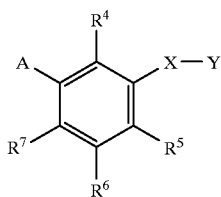

1 generally involves the introduction of the "A" moiety and the "—X—Y" moiety into the phenyl ring. The following discussion relating to Schemes A–E involves the separate introduction of the above moieties. It will be appreciated that for any given compound, consideration must be given to the introduction of both moieties. The following discussion of Schemes A–E is, therefore, for purposes of illustration and not limitation.

In general, introduction of A in the above compounds depends on the nature of A. Wherein A is $R^1SO_2NR^2$— or $R^3R^{60}NCONR^2$—, an amine is introduced into the structure either by virtue of an appropriate aminophenyl compound that is commercially available or whose synthesis is known. Where such an aminophenyl compound is not commercially available or synthesis is not known, the corresponding nitrophenyl compound may be employed and the nitro group reduced by appropriate means to an amino group. A nitro group may be introduced into an appropriate phenyl compound by known techniques if the desired nitrophenyl compound is not otherwise available. The amine group is reacted with an appropriate alkylsulfonyl halide or alkylsulfonic anhydride.

The introduction of an A moiety may be illustrated by the following Scheme A:

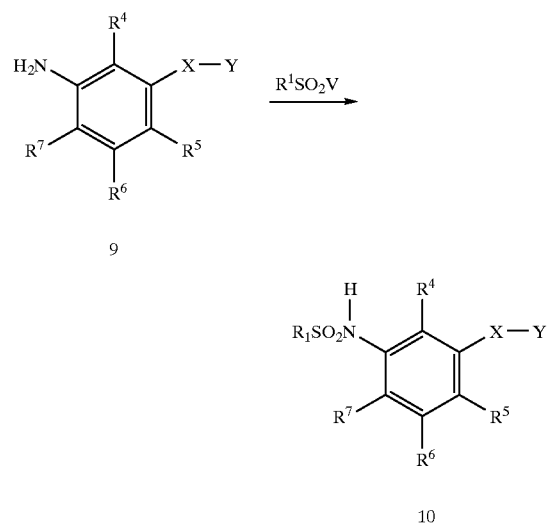

The amine group in the precursor compound is reacted with the appropriate alkylsulfonyl halide ($R^1SO_2V$, wherein V is halide), such as alkylsulfonyl chloride, to give the desired alkylsulfonamide.

Various approaches are available for the introduction of the —X—Y moiety. In one approach for the introduction of a 2-imidazoline group in precursor compounds wherein X is —CH$_2$— or —OCH$_2$—, a cyano group is transformed to an imidate functionality, which is condensed with 1,2-diaminoethane to form the 2-imidazoline group. This approach is illustrated in Scheme B:

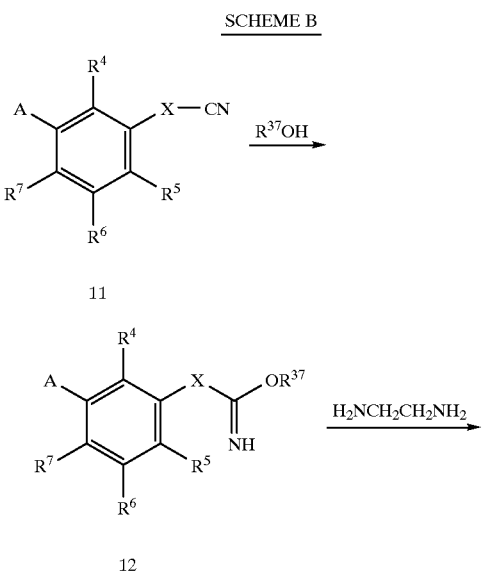

-continued

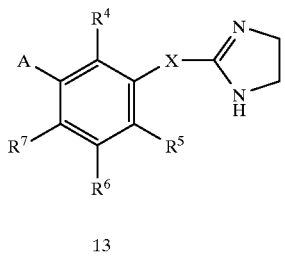

13

Alternatively, the cyano group may be reacted with ethylenediamine and trimethylaluminum in refluxing toluene to form directly the 2-imidazoline group (Wentland, et al., *J. Med. Chem.* (1987) 30:1482).

In another approach for the introduction of a 4-imidazole group in precursor compounds wherein X is —$CH_2$— or —$OCH_2$—, a cyano group is converted to an aldehyde, which is reacted with tosylmethylisocyanide to give dihydrooxazole (Buchi, et al., *Heterocycles* (1994) 39:139). The imidazole group is produced by treatment of the above compound with ammonia. This approach is illustrated in Scheme C:

SCHEME C

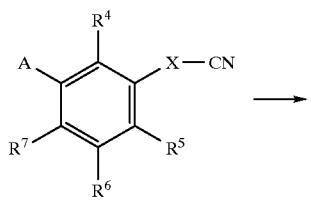

11

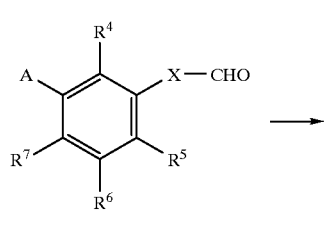

14

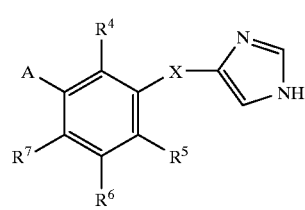

13

In another approach for the introduction of a 2-imidazoline group in precursor compounds wherein X is —NH—, an amine group is reacted with 2-haloimidazoline to produce the desired compound directly. As mentioned above, an amine group may be introduced into the phenyl ring by reduction of a nitro group. The latter compounds may be commercially available or their synthesis may be known. Alternatively, a nitro group may be introduced into the phenyl ring as described above. This approach is illustrated in Scheme D, wherein the V moiety of the reagent is halogen or $SCH_3$ and wherein, when V is $SCH_3$, the reagent is a hydrogen iodide salt:

SCHEME D

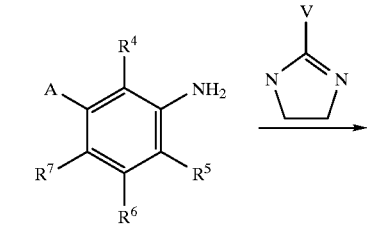

15

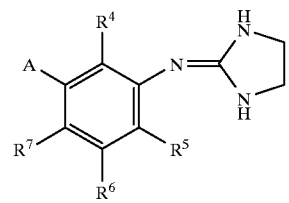

16

For those compounds wherein A is $R^3R^{60}NSO_2NR^2$—, the following illustrative Scheme E may be employed. The amine group in the precursor compound is reacted with the appropriate alkylsulfamoyl halide ($R^3R^{60}NSO_2V^1$, wherein $V^1$ is halide).

SCHEME E

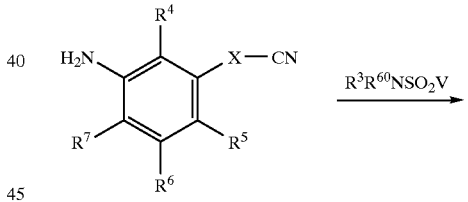

17

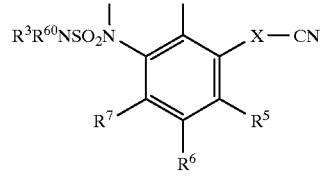

18

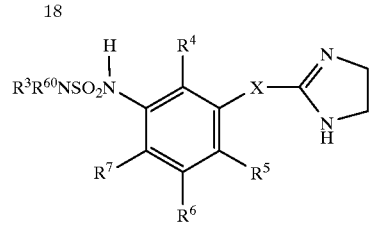

19

The following reaction schemes for preparation of certain specific compounds in accordance with the present invention illustrate one or more of the above general synthetic approaches, which are described in more detail.

Scheme F summarizes an approach for the preparation of compounds of Formula 1 wherein A is $R^1SO_2NH—$, X is $—CH_2—$ or $—OCH_2—$, and Y is 2-imidazoline.

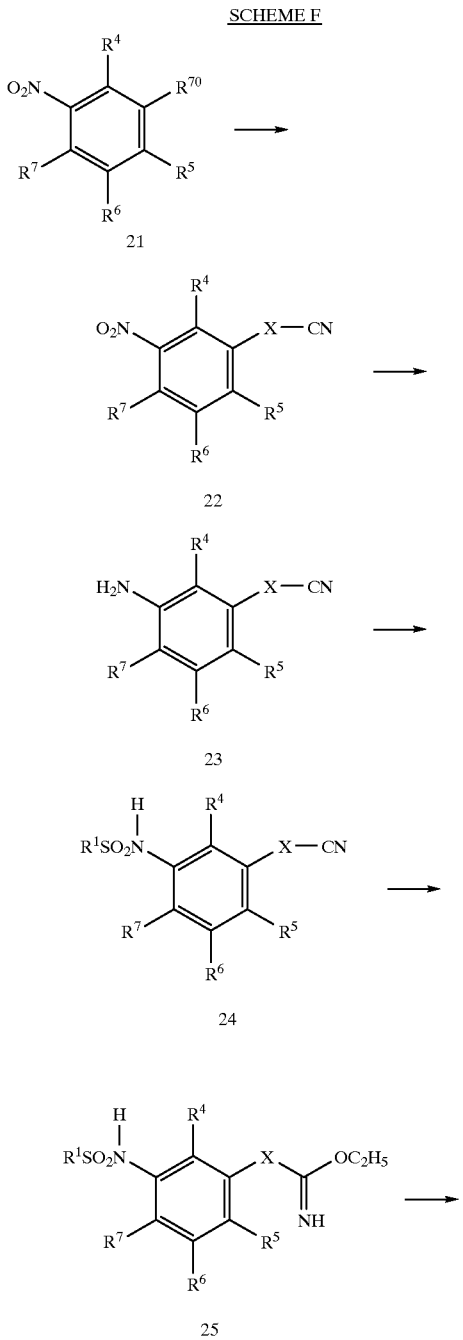

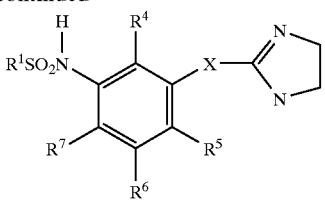

Compound 21 is treated to introduce a —CN group. When X is $—CH_2—$, $R^{70}$ is X—Cl and the approach involves reacting compound 21 with cyanide ion (0.5 to 3, preferably 1 to 2, moles per mole of compound 21) such as that in sodium cyanide, potassium cyanide, and the like in an inert organic solvent such as dimethylformamide, ethanol, dioxane, and so forth. The reaction may be enhanced further by inclusion of a catalyst such as sodium iodide, potassium iodide, lithium iodide, and the like. The reaction is carried out at a temperature of about 60 to 90° C., preferably 70 to 80° C., for a period of about 1 to 24 hours, preferably 3 to 12 hours, usually under an inert gas such as nitrogen, argon, and the like. The resulting product is isolated by cooling the reaction mixture to ambient temperature and mixing the reaction mixture with 1 to 20, preferably 5 to 10, times its amount of an ether solvent such as diethyl ether, dimethoxyethane, dioxane, tetrahydrofuran, and the like. The resulting product, compound 22, is then washed with a saturated salt solution such as saturated sodium chloride.

Wherein X is $—OCH_2—$ and $R^{70}$ is —OH, the CN group may be introduced by treatment of compound 21 with a haloacetonitrile, such as, e.g., $BrCH_2CN$, or cyanomethyl tosylate in the presence of strong base such as sodium hydride, $NaN(TMS)_2$, or KOtBu and the like in a suitable organic solvent such as dimethylformamide, dioxane, tetrahydrofuran, and the like. Usually, about 0.5 to 3, preferably 1 to 2, moles of the haloacetonitrile is employed per mole of compound 21. The reaction is carried out by adding the hydride to the solvent cooled in an ice bath and then warmed to room temperature. Compound 21 is then added to the solvent cooled in an ice bath. The reaction is carried out for a period of about 1 to 24 hours, preferably 3 to 12 hours. The resulting product, compound 22, is then recovered.

In an alternative embodiment wherein X is $—OCH_2—$ and $R^{70}$ is —OH, the CN group may be introduced by treatment of compound 21 with a haloacetonitrile, such as, e.g., $BrCH_2CN$, in the presence of $Cs_2CO_3$, $K_2CO_3$, and the like in methylethylketone, acetone, and so forth. Usually, about 1 to 4, preferably 2 to 3, moles of the $Cs_2CO_3$ is employed per mole of compound 21 and about 0.3 to 3, preferably about 1 to 2, moles haloacetonitrile is employed per mole of compound 21. The reaction is carried out for a period of about 1 to 24 hours, preferably 2 to 6 hours. The resulting product, compound 22, is then recovered.

Compound 22 is next treated to reduce, i.e., to hydrogenate, the nitro group to give an amino group. This may be accomplished in a number of ways. For example, in one approach compound 22 is hydrogenated in an inert solvent such as ethyl acetate, methanol, ethanol, and the like, with a suitable heterogeneous catalyst, for example palladium on carbon, platinum oxide, or rhodium on alumina, to give compound 23. For example, for every gram of compound 22 which is added, from 0.01 to 0.1 g, preferably about 0.05 g, of 10% palladium on carbon catalyst is employed and the mixture hydrogenated at a pressure of about 30 to 60 psi, preferably about 40 to 50 psi. The reaction is conducted at a temperature of about 0 to 50° C., preferably about 25° C., for about 24 to 72 hours, preferably about 42 hours. Alternatively, hydrogenation can be carried out using tin (II) chloride in ethanol and ethyl acetate. Usually, about 1 to 5, preferably 3 to 4, moles of tin (II) chloride are employed per mole of compound 22. The reaction is conducted at a temperature of about 20 to 90° C., preferably about 60 to 70° C., for about 24 to 72 hours, preferably about 24 to 48 hours. Following hydrogenation with tin (II) chloride, the reaction mixture is cooled to ambient temperature and combined with an inert organic solvent such as ethyl acetate. The reaction mixture is neutralized by the addition of an appropriate base such as sodium bicarbonate. The reaction product of either of the above approaches may be isolated by conventional means and the mixture subjected to chromatography such as on silica gel, eluting with a suitable solvent such as methylene chloride or a mixture thereof such as, for example, 5 to 20% methanol in methylene chloride.

Compound 23 above is next treated to form the alkylsulfonamide (compound 24). To this end compound 23 is combined with an appropriate alkylsulfonyl halide such as alkylsulfonyl chloride in an inert organic solvent such as pyridine, dichloromethane with a base such as triethylamine, and the like. Usually, about 1 to 3, preferably 1.5 to 2, moles of the alkylsulfonyl halide are employed per mole of compound 23. The reaction is conducted at a temperature of about −10 to 50° C., preferably about 0 to 10° C., for about 4 to 24 hours, preferably about 6 to 8 hours. The reaction mixture is treated to hydrolyze the unreacted alkylsulfonyl chloride, for example, by adding a sufficient amount of water and warming the reaction mixture to ambient temperature. The reaction mixture is next acidified to a pH of about 1 to 3, preferably pH 1, by the addition of an appropriate acid such as hydrochloric acid. The product, compound 24, is obtained as a solid, which is dried in conventional manner.

Compound 24 from above is treated to introduce the 2-imidazoline moiety. To this end compound 24 is treated first to form an imidate functionality. Compound 24 is suspended in an inert organic solvent such as methylene chloride and about 1 to 4, preferably 2 to 3, moles of ethanol per mole of compound 24 is added and the reaction mixture is cooled to about −10 to 50° C., preferably about 0 to 10° C. A mineral acid such as anhydrous HCl in a gaseous form is bubbled into the mixture to complete saturation of the mixture, which requires about 20 to 60, usually 25 to 35, minutes. The reaction mixture is stirred for a period of about 30 minutes to 5 hours, preferably 1 to 2 hours, and then the temperature is raised to ambient and the reaction mixture stirred for 6 to 24, preferably 10 to 12, hours. Compound 25 is obtained by evaporation of the solvent and addition of an inert organic solvent such as methylene chloride followed by evaporation.

The 2-imidazoline group is formed from compound 25 by addition of about 1 to 2, preferably 1.2 to 1.5, moles of 1,2-diaminoethane (ethylenediamine) per mole of compound 25. The reaction is carried out in a suitable inert organic solvent such as an alcohol, e.g., methanol, at a temperature of about 20 to 50° C., preferably about 20 to 30° C., for about 4 to 24 hours, preferably about 10 to 20 hours, under an inert gas such as nitrogen, argon, and the like.

Solvent is removed by evaporation and then the reaction product is treated with strong base such as ammonium hydroxide to liberate the salt. The resulting compound 26 is next subjected to evaporation from a variety of inert organic solvents such as methanol, methylene chloride, and the like.

Alternatively, compound 26 can be obtained directly from compound 24 by treatment with ethylene diamine and trimethylaluminum (Wentland, et al., supra).

Scheme G summarizes an approach for the preparation of compounds of Formula 1 wherein A is $R^1SO_2NH-$, X is $-CH_2-$, and Y is 4-imidazole.

SCHEME G

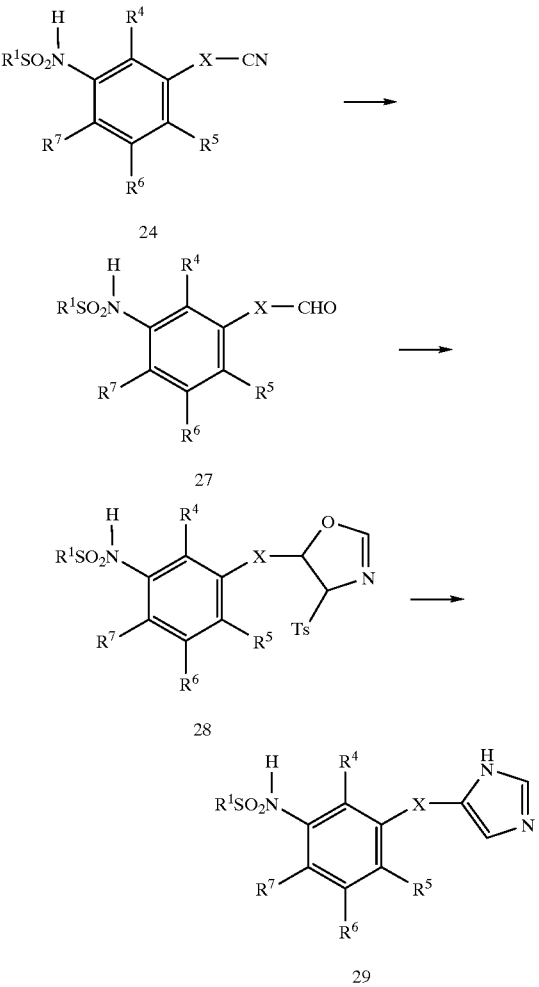

Compound 24, prepared as described above, is treated to convert the cyano group to an aldehyde. This may be accomplished, for example, by combining compound 24 with a suitable reducing agent such as DIBAL, lithium triethylalumino hydride, and the like. Compound 24 is suspended in an inert organic solvent such as an ether solvent, e.g., diethyl ether, dimethoxyethane, dioxane, tetrahydrofuran, and the like. The reaction mixture is cooled to about −10 to 50° C., preferably about 0 to 10° C. and about 3 to 7, preferably 4 to 5, moles of DIBAL per mole of compound 24 is added. The reaction mixture is stirred for about 30 minutes to 3 hours, preferably 1 to 2 hours, and then the excess DIBAL is destroyed by addition of excess methanol or the like. The solvent is evaporated and the resulting product compound 27 is subjected to neutralization by addition of an inert organic solvent such as ethyl acetate and an acid such as hydrochloric acid to pH of about 1 to 2, preferably pH 1. The reaction product is extracted with a suitable inert organic solvent such as ethyl acetate, washed with saturated salt solution such as saturated sodium chloride, and dried to give compound 27.

The aldehyde functionality of compound 27 is next converted to a dihydrooxazole (Buchi, et al., supra) by dissolving compound 27 in an inert organic solvent such as an alcohol, e.g., ethanol, methanol, and the like, and about 1 to 3, preferably about 1 to 1.5, moles of an appropriate isocyanide such as tosyl methyl isocyanide, and the like, are added per mole of compound 27, followed by about 0.05 to 0.5, preferably about 0.1 to 0.2, moles of cyanide ion such as sodium cyanide, potassium cyanide, and the like. The reaction mixture is stirred at a temperature of about 20 to 30° C., preferably about 20 to 25° C., for a period of about 6 to 24 hours, preferably 10 to 12 hours, under an inert gas such as nitrogen, argon, and the like. The reaction mixture is filtered and the dihydrooxazole product, compound 28, is dried.

The desired 4-imidazole product, compound 29, is obtained from compound 28 by treatment with ammonia. The reaction is usually carried out in a sealed container. Compound 28 is suspended in about 10 to 20, preferably 10 to 15, moles of ammonia per mole of compound 28 in an inert organic solvent, for example, an alcohol such as isopropyl alcohol, methanol, ethanol, and the like. The reaction mixture is stirred at a temperature of about 80 to 120° C., preferably about 90 to 100° C., for a period of about 3 to 8 hours, preferably 4 to 6 hour. The reaction mixture is cooled to ambient temperature and the sealed container is opened. The solvent is removed by evaporation and the resulting product, compound 29, is purified by chromatography.

An alternative approach for introduction of the 4-imidazole group into the compounds of Formula 1 wherein A is $R^1SO_2NH$—, X is —$CH_2$— or —$OCH_2$—, and Y is 4-imidazole is summarized in Scheme H:

SCHEME H

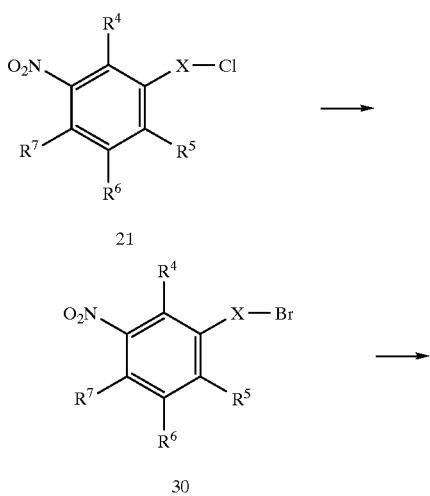

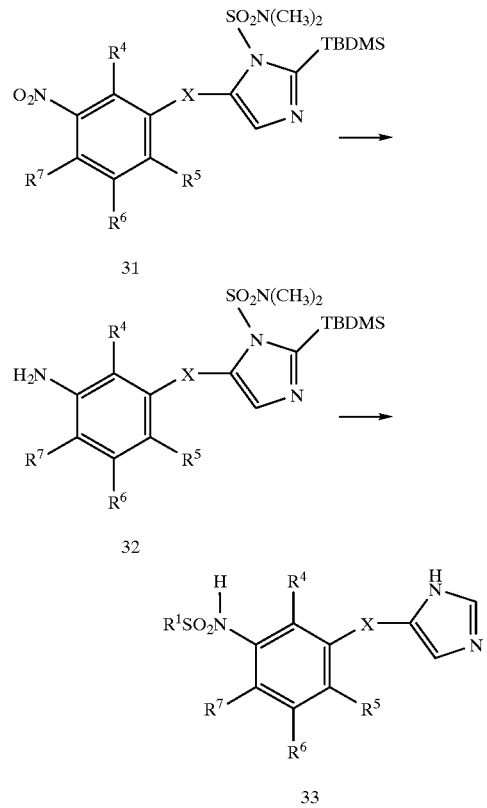

In this approach compound 21 from above is converted to the bromide compound 30 by conventional means such as by reaction of compound 21 with lithium bromide (J. Am. Chem. Soc. (1955) 77:4903). A strong base such as, for example, n-alkyl lithium, e.g., n-butyl lithium, in excess, is combined with 2-(t-butyldimethylsilyl)-1-(N,N-dimethylsulfamoyl)-imidazole (Ngochindo, J. Chem. Soc. Perkin Trans. I. (1990) 1645) (about 0.5 to 2.0, preferably about 0.8 to 1.2, moles per mole of compound 21) in a suitable inert organic solvent such as an ether solvent, e.g., tetrahydrofuran, diethyl ether, dimethoxyethane, dioxane, and the like. The above mixture is cooled to a temperature of about -50 to -100° C., preferably about -78° C., and compound 30 is added. The reaction mixture is stirred for a period of about 6 to 24, preferably about 10 to 12, hours during which time the temperature is allowed to warm to ambient temperature. The resulting product, compound 31, is subjected to various washings with inert organic solvents followed by brine and is then subjected to column chromatography using a suitable solvent system such as, for example, ethyl acetate/hexane, hexane, and the like.

Compound 31 is treated to convert the nitro group to an amine group of compound 32 in a manner similar to that described above in Scheme F for the conversion of compound 22 to compound 23. The desired product, compound 33, is obtained during the formation of the alkylsulfonamide group, which is obtained in a manner similar to that described above in Scheme F for the conversion of compound 23 to compound 24. The protective groups in compound 32 are removed during the acid work-up procedures.

An alternative approach for introduction of the 4-imidazole group into the compounds of Formula 1 wherein A is $R_1SO_2NH$—, X is —$OCH_2$—, and Y is 4-imidazole is summarized in Scheme I:

SCHEME I

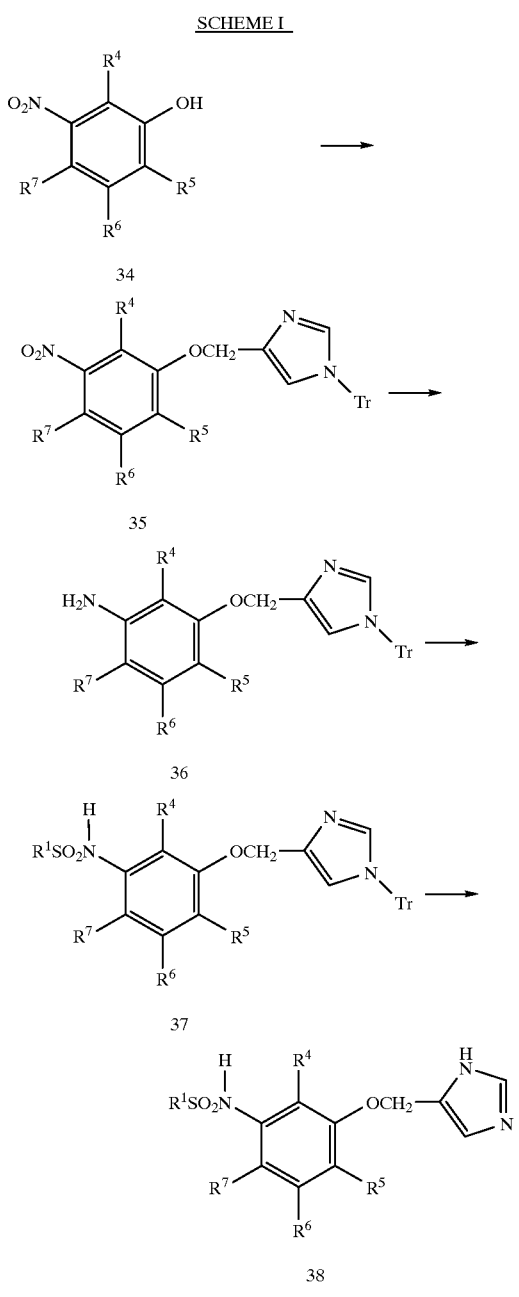

Compound 34, a 3-nitrophenol, is combined with (1-trityl-1H-imidazol-4-yl)-methanol prepared by reaction of (1H-imidazol-4-yl)-methanol with trityl (Tr) chloride. The reaction is conducted in an inert organic solvent such as an ether solvent, e.g., tetrahydrofuran, diethyl ether, dimethoxyethane, dioxane, and the like in the presence of DEAD (diethyl azodicarboxylate) ant triphenyl phosphine (Mitsunobu, *Synthesis* (1981) 1). The reaction is usually carried out using about 2 moles of DEAD and 2 moles of triphenyl phosphine per mole of compound 34. The reaction mixture is stirred at a temperature of about −10 to 60° C., preferably about 20 to about 30° C., for a period of about 1 to 72 hours, preferably about 2 to 24 hours. The reaction mixture is cooled to ambient temperature and the resulting product, compound 35, is purified by chromatography.

The nitro group of compound 35 is converted to an amine group to give compound 36 in a manner similiar to that described above in Scheme F for the conversion of compound 22 to compound 23. Compound 37 is obtained in a manner similar to that described above in Scheme F for the conversion of compound 23 to compound 24. The desired product, compound 38, is obtained by hydrolyzing the trityl group in compound 37 in a conventional manner such as by treatment with dilute inorganic acid such as hydrochloric acid in an inert organic solvent such as acetonitrile.

Scheme J summarizes an approach for the preparation of compounds of Formula 1 wherein A is $R^1SO_2NH$—, X is —NH—, and Y is 2-imidazoline.

SCHEME J

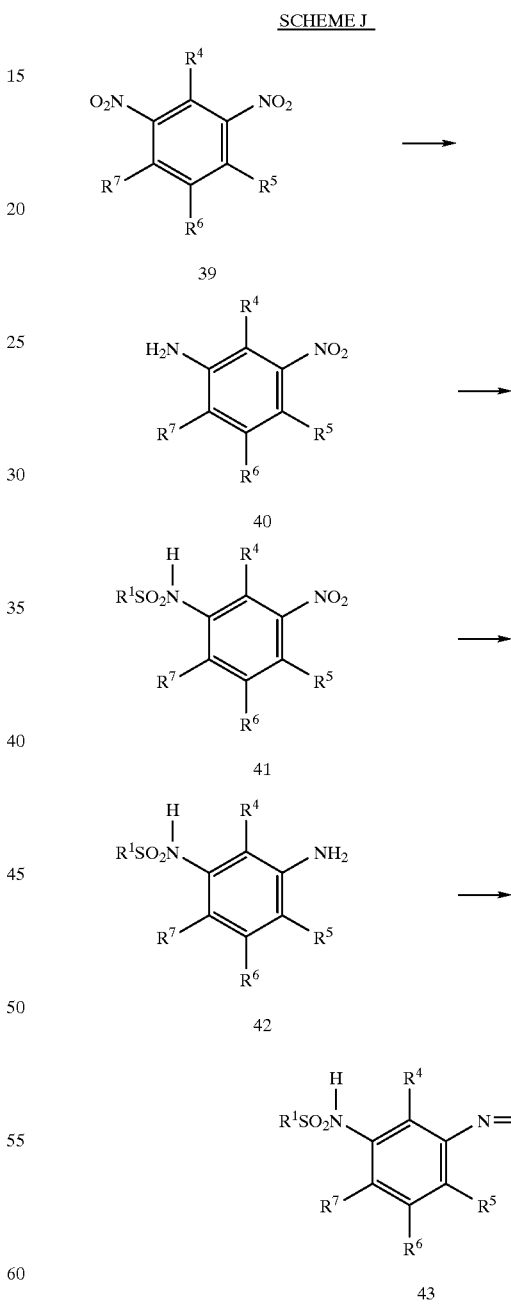

Compound 39 is treated under mild conditions to convert one of the nitro groups to an amine group of compound 40. To this end compound 39 is reacted with a mild reducing agent such as, for example, sodium dithionite, ammonium sulfide, sodium sulfide, and the like. The reaction is generally carried out in an aqueous organic solvent such as an alcohol (methanol, ethanol, etc.)/water mixture where the water may be present at 20 to 80% by volume. Compound 41 is obtained from compound 40 in a manner similar to that described above in Scheme F for the conversion of compound 23 to compound 24. The nitro group of compound 41 is converted to an amine group to give compound 42 in a manner similar to that described above in Scheme F for the conversion of compound 22 to compound 23. The desired product, compound 43, is obtained by treatment of compound 42 with 2-chloroimidazoline where 2 to 5 moles of 2-chloroimidazoline are combined with one mole of compound 42 in an inert organic solvent such as an alcohol, e.g., methanol, ethanol, isopropanol, and the like. The reaction mixture is stirred at a temperature of about 0 to 100° C., preferably about 25 to 80° C., for a period of about 0.5 to 48 hours, preferably about 1 to 24 hours. The reaction mixture is cooled to ambient temperature and the resulting product, compound 43, is purified by chromatography.

As will be appreciated the above Scheme J is suitable primarily in the preparation of the above compounds wherein $R^5$ and $R^7$ are H and $R^4$ and $R^6$ are other than H. Another approach to compounds wherein $R^4$ and $R^6$ are other than H is shown in Scheme K.

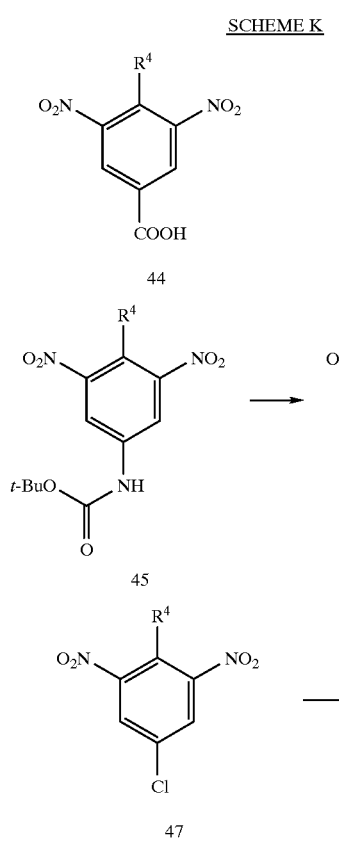

Compound 44 is treated with diphenylphosphoryl azide and a trialkyl amine such as triethyl amine in t-butanol (see, for example, Yamada, et al., *J. Am. Chem. Soc.* (1972) 94:6203) to convert the carboxylic acid moiety to the t-butyl carbamate compound 45. Hydrolysis of compound 45 to give compound 46 is carried out by the addition of an acid such as trifluoroacetic acid, hydrochloric acid, and the like (see, for example, Stahl, et al., *J. Org. Chem.* (1978) 43:2285). The amine group of compound 46 is converted to a chlorine substituent of compound 47 by reaction of compound 46 with t-butyl nitrite in an inert organic solvent such as acetonitrile, tetrahydrofuran, and the like in the presence of copper (II) chloride (see, for example, Doyle, et al., *J. Org. Chem.* (1977) 42:2426). The remaining part of the synthesis to convert compound 47 to the 2-imidazoline derivative is carried out as indicated in Scheme J above.

Another approach to compounds wherein $R^4$ and $R^6$ are other than H or where $R^6$ and $R^7$ are other than H is shown in Scheme L.

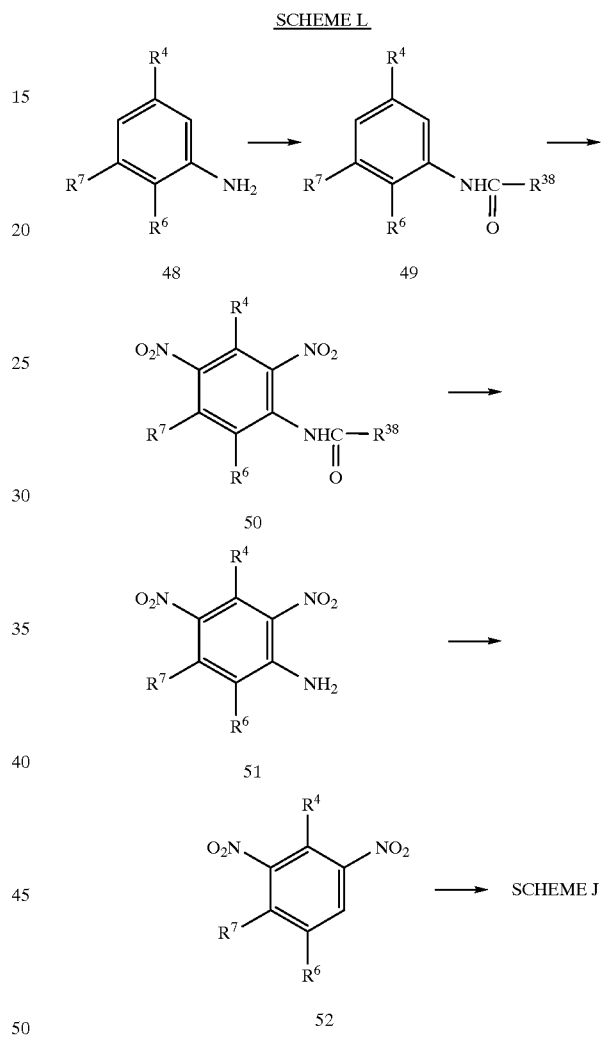

Compound 48 is treated in a conventional manner to form an amide (compound 49) such as by reaction with an acyl anhydride, e.g., acetic anhydride, propionic anhydride, or the like. Compound 49 is then treated to introduce the nitro groups as found in compound 50. To this end compound 49 is treated with nitric acid in a conventional manner (*Chem. Ber.* (1916) 49:622). The amide is hydrolyzed according to standard conditions such as aqueous mineral acid, e.g., sulfuric acid, in the presence of an alcohol such as, e.g., methanol, ethanol, and so forth to give compound 51, which is then treated to remove the amino group and give compound 52. To this end compound 51 is combined with t-butyl nitrite, isopentyl nitrite, benzyl nitrite, or the like in an inert organic solvent such as dimethylformamide, dioxane, tetrahydrofuran, and the like according to conventional procedures (see, for example, Doyle, et al., *J. Org. Chem.*

(1977) 42:3494). The remaining part of the synthesis to convert compound 52 to the 2-imidazoline derivative is carried out as indicated in Scheme J above.

The compounds of Formula 1 wherein $R^2$ and $R^7$ may be taken together to form alkylene or alkenylene of 2 to 3 carbon atoms in a 5- or 6-membered ring may be prepared by the following reaction schemes. For those compounds wherein X is —$CH_2$— and Y is 2-imidazoline, compound 53 is reacted with $R^1SO_2V$ wherein V is halogen in the presence of strong base such as $NaN(TMS)_2$ (TMS=trimethylsilyl) to give compound 54. The latter compound is converted to compound 55 in the presence of a reducing agent such as lithium aluminum hydride (LAH), lithium borohydride, borane-methyl sulfide complex, and the like. Compound 55 is treated to introduce a bromine using, for example, carbon tetrabromide and triphenyl phosphine ($Ph_3P$) or phosphorus tribromide and pyridine to give compound 56, which is converted to compound 57 in the presence of cyanide ion, e.g., sodium cyanide, potassium cyanide, and the like. Compound 58 can be produced from compound 57 by utilizing Scheme B above. The reaction scheme is set forth in Scheme M.

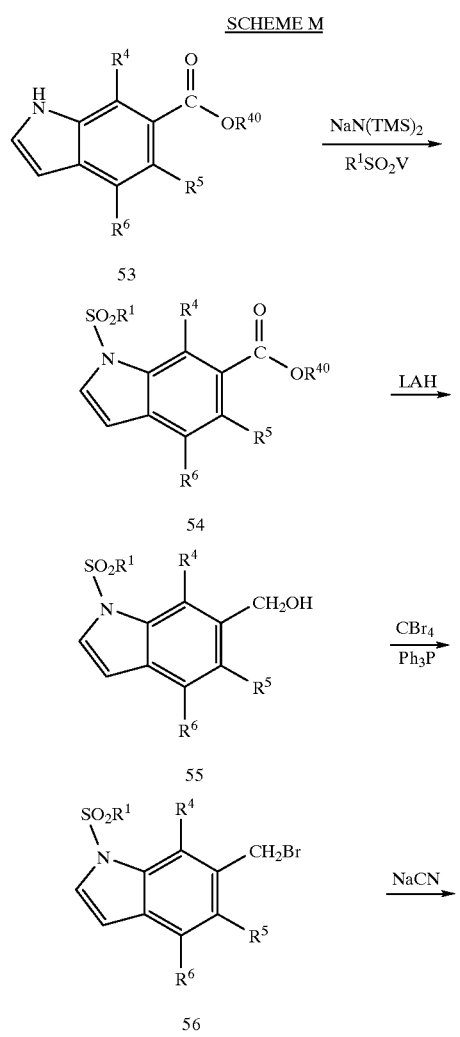

SCHEME M

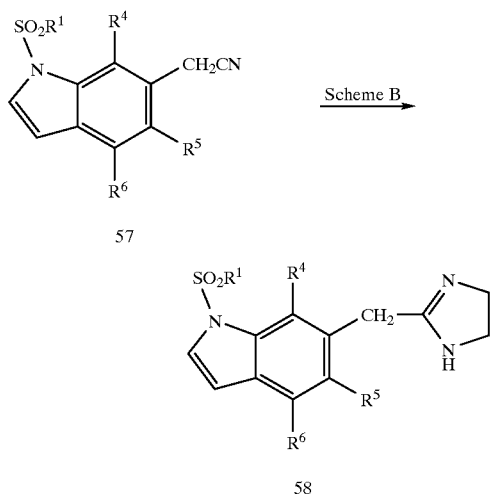

For those compounds wherein X is —NH— and Y is 2-imidazoline, compound 59 is reacted with $R^1SO_2V$ wherein V is halogen in the presence of strong base such as $NaN(TMS)_2$ (TMS=trimethylsilyl) to give compound 60. The latter compound is converted to compound 61 in the presence of a reducing agent such as hydrogen and platinum dioxide, hydrogen and palladium on carbon, iron in acetic acid, tin (II) chloride, titanium (III) chloride, and the like. Compound 62 can be produced from compound 61 by utilizing Scheme D above. The reaction scheme is set forth in Scheme N.

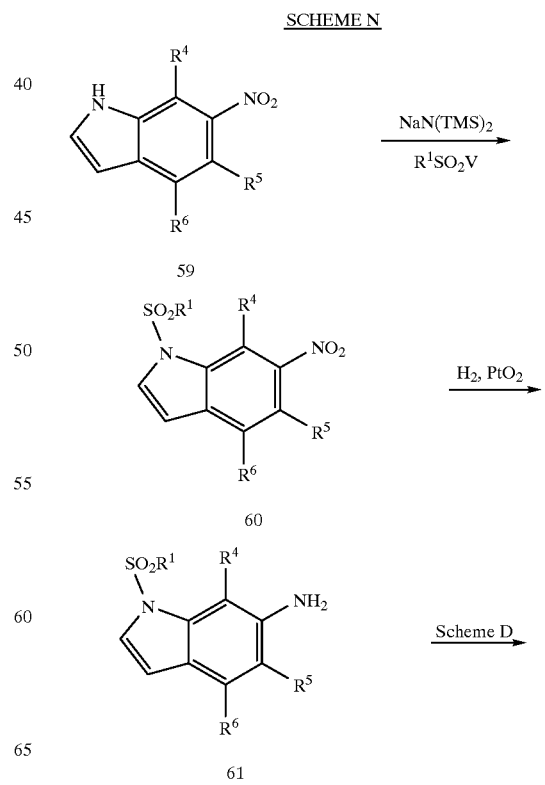

SCHEME N

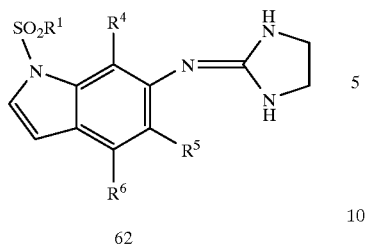

62

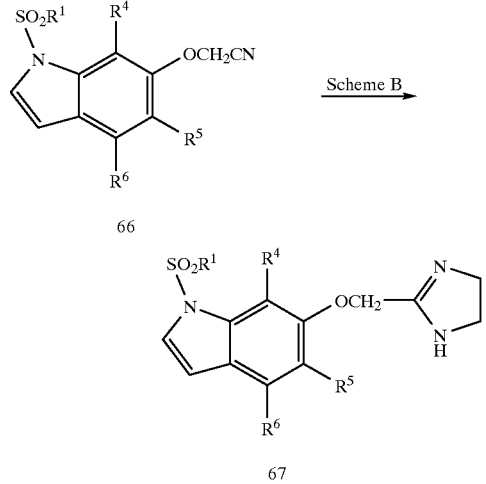

66

67

For those compounds wherein X is —OCH₂— and Y is 2-imidazoline, compound 63 is reacted with R¹SO₂V wherein V is halogen in the presence of strong base such as NaN(TMS)₂ (TMS=trimethylsilyl), LiN(TMS)₂, LDA (lithium diisopropylamide) LDA, NaH, and the like, to give compound 64. The latter compound is converted to compound 65 in the presence of a hydrolyzing agent such as pyridine (Pyr)•hydrochloride (Grates, et al., *JACS* (1963) 78:1380), TMSI (Jung, et al., *JOC* (1977) 42:3761), BBr₃, and so forth. Compound 66 can be produced from compound 65 by treatment with bromocyanomethane in the presence of a strong base such as NaN(TMS)₂, LiN(TMS)₂, LDA, NaH, and the like. Compound 67 is produced from compound 66 by utilizing Scheme B above. The reaction scheme is set forth in Scheme O. $R^{41}$ is lower alkyl, e.g., methyl.

The compounds of Formula 1 wherein X is —NH— and Y is 2-oxazoline or thiazoline can be made according the Scheme P. Scheme J is carried out to produce compound 70, which is combined with ClCH₂CH₂CNO to yield compound 71. Compound 71 is treated to cyclize and form the 2-oxazoline ring in compound 72. This may be carried out under conditions such as treatment with potassium fluoride and aluminum oxide in acetonitrile or heating an aqueous solution of compound 71. This type of reaction is described by Wang, et al., *Bioorganic and Medicinal Chemistry Letters* (1994) 19:2317. The reactions are summarized in Scheme P.

SCHEME O

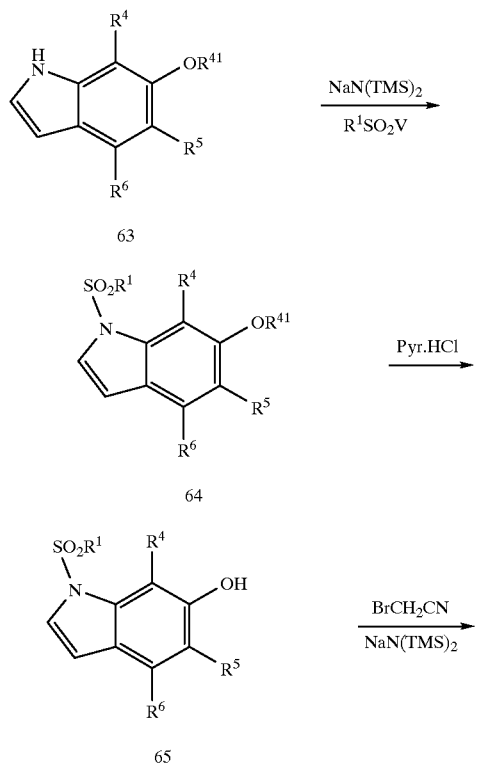

SCHEME P

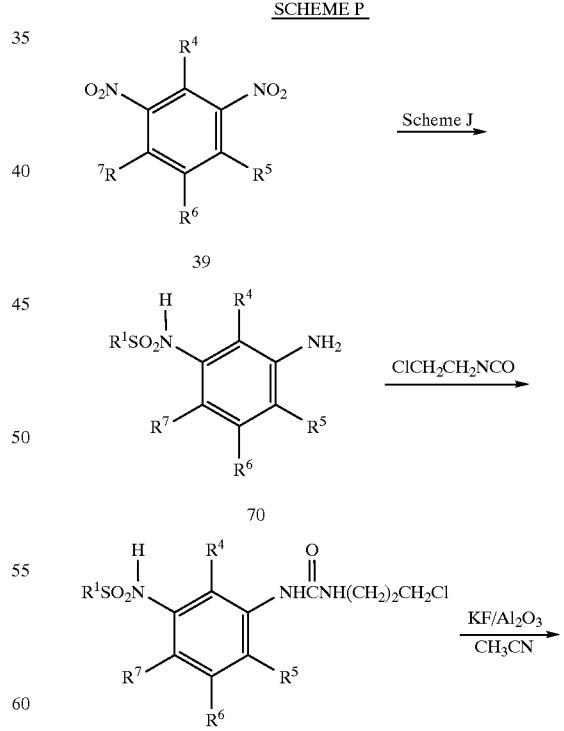

—OCH$_2$—, Y is 2-imidazoline, R$^4$ is CH$_3$, R$^5$ is H, R$^6$ is H, and R$^7$ is halo (preferably chloro, bromo, or iodo).

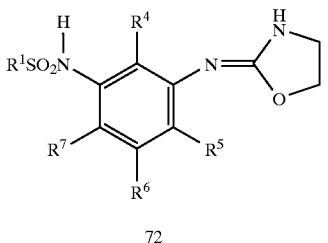

For those compounds wherein A is R$^1$R$^3$NCONR$^2$— and X is —CH$_2$— or —OCH$_2$—, the following illustrative Scheme R may be employed. The amine group in the precursor compound is reacted with the appropriate alkali met al cyanate, for example potassium cyanate, in an aqueous acid solution to form the urea group. Then, similarly following the procedures of Scheme B, the cyano group is transformed to an imidate functionality, which is condensed with 1,2-diaminoetane to form the 2-imidazoline group.

SCHEME R

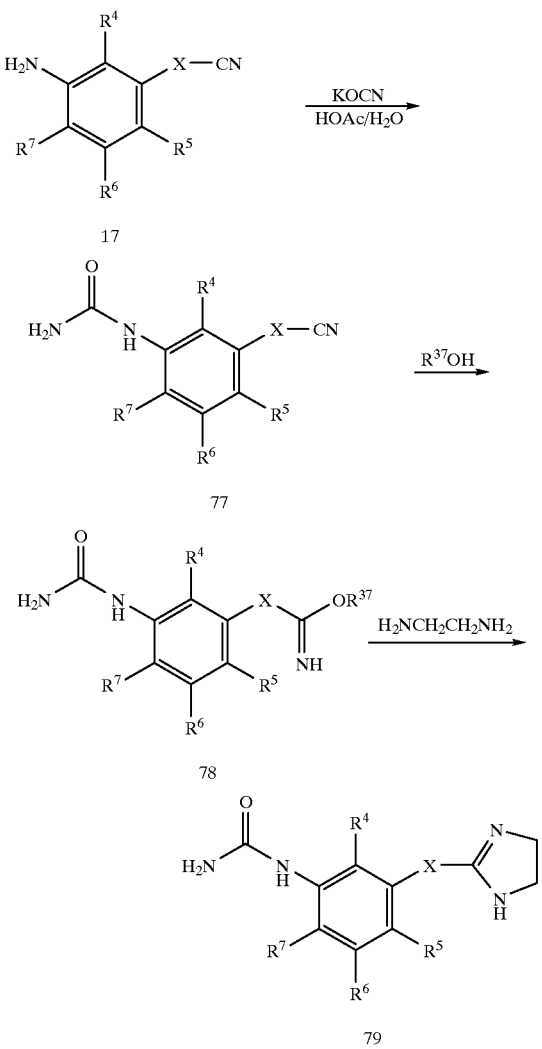

The following Scheme S may be used to synthesize compounds of the invention wherein A is CH$_3$SO$_2$NH, X is

SCHEME S

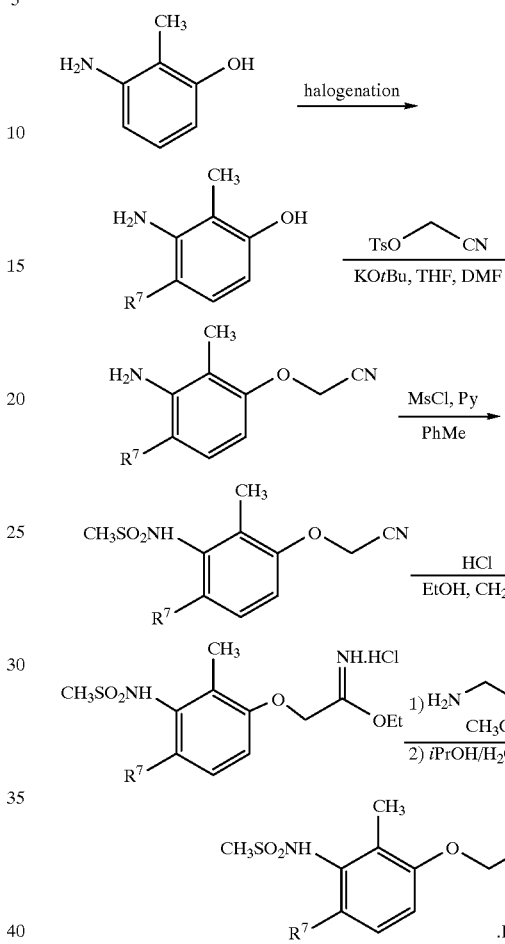

The desired product is obtained via 4-halo-3-amino-o-cresol, (2-methyl-3-amino-4-halophenoxy)acetonitrile, and N-(6-halo-3-cyanomethoxy-2-methylphenyl)-methanesulfonamide intermediates. To obtain the 4-halo-3-amino-o-cresol intermediate, halogenation of 3-amino-o-cresol is carried out using a source of positive halogen; for example, chlorine, e.g. N-chloro-succinimide, trichloroisocyanuric acid, t-butylhypochlorite, sulfuryl chloride, and the like, most preferably N-chlorosuccinimide. Halogenation is carried out in a strong anhydrous acid, e.g. methanesulfonic acid, sulfuric acid, trifluoroacetic acid, and the like, most preferably methanesulfonic acid, at a temperature of about 0–50° C., most preferably at a temperature of about 5–12° C. The halogenation reaction gives a mixture of the desired 4-halo-3-amino-o-cresol, the isomeric 6-halo-3-amino-o-cresol, and a small amount of 4,6-dihalo-3-amino-o-cresol. The desired intermediate is isolated by filtration after the reaction mixture is made basic with ammonium hydroxide solution at elevated temperature (about 50–80° C., most preferably about 50–60° C.). This may be accomplished by adding dilute ammonium hydroxide to the reaction mixture, or by adding the reaction mixture to dilute ammonium hydroxide or, preferably, by first adding the reaction mixture to water and then adding concentrated ammonium hydroxide. In any case, the exothermic nature of the dilution and neutralization of the acid causes the mixture to heat significantly. The 4-halo isomer is highly crystalline and significantly less soluble than the other products at elevated temperature, resulting in the selective crystallization of the desired intermediate, 4-halo-3-amino-o-cresol, in a purified state. If needed, further purification can be accomplished by recrystallization from aqueous isopropanol or toluene, or, preferably, by simply heating the intermediate to the boil in water and allowing the mixture to cool to room temperature, whereupon the purified intermediate is isolated by filtration.

The purified 4-halo-3-amino-o-cresol intermediate is then converted to a (2-methyl-3-amino-4-halophenoxy) acetonitrile intermediate, by first treating the cresol intermediate with a solution of alkali metal alkoxide, preferably potassium tert-butoxide, in a dipolar aprotic solvent such as tetrahydrofuran, N,N-dimethylformamide, N-methylpyrrolidinone, dimethysulfoxide, or a mixture thereof, and then reacting the cresol intermediate with cyanomethyl tosylate in a dipolar aprotic solvent such tetrahydrofuran, N,N-dimethylformamide, N-methylpyrrolidinone, dimethylsulfoxide, or a mixture thereof, at a temperature of about 20° C. The mixture is partitioned between organic (such as toluene or ethyl acetate) and water phases, and the aqueous phase extracted with an organic solvent such as toluene or ethyl acetate. The combined organics are washed with dilute NaOH and water, then concentrated.

The (2-methyl-3-amino-4-halophenoxy)acetonitrile intermediate is then converted to N-(6-halo-3-cyanomethoxy-2-methylphenyl)-methanesulfonamide. Methanesulfonyl chloride is added to a solution of the (2-methyl-3-amino-4-halophenoxy)acetonitrile in a solvent such as toluene or ethyl acetate and the mixture heated to about 40° C. Pyridine is then slowly added. The resultant mixture is cooled and stirred. The mixture is then partitioned between 1N hydrochloric acid, and a mixture of ethyl acetate and tetrahydrofuran. The organic phase is washed with water, then concentrated, leading to crystallization of N-(6-halo-3-cyanomethoxy-2-methylphenyl)-methanesulfonamide. This crystalline intermediate is collected, rinsed with an organic solvent such as toluene or ethyl acetate, and dried. This material could optionally be recrystallized from isopropanol.

Gaseous hydrogen chloride is bubbled through a suspension of the N-(6-halo-3-cyanomethoxy-2-methylphenyl)-methanesulfonamide intermediate in a mixture of dichloromethane and ethanol, keeping the temperature below about 15° C. The resultant mixture is stirred at ambient temperature, during which time the initially formed imidate ester hydrochloride precipitates. Excess hydrogen chloride is purged from the reaction vessel, and the resultant slurry was completely dissolved by the addition of methanol. This solution is then added to a solution of ethylene diamine in methanol, keeping the temperature below 25° C. The desired product salt, N-[6-halo-3-(4,5-dihydro- 1-H-imidazol-2-yl-methoxy-2-methylphenyl]-methanesulfonamide hydrochloride, precipitates from the reaction mixture and is purified by conventional techniques. This material may optionally be recrystallized from isopropanol/water.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be had by reference to the Examples hereinbelow. However, other equivalent separation or isolation procedures could, of course, also be used.

Specific Embodiments of Compounds in accordance with the Present Invention

One series of preferred compounds in accordance with the present invention includes compounds represented by Formula 3, or a pharmaceutically acceptable salt thereof:

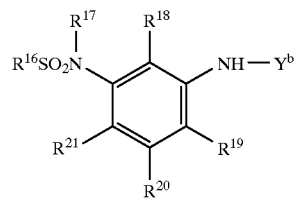

3 wherein $Y^b$ is 2-imidazoline, and

| $R^{16}$ | $R^{17}$ | $R^{18}$ | $R^{19}$ | $R^{20}$ | $R^{21}$ |
|---|---|---|---|---|---|
| $CH_3$ | H | H | H | H | H |
| (N-[3-(imidazolidin-2-ylideneamino)-phenyl]-methanesulfonamide) | | | | | |
| $CH_3$ | H | $CH_3$ | H | H | H |
| (N-[3-(imidazolidin-2-ylideneamino)-2-methyl-phenyl]-methanesulfonamide) | | | | | |
| $CH_3$ | H | H | H | H | $CH_3$ |
| (N-[5-(imidazolidin-2-ylideneamino)-2-methyl-phenyl]-methanesulfonamide) | | | | | |
| $CH_3$ | H | $CH_3$ | H | Cl | H |
| (N-[5-chloro-3-(imidazolidin-2-ylideneamino)-2-methyl-phenyl]-methanesulfonamide) | | | | | |
| $CH_3$ | H | H | H | H | Cl |
| (N-[2-chloro-5-(imidazolidin-2-ylideneamino)]-methanesulfonamide) | | | | | |
| $CH_3$ | H | $CH_3$ | H | Br | H |
| (N-[5-bromo-3-(imidazolidin-2-ylideneamino)-2-methyl-phenyl]-methanesulfonamide) | | | | | |
| $CH_3$ | H | $CH_3$ | H | $CH_3$ | H |
| (N-[3-(imidazolidin-2-ylideneamino)-2,5-dimethyl-phenyl]-methanesulfonamide) | | | | | |
| $CH_3$ | H | H | H | $OCH_3$ | H |
| (N-[3-(imidazolidin-2-ylideneamino)-5-methoxy-phenyl]-methanesulfonamide) | | | | | |
| $CH_3$ | H | $CH_3$ | H | $CH(CH_3)_2$ | H |
| (N-[3-(imidazolidin-2-ylideneamino)-5-isopropyl-2-methyl-phenyl]-methanesulfonamide) | | | | | |
| $CH_3$ | H | H | H | $CH_3$ | $CH_3$ |
| (N-[5-(imidazolidin-2-ylideneamino)-2,3-dimethyl-phenyl]-methanesulfonamide) | | | | | |
| $CH_3$ | H | H | H | Cl | H |
| (N-'3-chloro-5-(imidazolidin-2-ylideneamino)-phenyl]-methanesulfonamide) | | | | | |
| $CH_3$ | H | H | H | $CH_3$ | H |
| (N-[5-(imidazolidin-2-ylideneamino)-3-methyl-phenyl]-methanesulfonamide) | | | | | |
| $CH_3$ | H | $CH_3$ | H | H | $CH_3$ |
| (N-[3-(imidazolidin-2-ylideneamino)-2,6-dimethyl-phenyl]-methanesulfonamide) | | | | | |

Another series of preferred compounds in accordance with the present invention includes compounds represented by Formula 4, or a pharmaceutically acceptable salt thereof:

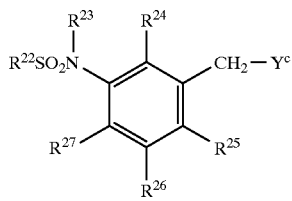

4 wherein $Y^c$ is 2-imidazoline, and

| $R^{22}$ | $R^{23}$ | $R^{24}$ | $R^{25}$ | $R^{26}$ | $R^{27}$ |
|---|---|---|---|---|---|
| CH$_3$ | H | CH$_3$ | H | H | H |
| (N-[3-(4,5-dihydro-1H-imidazol-2-ylmethyl)-2-methyl-phenyl]-methanesulfonamide) | | | | | |
| CH$_3$ | H | H | H | H | CH$_3$ |
| (N-[5-(4,5-dihydro-1H-imidazol-2-ylmethyl)-2-methyl-phenyl]-methanesulfonamide) | | | | | |
| CH$_3$ | H | H | H | Cl | CH$_3$ |
| N-[3-chloro-5-(4,5-dihydro-1H-imidazol-2-ylmethyl)-2-methyl-phenyl]-methanesulfonamide | | | | | |
| CH$_3$ | H | H | H | Br | CH$_3$ |
| (N-[3-bromo-5-(4,5-dihydro-1H-imidazol-2-ylmethyl)-2-methyl-phenyl]-methanesulfonamide) | | | | | |
| CH$_3$ | H | H | H | H | OCH$_3$ |
| (N-[5-(4,5-dihydro-1H-imidazol-2-ylmethyl)-2-methoxy-phenyl]-methanesulfonamide) | | | | | |
| CH$_3$ | H | H | H | H | H |
| (N-[3-(4,5-dihydro-1H-imidazol-2-ylmethyl)-phenyl]-methanesulfonamide) | | | | | |
| CH$_3$ | H | H | H | H | OH |
| (N-[5-(4,5-dihydro-1H-imidazol-2-ylmethyl)-2-hydroxy-phenyl]-methanesulfonamide) | | | | | |
| CH$_3$ | H | H | F | H | H |
| (N-[3-(4,5-dihydro-1H-imidazol-2-ylmethyl)-4-fluoro-phenyl]-methanesulfonamide) | | | | | |
| CH$_3$ | CH$_3$ | CH$_3$ | H | H | H |
| (N-[3-(4,5-dihydro-1H-imidazol-2-ylmethyl)-2-methyl-phenyl]-#N!-methyl-methanesulfonamide) | | | | | |
| CH$_3$ | H | Cl | H | H | H |
| (N-[2-chloro-3-(4,5-dihydro-1H-imidazol-2-ylmethyl)-phenyl]-methanesulfonamide) | | | | | |
| CH$_3$ | H | C$_6$H$_5$ | H | H | H |
| (N-[6-(4,5-dihydro-1H-imidazol-2-ylmethyl)-biphenyl-2-yl]-methanesulfonamide) | | | | | |
| CH$_3$ | H | CH$_3$ | CH$_3$ | H | H |
| (N-[3-(4,5-dihydro-1H-imidazol-2-ylmethyl)-2,4-dimethyl-phenyl]-methanesulfonamide) | | | | | |
| CH$_3$ | H | H | H | H | F |
| (N-[5-(4,5-dihydro-1H-imidazol-2-ylmethyl)-2-fluoro-phenyl]-methanesulfonamide) | | | | | |
| CH$_3$ | H | CH$_3$ | H | H | CH$_3$ |
| (N-[3-(4,5-dihydro-1H-imidazol-2-ylmethyl)-2,6-dimethyl-phenyl]-methanesulfonamide) | | | | | |
| CH$_3$ | H | CH$_3$ | H | CH$_3$ | H |
| (N-[3-(4,5-dihydro-1H-imidazol-2-ylmethyl)-2,6-dimethyl-phenyl]-methanesulfonamide) | | | | | |
| CH$_3$ | H | CH=CH$_2$ | H | H | H |
| (N-[3-(3H-imidazol-4-ylmethyl)-2-methyl-phenyl]-methanesulfonamide) | | | | | |
| CH$_3$ | H | C$_2$H$_5$ | H | H | H |
| (N-[3-(4,5-dihydro-1H-imidazol-2-ylmethyl)-2-ethyl-phenyl]-methanesulfonamide) | | | | | |
| CH$_3$ | H | H | H | CH$_3$ | H |
| (N-[3-(4,5-dihydro-1H-imidazol-2-ylmethyl)-5-methyl-phenyl]-methanesulfonamide) | | | | | |
| CH$_3$ | H | H | H | Br | H |
| (N-[3-bromo-5-(4,5-dihydro-1H-imidazol-2-ylmethyl)-phenyl]-methanesulfonamide) | | | | | |
| CH$_3$ | H | H | H | H | Cl |
| (N-[2-chloro-5-(4,5-dihydro-1H-imidazol-2-ylmethyl)-phenyl]-methanesulfonamide) | | | | | |
| CH$_3$ | H | H | H | CH$_3$ | CH$_3$ |
| (N-[3-(imidazolidin-2-ylideneamino)-5-isopropyl-2-methyl-phenyl]- | | | | | |

-continued

| $R^{22}$ | $R^{23}$ | $R^{24}$ | $R^{25}$ | $R^{26}$ | $R^{27}$ |
|---|---|---|---|---|---|
| methanesulfonamid) | | | | | |
| CH$_3$ | H | H | H | OCH$_3$ | H |
| (N-[3-(4,5-dihydro-1H-imidazol-2-ylmethyl)-5-methoxy-phenyl]-methanesulfonamide) | | | | | |
| CH$_3$CH$_2$ | H | H | H | H | CH$_3$ |
| (ethanesulfonic acid[5-(4,5-dihydro-1H-imidazol-2-ylmethyl)-2-methyl-phenyl)-amide) | | | | | |
| CH$_3$ | H | OCH$_3$ | H | H | H |
| (N-[3–4,5-dihyro-1H-imidazol-2-ylmethyl)-2-methoxy-phenyl]-methanesulfonamide) | | | | | | and wherein $Y^c$ is 4-imidazole, and

| $R^{22}$ | $R^{23}$ | $R^{24}$ | $R^{25}$ | $R^{26}$ | $R^{27}$ |
|---|---|---|---|---|---|
| CH$_3$ | H | CH$_3$ | H | H | H |
| (N-[3-(3H-imidazol-4-ylmethyl)-2-methyl-phenyl]-methanesulfonamide | | | | | |
| CH$_3$ | H | CH$_3$ | H | CH$_3$ | H |
| (N-[3-(3H-imidazol-4-ylmethyl)-2,5-dimethyl-phenyl]-methanesulfonamide) | | | | | |
| CH$_3$ | H | H | H | H | CH$_3$ |
| (N-[5-(3H-imidazo-4-ylmethyl)-2-methyl-phenyl]-methanesulfonamide) | | | | | |

Another series of preferred compounds in accordance with the present invention includes compounds represented by Formula 5, or a pharmaceutically acceptable salt thereof:

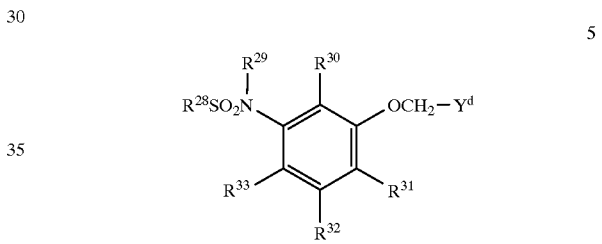

5 wherein $Y^d$ is 2-imidazoline, and

| $R^{28}$ | $R^{29}$ | $R^{30}$ | $R^{31}$ | $R^{32}$ | $R^{33}$ |
|---|---|---|---|---|---|
| CH$_3$ | H | H | H | H | H |
| (N-[3-(4,5-dihydro-1H-imidazol-2-ylmethoxy)phenyl]-methanesulfonamide) | | | | | |
| CH$_3$ | H | H | H | H | F |
| (N-[5-(4,5-dihydro-1H-imidazol-2-ylmethoxy)-2-fluoro-phenyl]-methanesulfonamide) | | | | | |
| CH$_3$ | H | H | H | H | CH$_3$ |
| (N-[5-(4,5-dihydro-1H-imidazol-2-ylmethoxy)-2-methyl-phenyl]-methanesulfonamide) | | | | | |
| CH$_3$ | H | H | H | H | Cl |
| (N-[5-(4,5-dihydro-1H-imidazol-2ylmethoxy)-2-chloro-phenyl]-methanesulfonamide) | | | | | |
| C$_2$H$_5$ | H | H | H | H | H |
| (ethanesulfonic acid [3-(4,5-dihydro-1H-imidazol-2-ylmethoxy)-phenyl]-amide) | | | | | |
| C$_3$H$_7$ | H | H | H | H | H |
| (propane-1-sulfonic acid [3-(4,5-dihydro-1H-imidazol-2-ylmethoxy)-phenyl]-amide) | | | | | |
| C$_6$H$_5$ | H | H | H | H | H |
| (N-[3-(4,5-dihydro-1H-imidzol-2-ylmethoxy)-phenyl]-benzenesulfonamide) | | | | | |
| CH$_3$ | H | H | H | H | OH |
| (N-[5-(4,5-dihydro-1H-imidazol-2ylmethoxy)-2-hydroxy-hydroxy-phenyl]-methanesulfonamide) | | | | | |
| CH$_3$ | H | CH$_3$ | H | H | H |
| (N-[3-(4,5-dihydro-1H-imidazol-2-ylmethoxy)-2-methyl-phenyl]-methanesulfonamide) | | | | | |

-continued

| $R^{28}$ | $R^{29}$ | $R^{30}$ | $R^{31}$ | $R^{32}$ | $R^{33}$ |
|---|---|---|---|---|---|
| CH$_3$ | H | H | CH$_3$ | H | H |
| (N-[3-(4,5-dihydro-1H-imidazol-2-ylmethoxy)-4-methyl-phenyl]-methanesulfonamide) | | | | | |
| CH$_3$ | H | H | CH$_3$ | H | CH$_3$ |
| (N-[5-(4,5-dihydro-1H-imidazol-2-ylmethoxy)-2,4-dimethyl-phenyl]-methanesulfonamide) | | | | | |
| CH$_3$ | H | CH$_3$ | H | H | CH$_3$ |
| (N-[3-(4,5-dihydro-1H-imidazol-2-ylmethoxy)-2,6-dimethyl-phenyl]-methanesulfonamide) | | | | | |
| CH$_3$ | H | CH$_3$ | H | H | Cl |
| (N-[6-chloro-3-(4,5-dihydro-1H-imidazol-2-ylmethoxy)-2-methyl-phenyl]-methanesulfonamide) | | | | | |
| CH$_3$ | H | CH$_3$ | H | H | Br |
| (N-[6-bromo-3-(4,5-dihydro-1H-imidazol-2-ylmethoxy)-2-methyl-phenyl]-methanesulfonamide) | | | | | |
| CH$_3$ | H | H | H | F | H |
| (N-[3-fluoro-5-(4,5-dihydro-1H-imidazol-2-ylmethoxy)-phenyl]-methanesulfonamide) | | | | | |
| CH$_3$ | H | H | H | Cl | H |
| (N-[3-chloro-5-(4,5-dihydro-1H-imidazol-2-ylmethoxy)-phenyl]-methanesulfonamide) | | | | | |
| H | H | CH$_3$ | H | H | Br |
| (N-[6-bromo-3-(4,5-dihydro-1H-imidazol-2-ylmethoxy)-2-methyl-phenyl]-methanesulfonamide) | | | | | |
| CH$_3$ | H | CH$_3$ | H | Cl | H |
| (N-[5-chloro-3-(4,5-dihydro-1H-imidazol-2-ylmethoxy)-2-methyl-phenyl]-methanesulfonamide) | | | | | |
| CH$_3$ | H | H | H | CH$_3$ | H |
| (N-[3-(4,5-dihydro-1H-imidazol-2-ylmethoxy)-5-methyl-phenyl]-methanesulfonamide) | | | | | | and wherein $Y^d$ is 4-imidazole, and

| $R^{28}$ | $R^{29}$ | $R^{30}$ | $R^{31}$ | $R^{32}$ | $R^{33}$ |
|---|---|---|---|---|---|
| CH$_3$ | H | H | H | H | H |
| (N-[3-(1H-imidazol-4(5)-ylmethoxy)-phenyl]methanesulfonamide) | | | | | |
| CH$_3$ | H | H | H | H | F |
| (N-[2-fluoro-5-(1H-imidazol-4(5)-ylmethoxy)-phenyl]-methanesulfonamide) | | | | | |
| CH$_3$ | H | H | H | H | Cl |
| (N-[2-chloro-5-(1H-imidazol-4(5)-ylmethoxy)-phenyl]-methanesulfonamide) | | | | | |
| CH$_3$ | H | CH$_3$ | H | H | Cl |
| (N-[6-chloro-3-(3H-imidazol-4(5)-ylmethoxy)-2-methyl-phenyl]methanesulfonamide) | | | | | |
| CH$_3$ | H | H | H | H | CH$_3$ |
| (N-[2-methyl-5-(1H-imidazol-4(5)-ylmethoxy)-phenyl]-methanesulfonamide) | | | | | |

Preferred compounds also include the following compounds, or the equivalent free base, or the pharmaceutically acceptable salts thereof:

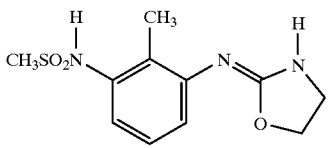

N-[2-methyl-3-(oxazolidin-2-ylideneamino)-phenyl]-methanesulfonamide;

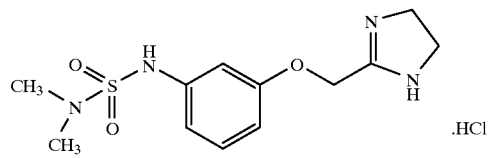

N,N-dimethyl-N'-[3-(4,5-dihydro-1H-imidazol-2-ylmethoxy)phenyl]-sulfamide hydrochloride;

N-methanesulfonyl-6-(4,5-dihydro-1H-imidazol-2-ylmethyl)indole hydrochloride;

wherein Me = CH$_3$

N-methanesulfonyl-6-(imidazolidin-2-ylideneamino)indole hydrochloride;

wherein Me = CH$_3$ 6-(Imidazolidin-2-ylideneamino)indole-1-sulfonic acid dimethylamide hydrochloride;

wherein Me = CH$_3$

Imidazolidin-2-ylidene-[1-(propane-1-sulfonyl)-1H-indol-6-yl]-amine;

wherein Pr = propyl 6-(4,5-dihydro-1H-imidazol-2-ylmethoxy)-1-methanesulfonyl-1H-indole;

wherein Ms = SO$_2$CH$_3$

Imidazolidin-2-ylidene-(1-methanesulfonyl-3-bromo-1H-indol-6-yl)-amine hydrochloride;

wherein Ms = SO$_2$CH$_3$

Imidazolidin-2-ylidene-(1-methanesulfonyl-3-methyl-1H-indol-6-yl)-amine hydrochloride;

wherein Ms = SO$_2$CH$_3$

-continued

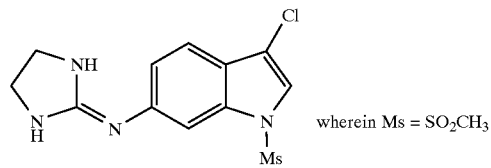

wherein Ms = SO$_2$CH$_3$

Imidazolidin-2-ylidene-(1-methanesulfonyl-3-bromo-1H-indol-6-yl)-amine hydrochloride;

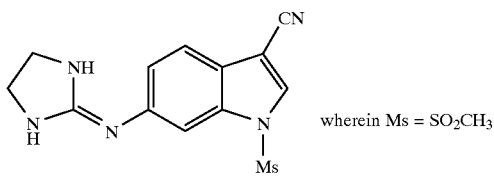

wherein Ms = SO$_2$CH$_3$

Imidazolidin-2-ylidene-(1-methanesulfonyl-3-cyano-1H-indol-6-yl)-amine hydrochloride.

Preferred Processes

In summary, illustrative compounds represented by Formula 1 are prepared according to the following last steps:

1. A process for preparing compounds of Formula 1 wherein A is R$^1$SO$_2$NH—, X is —CH$_2$— or —OCH$_2$—, and Y is 2-imidazoline comprises reacting a compound of the formula:

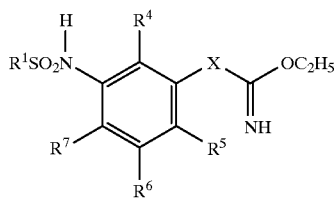

with 1,2-diaminoethane.

2. Alternatively, a process for preparing compounds of Formula 1 wherein A is R$^1$SO$_2$NH—, X is —CH$_2$—, and Y is 4-imidazole comprises reacting a compound of the formula:

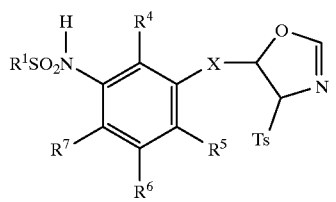

with ammonia.

3. Alternatively, a process for preparing compounds of Formula 1 wherein A is R$^1$SO$_2$NH—, X is —CH$_2$— or —OCH$_2$—, and Y is 4-imidazole comprises reacting a compound of the formula:

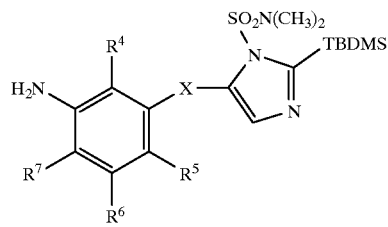

with dilute inorganic acid.

4. Alternatively, a process for preparing compounds of Formula 1 wherein A is R$_1$SO$_2$NH—, X is —OCH$_2$—, and Y is 4-imidazole comprises reacting a compound of the formula:

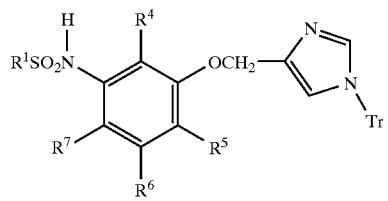

with dilute inorganic acid such as hydrochloric acid in an inert organic solvent such as acetonitrile.

5. Alternatively, a process for preparing compounds of Formula 1 wherein A is R$^1$SO$_2$NH—, X is —NH—, and Y is 2-imidazoline comprises reacting a compound of the formula:

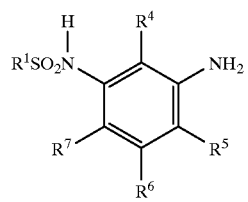

with 2-chloroimidazoline.

6. Alternatively, a process for preparing compounds of Formula 1 wherein R$^2$ and R$^7$ may be taken together to form alkylene or alkenylene of 2 to 3 carbon atoms in a 5- or 6-membered ring comprises reacting a compound of the formula:

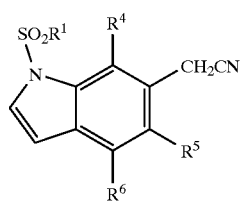

to convert the cyano group to an imidate functionality, which is condensed with 1,2-diaminoethane to form the 2-imidazoline group.

7. Alternatively, a process for preparing compounds of Formula 1 wherein X is —NH— and Y is 2-imidazoline comprises reacting a compound of the formula:

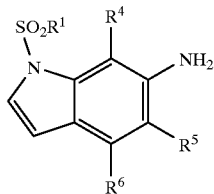

with 2-haloimidazoline to produce the desired compound directly.

8. Alternatively, a process for preparing compounds of Formula 1 wherein X is —OCH$_2$— and Y is 2-imidazoline comprises reacting a compound of the formula:

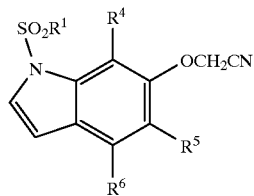

with 1,2-diaminoethane to form the 2-imidazoline group.

9. Alternatively, a process for preparing compounds of Formula 1 wherein X is —NH— and Y is 2-oxazoline or thiazoline comprises reacting a compound of the formula:

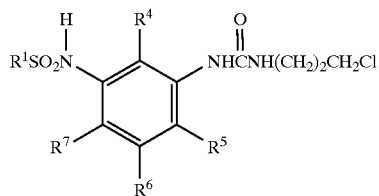

with potassium fluoride and aluminum oxide in acetonitrile or heating an aqueous solution of compound 71.

10. Alternatively, a process for preparing compounds of Formula 1 wherein A is R$^1$SO$_2$NH, X is —CH$_2$— or —OCH$_2$—, and Y is 2-imidazoline comprises reacting a compound of the formula:

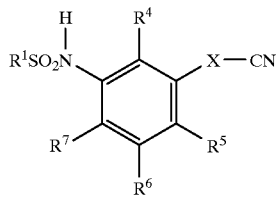

with ethylene diamine and trimethylaluminum.

Salts of Compounds of the Present Invention

The compounds of Formula 1 may be converted to a corresponding acid addition salt by virtue of the presence of the tertiary nitrogen atoms.

The conversion is accomplished by treatment with at least a stoichiometric amount of an appropriate acid, such as mineral acids, e.g., hydrochloric acid, hydrobromic acid, sulfuric acid, nitric acid, phosphoric acid, and the like, and organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Typically, the free base is dissolved in an inert organic solvent such as diethyl ether, ethyl acetate, chloroform, ethanol, methanol, and the like, and the acid added in a similar solvent. The temperature is maintained at about 0 to 50° C. The resulting salt precipitates spontaneously or may be brought out of solution with a less polar solvent.

The acid addition salts of the compounds of Formula 1 may be converted to the corresponding free bases by treatment with at least a stoichiometric amount of a suitable base such as sodium or potassium hydroxide, potassium carbonate, sodium bicarbonate, ammonia, and the like.

Utility and Administration:

General Utility

The compounds of Formula 1 and the pharmaceutically acceptable acid addition salts thereof have been found to possess valuable pharmacological properties and, in particular, have been shown to be selective alpha$_{1A/1L}$-adrenoceptor agonists in standard laboratory tests. Accordingly, these compounds and pharmaceutically acceptable compositions containing them are useful in the regulation of physiological phenomena related to alpha$_{1A/1L}$-adrenoceptor agonists, such as the treatment of urinary incontinence (without the adverse side effects on blood pressure in mammals), nasal congestion, priapism, depression, anxiety, dementia, senility, Alzheimer's, deficiencies in attentiveness and cognition, and eating disorders such as obesity, bulimia, and anorexia.

Testing

General Strategy for Identifying Alpha$_{1A/1L}$-adrenoceptor Agonists:

In Vitro:

Potential for alpha$_{1A/1L}$-adrenoceptor agonist activity was determined in vitro by evaluating the potency and relative intrinsic activity (relative to norepinephrine or phenylephrine) of standard and novel compounds to contract isolated rabbit bladder neck strips (alpha$_{1A/1L}$-adrenoceptor) and isolated rat aortic rings (alpha$_{1D}$-adrenoceptor), as hereinafter described in Example 18.

In Vivo:

Standard and novel compounds which selectively contracted rabbit bladder neck strips were subsequently evaluated in vivo in anesthetized female micropigs to assess urethral activity relative to diastolic blood pressure effects. Compounds with the desired activity in anesthetized pigs were evaluated in conscious female micropigs instrumented with telemetry to measure diastolic blood pressure and a strain-gage transducer to measure urethral tension, as hereinafter described in Example 18.

General Administration

In applying the compounds of the present invention to treatment of the above disease states, administration of the active compounds and salts described herein can be via any of the accepted modes of administration for alpha-adrenoceptor agonists. Any pharmaceutically acceptable mode of administration, whether enteral or parenteral, can be used, and dosage forms may include any appropriate solid, semi-solid, liquid, vaporized, or gaseous dosage forms, such as, for example, tablets, suppositories, pills, capsules, powders, liquids, solutions, elixirs, suspensions, emulsions, aerosols, sprays, and the like, preferably in unit dosage forms suitable for single or multiple administration of precise dosages, or in sustained or controlled release dosage forms for the prolonged administration of the compound at a predetermined rate. While it is possible that, for use in therapy, a compound of the present invention may be administered as the raw chemical compound, it is generally preferable to present the compound as an active ingredient in a pharmaceutical composition or formulation. The amount of active compound administered will of course, be dependent on the condition being treated, the subject being treated, the severity of the affliction, the manner of administration, and the judgment of the prescribing physician, medical professional, or veterinarian. However, an effective dosage is typically in the range of 0.15 to 1.5 mg/kg/day, preferably 0.35 to 0.70 mg/kg/day. For an average 70 kg human, this would amount to 10 to 100 mg per day, or preferably 25 to 50 mg/day.

The invention thus further provides a pharmaceutical composition or formulation comprising a compound of the invention or a pharmaceutically acceptable salt or derivative thereof together with one or more pharmaceutically acceptable carriers therefore and, optionally, other therapeutic and/or prophylactic ingredients. The carrier(s) must be "acceptable" in the sense of being compatible with the other ingredients of the composition or formulation and not deleterious to the recipient thereof. The compositions will typically include a conventional pharmaceutical carrier or excipient and an active compound of Formula 1 or the pharmaceutically acceptable salts thereof and, in addition, may include other medicinal agents, pharmaceutical agents, carriers, adjuvants, and the like.

Pharmaceutical compositions or formulations include those suitable for oral, nasal, pulmonary, topical (including buccal and sub-lingual), rectal, vaginal, or parenteral (including intrathecal, intraarterial, intramuscular, sucutaneous, and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration, or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is a mixture with the finely divided active component.

In tablets, the active component is mixed with the carrier having the necessary binding capacity in suitable proportions and compacted in the shape and size desired.

The powders and tablets preferably contain from 0.5 percent to 95 percent of the active compound. Suitable carriers include magnesium carbonate, magnesium stearate, talc, sugar, glucose, sucrose, lactose, pectin, dextrin, starch, gelatin, mannitol, cellulose, methylcellulose, sodium carboxymethylcellulose, sodium saccharin, sodium crosscarmellose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be as solid forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify. Polyalkylene glycols, for example proplyene glycol, may also be used as the carrier.

Formulations suitable for vaginal administration may be presented as pessaries, tampons, creams, gels, pastes, foams, or sprays containing in addition to the active ingredient such carriers as are known in the art to be appropriate.

Liquid form preparations include solutions, suspensions, and emulsions; suitable carriers include, for example, water, saline, aqueous dextrose, glycerol, ethanol, and the like.

The compounds according to the present invention may thus be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g., sterile, pyrogen-free water, before use.

Aqueous solutions suitable for oral use can be prepared by dissolving the active component in water and adding suitable colorants, flavors, stabilizing, and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis, the compounds according to the invention may be formulated as ointments, creams, or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions, emulsions, or suspensions are applied directly to the nasal cavity by conventional means, for example with a dropper, pipette, or sprayer. The formulations may be provided in a single or multidose form. In the latter case of a dropper or pipette, this may be achieved by the patient administering an appropriate, predetermined volume of the solution or suspension. In the case of a sprayer, this may be achieved for example by means of a metering atomizing spray pump. Suitable liquid media include water, propylene glycol, and other pharmaceutically acceptable alcohols, and sesame or peanut oil, and other pharmaceutically acceptable vegetable oils. Generally the active compound is administered as an aqueous solution spray of from 0.0001 to 1.0, preferably of from 0.025 to 0.10, percent concentration.

Administration to the respiratory tract may also be achieved by means of an aerosol formulation in which the active ingredient is provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in a form of a dry powder, for example a powder mix of the compound in a suitable powder base such as lactose, starch, starch derivatives such as hydroxypropylmethyl cellulose, and polyvinylpyrrolidine (PVP). Conveniently the powder carrier will form a gel in the nasal cavity. The powder composition may be presented in unit dose form for example in capsules or cartridges of e.g., gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

The pharmaceutical compositions or formulations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. Actual methods of preparing such dosage forms are known, or will be apparent, to those skilled in the art; for example, see *Remington's Pharmaceutical Sciences*, Mack Publishing Company, Easton, Pa., 16th Edition, 1980.

EXAMPLES

The invention is demonstrated further by the following illustrative examples. Parts and percentages are by weight unless otherwise specified. Temperatures are in degrees Centigrade unless specified otherwise. Unless indicated otherwise, all reagents are from Aldrich Chemical Company, Milwaukee, Wis. The following preparations and examples illustrate the invention but are not intended to limit its scope.

Example 1

Preparation of N-[3-(4,5-dihydro-1H-imidazol-2-ylmethoxy)phenyl]-methanesulfonamide hydrochloride

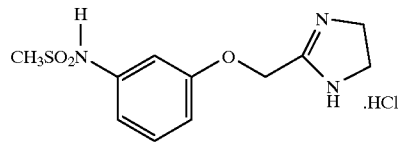

N-[3-(4,5-dihydro-1H-imidazol-2-ylmethoxy)phenyl]-methanesulfonamide hydrochloride

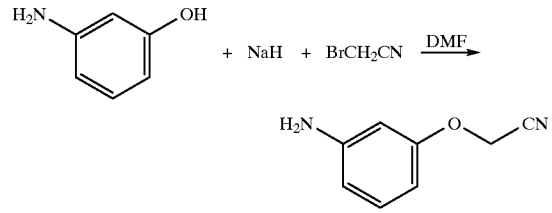

Sodium hydride (3.5 g, 60%) in mineral oil was rinsed with hexane to remove the oil and then suspended in 40 ml of N,N-dimethylformamide (DMF). The mixture was cooled in an ice bath and then treated dropwise with a solution of 8.0 g of 3-aminophenol in 40 ml of N,N-dimethylformamide. After addition of the 3-aminophenol, the ice bath was removed and the reaction mixture was stirred at room temperature for 14 hours. The mixture was again cooled in an ice bath and treated with 9.2 g of bromoacetonitrile. The ice bath was removed and the reaction mixture was stirred at room temperature for 1 hour. The mixture was poured into ether, washed with water, dried, and evaporated to give 5.8 g of (3-aminophenoxy)-acetonitrile as a dark oil.

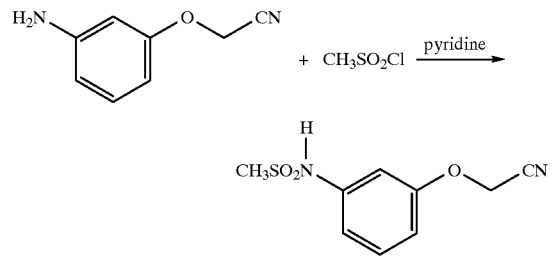

(3-Aminophenoxy)-acetonitrile (3.0 g) was dissolved in 12 ml of pyridine, cooled in an ice bath, treated with 3.47 g of methanesulfonyl chloride, and stirred at room temperature for 3 hours. The mixture was poured into ethyl acetate, washed with hydrochloric acid, then with water, dried, and evaporated. The residue was purified by silica gel chromatography eluting with ethyl acetate:hexane (3:7) giving 3.0 g of N-(3-cyanomethoxyphenyl)-methanesulfonamide. An aliquot of this product was crystallized from ethyl acetate-:hexane (3:7) to give a solid, mp 91–92° C.

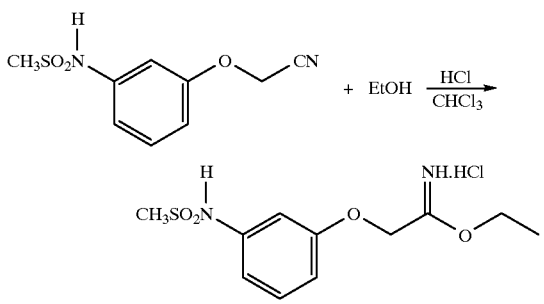

N-(3-Cyanomethoxyphenyl)-methanesulfonamide (1.0 g) was dissolved in a mixture of 20 ml of chloroform and 0.25 ml of absolute ethanol (EtOH). The reaction mixture was cooled in an ice bath and saturated with hydrogen chloride gas. The mixture was slowly allowed to come to room temperature and stirred for 16 hours. The solvent was evaporated leaving 1.1 g of 2-(3-methanesulfonylaminophenoxy)-acetimidic acid ethyl ester hydrochloride.

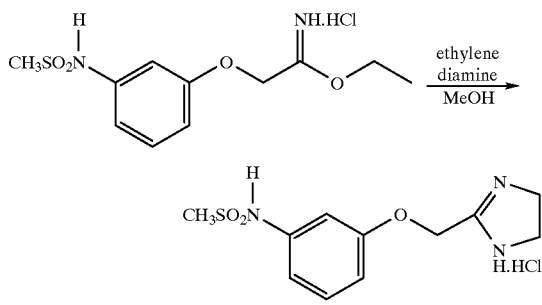

2-(3-Methanesulfonylaminophenoxy)-acetimidic acid ethyl ester hydrochloride (0.8 g) was suspended in 12 ml of absolute methanol (MeOH) and treated with 0.16 g of ethylene diamine. After 8 hours at room temperature the solvent was evaporated. The residue was purified by silica gel chromatography eluting with methanol:dichloromethane:ammonium hydroxide (16:84:0.1). Conversion to the hydrochloride salt by addition of 1.0M hydrogen chloride in ether gave 0.16 g of N-[3-(4,5-dihydro-1H-imidazol-2-ylmethoxy)phenyl]methanesulfonamide hydrochloride, mp 183–187° C.

Example 1A

Preparation of N-[3-(4,5-dihydro-1H-imidazol-2-ylmethoxy)phenyl]-methanesulfonamide hydrochloride monohydrate 1. Preparation of (3-aminophenoxy)acetonitrile

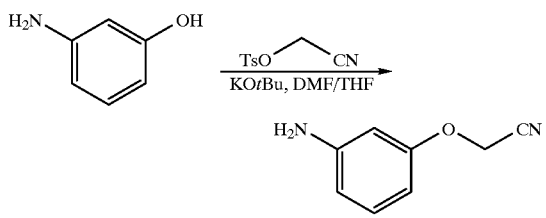

To a solution of potassium tert-butoxide (9.8 g) in 40 mL tetrahydrofuran/12 mL N,N-dimethylformamide was added a solution of 3-aminophenol (10.0 g) in 16 mL tetrahydrofuran/4 mL N,N-dimethylformamide at a rate such that the reaction temperature did not exceed 25° C. After 30 min, a solution of cyanomethyl tosylate (17.5 g) in 12 mL tetrahydrofuran/4 mL N,N-dimethylformamide was slowly added to the phenoxide solution, keeping the temperature at or below 25° C. The resultant slurry was stirred for 3 h, at which point TLC analysis indicated complete reaction. The crude mixture was partitioned between toluene (200 mL) and water (200 mL), and the aqueous phase was extracted with a 100 mL portion of toluene. The combined organics were washed with 1N NaOH and water, then concentrated to an oil (16.0 g). The crude product was typically carried directly into the next step without purification.

2. Preparation of N-(3-cyanomethoxyphenyl)methanesulfonamide

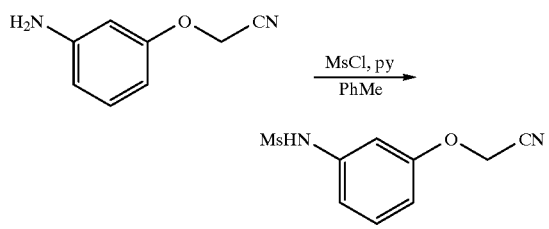

To a solution of crude (3-aminophenoxy)acetonitrile (ca 12.1 g) in toluene (50 mL) was added pyridine (6.6 mL) and methanesulfonyl chloride (6.3 mL) at 5° C. and the resultant mixture was warmed to ambient temperature. After 2 h, the crude product mixture was partitioned between 1N hydrochloric acid (100 mL) and ethyl acetate (100 mL). The phases were separated and the aqueous phase extracted with ethyl acetate (50 mL). The combined organic solution was washed with water, then concentrated with concomitant replacement of solvent with isopropanol. After cooling the resultant mixture to 5° C., the white crystalline product was collected, rinsed with cold isopropanol, and dried to afford 12.14 g (65.1% yield based on cyanomethyl tosylate) of N-(3-cyanomethoxyphenyl)methanesulfonamide (99.8% pure by HPLC). This material could optionally be recrystallized from isopropanol.

3. Preparation of N-[3-(4,5-dihydro-1-H-imidazol-2-ylmethoxy)phenyl]-methanesulfonamide hydrochloride monohydrate

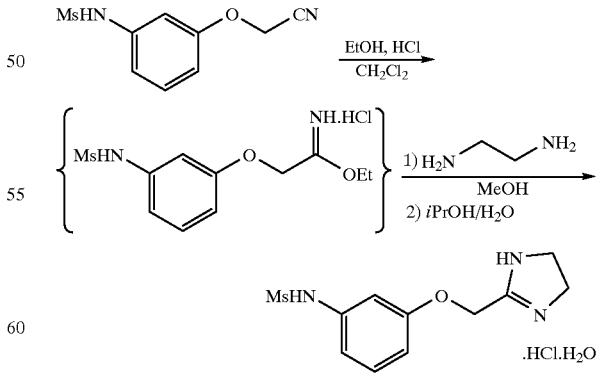

Gaseous hydrogen chloride was bubbled through a suspension of N-(3-cyanomethoxyphenyl)methanesulfonamide (10.0 g) in a mixture of dichloromethane (60 mL) and ethanol (3.0 mL) for 8 min (to saturation), keeping the temperature below 15° C. The resultant mixture was stirred at ambient temperature for 3 h, during which time the intermediate imidate ester hydrochloride precipitated from a transiently homogeneous solution. Excess hydrogen chloride was purged from the reaction vessel by nitrogen, and the resultant slurry was completely dissolved by the addition of methanol (60 mL). This solution was then added over 15 min to a solution of ethylene diamine (2.85 mL, 2.56 g) in methanol (20 mL), keeping the temperature below 25° C. After 1 h, the solvent was replaced by a 9:1 mixture of isopropanol and water (100 mL) via distillation. After concentrating the mixture to ca 90 mL, the resultant slurry was cooled, and the crystalline product was collected. After rinsing with isopropanol, the solid was dried to provide 11.97 g of N-[3-(4,5-dihydro-1-H-imidazol-2-yl-methoxy) phenyl]methanesulfonamide hydrochloride monohydrate (86.8% yield, 99.8% pure by HPLC). This material may optionally be recrystallized from 9:1 isopropanol/water.

Example 1B

Preparation of ethanesulfonic acid [3-(4,5-dihydro-1H-imidazol-2-ylmethoxy)-phenyl]-amide hydrochloride (R=Et), propane-1-sulfonic acid [3-(4,5-dihydro-1H-imidazol-2-ylmethoxy)-phenyl]-amide hydrochloride (R=n–Pr) and N-[3-(4,5-dihydro-1H-imidazol-2-ylmethoxy)-phenyl]-benzenesulfonamide hydrochloride (R=$C_6H_5$)

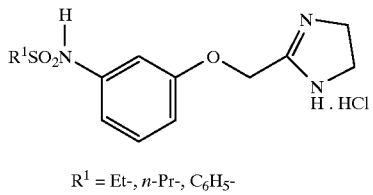

$R^1$ = Et-, n-Pr-, $C_6H_5$-

Ethanesulfonic acid [3-(4,5-dihydro-1H-imidazol-2-ylmethoxy)-phenyl]-amide hydrochloride (R=Et), mp 155.7–157.7° C., was prepared in a manner similar to that described in Example 1, except ethanesulfonyl chloride was used in place of methanesulfonyl chloride.

Propane-1-sulfonic acid [3-(4,5-dihydro-1H-imidazol-2-ylmethoxy)-phenyl]-amide hydrochloride (R=n–Pr), mp 129.3–132.9° C., was prepared in a manner similar to that described in Example 1, except 1-propanesulfonyl chloride was used in place of methanesulfonyl chloride.

N-[3-(4,5-dihydro-1H-imidazol-2-ylmethoxy)-phenyl]-benzenesulfonamide hydrochloride (R=$C_6H_5$), mp 241.5–243.5° C., was prepared in a manner similar to that described in Example 1, except benzenesulfonyl chloride was used in place of methanesulfonyl chloride.

Example 2

Preparation of N-[5-(4,5-dihydro-1H-imidazol-2-ylmethoxy-2-methyl-phenyl]-methanesulfonamide hydrochloride

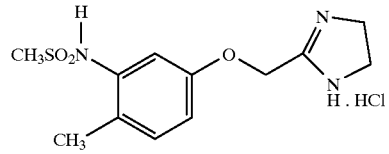

N-[5-(4,5-dihydro-1H-imidazol-2-ylmethoxy-2-methyl-phenyl]-methanesulfonamide hydrochloride

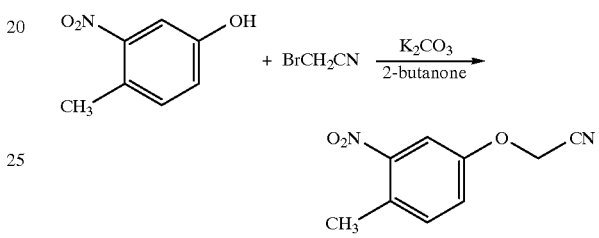

4-Methyl-3-nitrophenol (5.0 g) (TCI America, Portland, Oreg.) and 4.70 g of bromoacetonitrile were dissolved in 30 ml of 2-butanone; then 13.5 g of potassium carbonate was added and the mixture was stirred and heated at 70° C. for 2 hours. The reaction mixture was cooled to room temperature, poured into ethyl acetate, washed with water, dried, and evaporated to give 6.1 g of (4-methyl-3-nitrophenoxy)-acetonitrile as a brown oil.

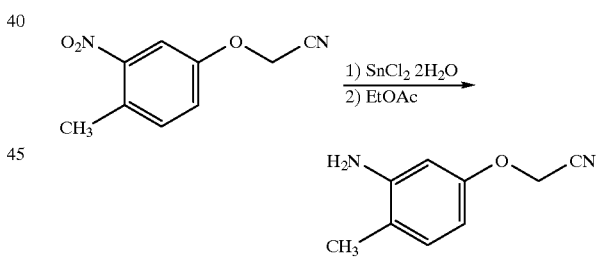

(4-Methyl-3-nitrophenoxy)-acetonitrile (6.0 g) was dissolved in 120 ml of ethyl acetate and treated with 21.8 g of tin (II) chloride dihydrate; and the mixture was stirred at 70° C. for 2 hours. The mixture was cooled, poured into a saturated solution of sodium bicarbonate, extracted with ethyl acetate, dried, and evaporated. The residue was purified by silica gel chromatography eluting with ethyl acetate-:hexane (7:3) to give 2.7 g of (3-amino-4-methylphenoxy)-acetonitrile.

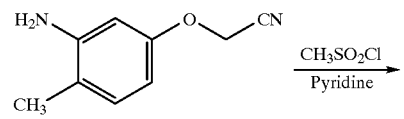

-continued

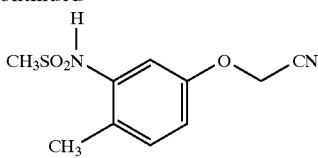

(3-Amino-4-methylphenoxy)-acetonitrile (2.6 g) was dissolved in 10 ml of pyridine, cooled in an ice bath; 2.29 g of methanesulfonyl chloride was added; and the reaction mixture was stirred at 5° C. for 1 hour. The mixture was poured into ethyl acetate, washed with hydrochloric acid, then water, dried, and evaporated giving 3.5 g of N-(5-cyanomethoxy-2-methylphenyl)-methanesulfonamide.

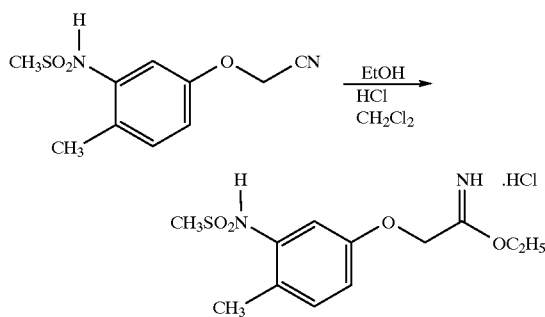

N-(5-Cyanomethoxy-2-methylphenyl)-methanesulfonamide (3.48 g) was dissolved in a mixture of 70 ml of dichloromethane and 3.5 ml of ethanol. The reaction mixture was cooled in an ice bath, saturated with hydrogen chloride gas (Matheson, Newark, Calif.), and slowly allowed to come to room temperature and kept there for 16 hours. The solvent was evaporated leaving 5.2 g of 2-(4-methyl-3-methanesulfonylaminophenoxy)-acetimidic acid ethyl ester hydrochloride.

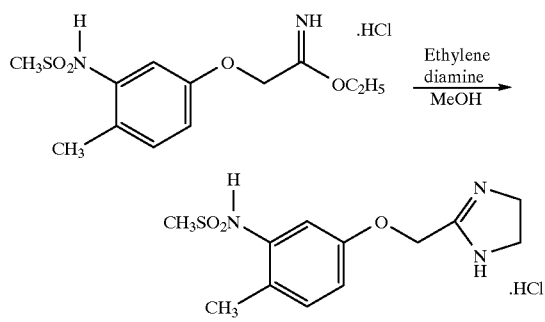

2-(4-Methyl-3-methanesulfonylaminophenoxy)-acetimidic acid ethyl ester hydrochloride (5.2 g) was dissolved in 50 ml of methanol. To this mixture was added 1.05 g of ethylene diamine, and the mixture was stirred at room temperature for 6 hours. The solvent was evaporated and the residue was purified by silica gel chromatography using ethyl acetate:methanol:isopropyl amine (92:5:3) as eluting solvent to give 3.3 g of product. The hydrochloride salt was prepared by addition of 1M hydrogen chloride in ether and the product was crystallized from methanol:ether (1:3) to give 3.3 g of N[5-(4,5-dihydro-1H-imidazol-2-ylmethoxy-2-methylphenyl]-methanesulfonamide hydrochloride, mp 211° C.

Example 2A

Preparation of N-[5-(4,5-dihydro-1H-imidazol-2ylmethoxy-2-chloro-phenyl]-methanesulfonamide hydrochloride (R=Cl) and N-[5-(4,5-dihydro-1H-imidazol-2-ylmethoxy-2-fluoro-phenyl]-methanesulfonamide hydrochloride (R=F)

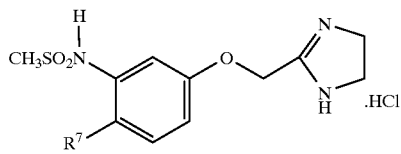

$R^7$ = Cl-, F-

N-[5-(4,5-dihydro-1H-imidazol-2ylmethoxy-2-chloro-phenyl]-methanesulfonamide hydrochloride (R=Cl), mp 228.2–228.5° C., was prepared in a manner similar to that described above for Example 2, except starting with 4-chloro-3-nitrophenol in place of 4-methyl-3-nitrophenol.

N-[5-(4,5-dihydro-1H-imidazol-2-ylmethoxy-2-fluoro-phenyl]-methanesulfonamide hydrochloride (R=F), mp 211.7–212.4° C., was prepared in a manner similar to that described above for Example 2, except starting with 4-fluoro-3-nitrophenol (in place of 4-methyl-3-nitrophenol), which was prepared according to the general method described by Meurs, et al., *Tetrahedron*, (1991) 47:705.

Example 2B

Preparation of N-[3-(4,5-dihydro-1H-imidazol-2-ylmethoxy-2-methyl-phenyl]-methanesulfonamide hydrochloride

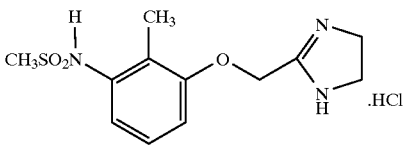

N-[3-(4,5-dihydro-1H-imidazol-2-ylmethoxy-2-methyl-phenyl]-methanesulfonamide hydrochloride, mp 236.7–237.3° C., was prepared in a manner similar to that described above in Example 2, except starting with 2-methyl-3-nitro-phenol in place of 4-methyl-3-nitrophenol.

Example 2C

Preparation of N-[6-chloro-3-(4,5-dihydro-1H-imidazol-2-ylmethoxy-2-methylphenyl]methanesulfonamide hydrochloride

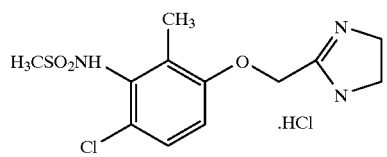

N-[6-chloro-3-(4,5-dihydro-1H-imidazol-2-ylmethoxy-2-methylphenyl]methanesulfonamide hydrochloride

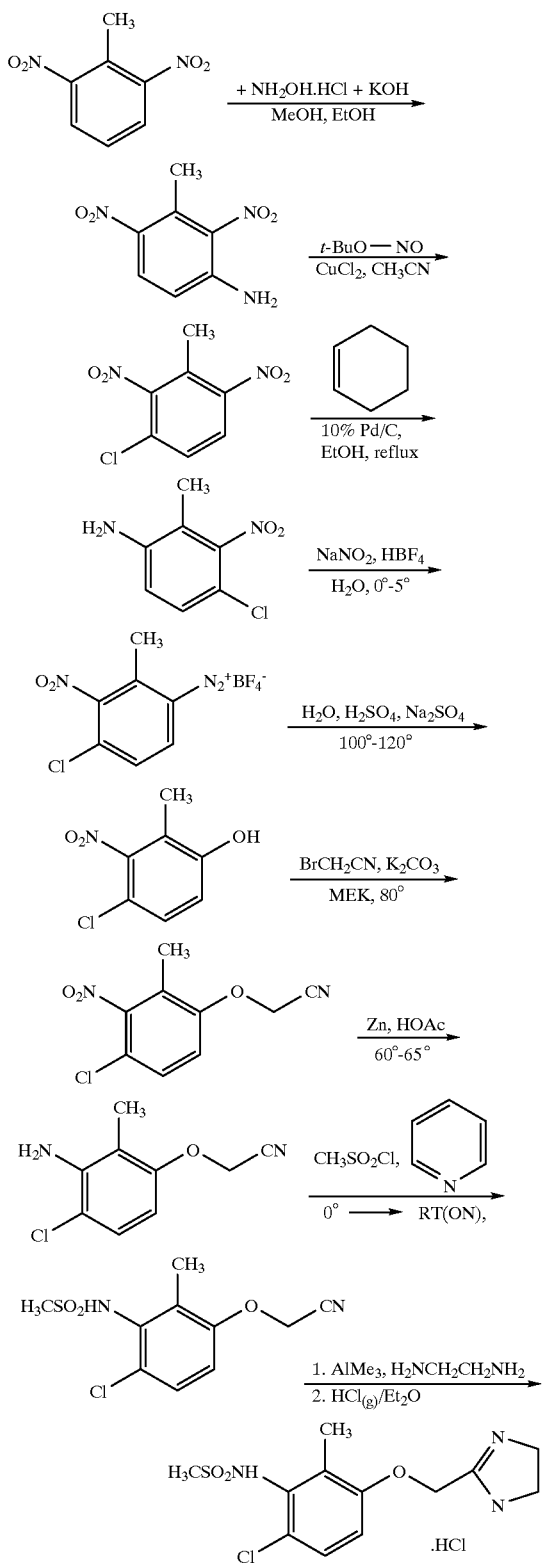

1. Preparation of 2,4-dinitro-3-methylaniline 2,4-dinitro-3-methylaniline was prepared by a modification of the procedure described by Meisenheimer, et al., *Chem. Ber.* (1906) 39:2533. A mixture of 2,6-dinitrotoluene (55.0 g) and hydroxylamine hydrochloride (55.0 g) was stirred in 1.4 L of ethanol until solution took place. 2N Potassium hydroxide solution (550 mL) was added all at once and the resulting mixture allowed to stir for 24 hr. A solution of ammonium chloride (71 g) in water (350 mL) was added and the mixture stirred for an additional hour. The reaction mixture was evaporated under reduced pressure. The residue was partioned between ethyl acetate (750 mL) and 50% saturated sodium chloride solution (500 mL). The ethyl acetate extract was separated and dried over magnesium sulfate. Evaporation under reduced pressure afforded a crude product (52.6 g) which was flash chromatographed on silica and eluted, first with ethyl acetate:hexane (1:3), then with ethyl acetate:hexane (1:2) to afford 36.0 g of product, mp 126.7–131.4° C.

2. Preparation of 3-chloro-2,6-dinitrotoluene

Copper (II) chloride (29.5 g) and dry acetonitrile (350 mL) were placed in a three neck 1 liter flask equipped with overhead stirrer, condenser, and nitrogen inlet tube and heated to 60–65° C. T-butyl nitrite (32.6 mL) was added all at once, then 2,4-dinitro-3-methylaniline (36.0 g) was added portionwise to the above mixture. The mixture was allowed to stir at temperature for an additional 15 min. The reaction mixture was cooled to room temperature and evaporated under reduced pressure. The residue was partioned between ethyl ether (650 mL) and 6N hydrochloric acid solution (650 mL). The ethereal solution was separated, washed with saturated sodium chloride solution (500 mL), then dried over magnesium sulfate to afford the crude product. The crude material was flash chromatographed on silica and eluted with ethyl ether to afford 37.8 g as a yellow solid.

3. Preparation of 4-chloro-2-methyl-3-nitroaniline

A mixture of 3-chloro-2,6-dinitrotoluene (18.0 g), cyclohexene (51 mL), and 10% palladium on charcoal (4.5 g) in ethanol (350 mL) was heated at reflux under an atmosphere of nitrogen for 1.5 hr. The reaction mixture was cooled to room temperature, filtered through celite, then evaporated under reduced pressure. The residue was dissolved in ethyl ether and filtered through a short silica column. Evaporation of the ether afforded 14.8 g as an orange solid.

4. Preparation of 4-chloro-2-methyl-3-nitrophenol

A slurry of 4-chloro-2-methyl-3-nitroaniline (20.9 g), water (200 mL), and fluroboric acid (86 mL) was heated to boiling until almost complete solution took place, then cooled to 0–5° C. A solution of sodium nitrite (8.11 g) in water (20 mL) was then added dropwise to the above mixture, and then the mixture was stirred in the cold for an additional 30 min. The precipitated diazonium salt was filterd off and washed with a little cold water. The wet diazonium salt was added all at once to a hot (100–120° C.) solution of water (230 mL), concentrated sulfuric acid (115 mL), and sodium sulfate (35 g), and allowed to stir for 4 hr. The reaction mixture was cooled to room temperature and extracted with ethyl ether (700 mL in two portions). The combined ether extracts were washed with saturated sodium chloride solution, then dried over magnesium sulfate. Evaporation afforded crude product (17.5 g), which was purified by flash chromatography on silica, eluting with methylene chloride to afford 7.6 g as a yellow solid.

The phenol was also prepared by the NCS chlorination of 2-methyl-3-nitrophenol, in a manner similar to that described in Oberhauser, *J. Org. Chem.* (1997) 62:4504–4506, as follows.

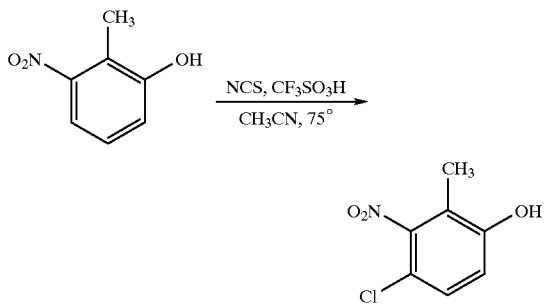

2-Methyl-3-nitrophenol (25.5 g), N-chlorosuccinimide (44.5 g), and trifluormethanesulfonic acid (50.0 g) were combined in dry acetonitrile (500 mL) and allowed to stir under an atmosphere of nitrogen at 75° C. for 1.5 hr. The reaction mixture was cooled to room temperature, diluted with ethyl ether (650 mL), washed with water, 10% sodium bisulfite solution, water, and finally saturated sodium chloride solution. Evaporation of the solvent afforded a crude material which was flash chromatographed on silica and eluted with acetone:hexane (1:9) to afford 16.8 g as a yellow solid.

5. Preparation of (4-chloro-2-methyl-3-nitrophenoxy) acetonitrile

A mixture of 4-chloro-2-methyl-3-nitrophenol (7.6 g), bromoacetonitrile (3.4 mL), and potassium carbonate (16.8 g) in 2-butanone (80 mL) was heated at 80° C. for 2 hr under an atmosphere of nitrogen. The reaction mixture was cooled to room temperature, then filtered to remove the salts. The filtrate was diluted with ethyl ether (200 mL), washed with saturated sodium chloride solution, and dried over magnesium sulfate. Evaporation of the solvent afforded a yellow solid (9.1 g).

6. Preparation of (3-amino-4-chloro-2-methylphenoxy) acetonitrile

A mixture of (4-chloro-2-methyl-3-nitrophenoxy) acetonitrile (9.1 g) and zinc (dust) (10.5 g) in glacial acetic acid (90 mL) was heated at 60–65° C. for 4 hr under an atmosphere of nitrogen. The reaction mixture was cooled to room temperature, then filtered through celite. The filtrate was evaporated under reduced pressure and the residue partitioned between ethyl ether (500 mL) and 10% ammonium hydroxide solution (500 mL). The ethereal solution was separated, washed with saturated sodium chloride solution, and dried over magnesium sulfate. The solvent was removed under reduced pressure and the residue flash chromatographed on silica, eluting with ethyl acetate:hexane (1:4) to afford 4.76 g as a light yellow oil which crystallized on standing.

7. Preparation of N-(6-chloro-3-cyanomethoxy-2-methylphenyl)methanesulfonamide (3-amino-4-chloro-2-methylphenoxy)acetonitrile (4.76 g) was dissolved in pyridine (45 mL) under an atmosphere of nitrogen and cooled in an ice bath. Methanesulfonyl chloride (2.06 mL) was added dropwise, and then the mixture was allowed to stir overnight at room temperature. The reaction mixture was evaporated to dryness under reduced pressure to afford a residue which was flash chromatographed on silica and eluted with, first ethyl acetate:hexane (1:2), then with ethyl acetate:hexane (1:1) to afford 5.36 g as an 80:20 mixture of mono and bis mesylated product, respectively. This mixture was used in the next step without any further purification.

8. Preparation of N-[6-chloro-3-(4,5-dihydro-1H-imidazol-2-ylmethoxy-2-methylphenyl]methanesulfonamide Ethylenediamine (5.21 g) and toluene (40 mL) were placed on a 200 mL 3 neck flask equipped with stir bar, nitrogen inlet tube, septum, and addition funnel. The mixture was cooled in an ice bath and a 2.0M trimethylaluminum in toluene solution (39 ml) was added dropwise, then allowed to stir a room temperature for 2 hr. N-(6-chloro-3-cyanomethoxy-2-methyl)methanesulfonamide (5.36 g) was added in one portion. The mixture was then heated at reflux for 6 hr and allowed to stir overnight at room temperature. Methanol (150 mL) was cautiously added then heated at reflux for 30 min and cooled to room temperature. The reaction mixture was filtered through celite and the filtrate evaporated to dryness. The residue was flash chromatographed on silica and eluted first with ethyl acetate:methanol:2-propylamine (40:5:1), then with ethyl acetate:methanol:2-propylamine (40:10:2) to afford 4.74 g after evaporation of the solid. The solid (free base) was suspended in methanol (50 mL) and 1.0M HCl in ethyl ether (30 mL) was quickly added and allowed to stir at room temperature for one hr. The product was filtered off, washed with a little ether, and dried to afford 4.83 g, mp 268.0–269.1° C.

Example 2D

Preparation of N-[6-bromo-3-(4,5-dihydro-1H-imidazol-2-ylmethoxy-2-methylphenyl] methanesulfonamide hydrochloride

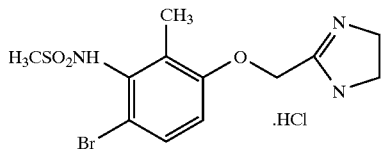

N-[6-bromo-3-(4,5-dihydro-1H-imidazol-2-ylmethoxy-2-methylphenyl]methanesulfonamide, mp 271.5–271.9° C., was prepared in a manner similar to that described above for N-[6-chloro-3-(4,5-dihydro-1H-imidazol-2-ylmethoxy-2-methylphenyl]methanesulfonamide, except that copper (II) bromide was used in place of copper (II) chloride.

Example 2E

Preparation of N-[5-chloro-3-(4,5-dihydro-1H-imidazol-2-ylmethoxy-2-methylphenyl] methanesulfonamide hydrochloride

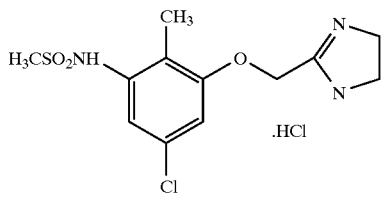

N-[5-chloro-3-(4,5-dihydro-1H-imidazol-2-ylmethoxy-2-methylphenyl]methanesulfonamide, mp 198.1–199.3° C., was prepared in a similar manner to that described above for N-[4-chloro-3-(4,5-dihydro-1H-imidazol-2-ylmethoxy-2-methylphenyl]methane-sulfonamide, except the starting material was 5-chloro-2-methyl-3-nitroaniline described in Scheme Q (Example 6D).

Example 2F

Alternative preparation of N-[6-chloro-3-(4,5-dihydro-1H-imidazol-2-ylmethoxy-2-methylphenyl] methanesulfonamide hydrochloride

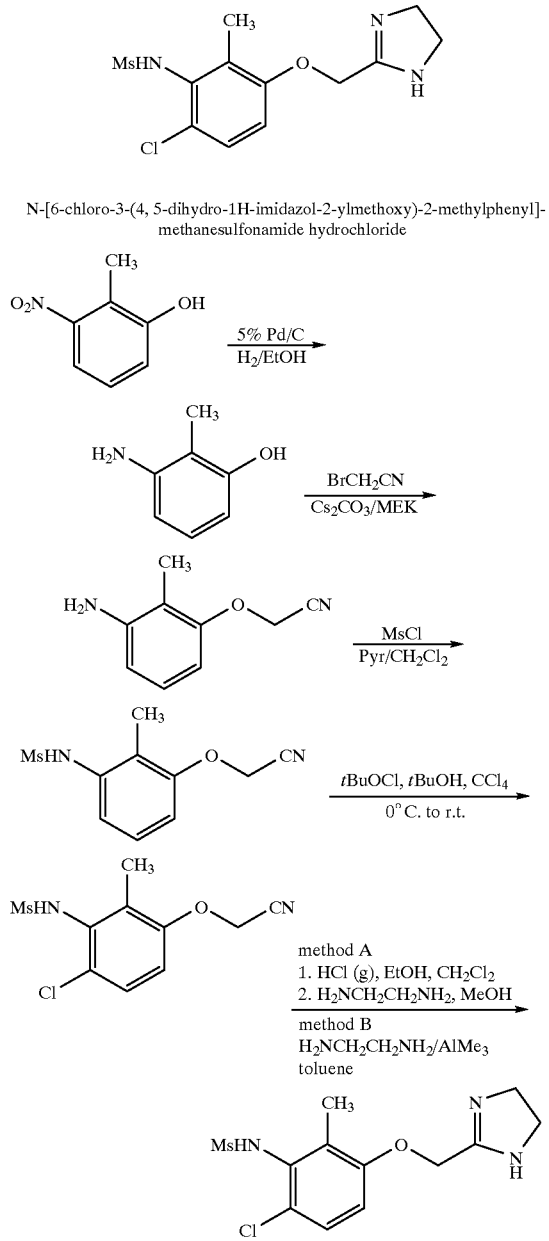

1. Preparation of 2-methyl-3-aminophenol

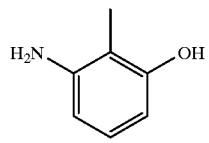

2-methyl-3-nitrophenol (25 g, 0.163 mol) was dissolved in 170 ml of absolute ethanol in a 1 l Parr hydrogenation flask. The flask was purged with nitrogen. 10% palladium on charcoal (1.73 g, 1.6 mmol) was added and the mixture was hydrogenated (40 psi $H_2$) for 1.5 hr in a Parr apparatus. The flask was evacuated and purged with nitrogen. The catalyst was removed by filtration through a Whatman GF/F filter. After removal of the ethanol at reduced pressure, 20.1 g (100% yield) of 2-methyl-3-aminophenol was obtained as a lightly brown solid.

2. Preparation of (2-methyl-3-aminophenoxy)acetonitrile

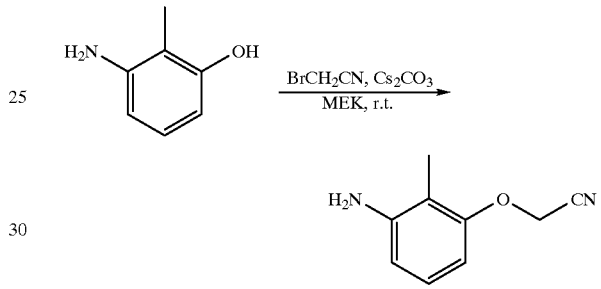

2-methyl-3-aminophenol (20.1 g, 0.163 mol) was dissolved in methylethylketone (MEK) (150 ml). Cesium carbonate (106 g, 0.326 mmol) was added in portions followed by dropwise addition of bromoacetonitrile (29.3 g, 0.245 mol) over 30 min. The mixture was stirred 14 hr at room temperature, then filtered through a coarse fritted funnel. The solids were washed with ethylacetate (2×100 ml) and the combined washings and filtrate were concentrated at reduced pressure to give 20.8 g (79% yield) of (2-methyl-3-aminophenoxy)acetonitrile which required no further purification.

3. Preparatation of N-(3-cyanomethoxy-2-methylphenyl)-methanesulfonamide

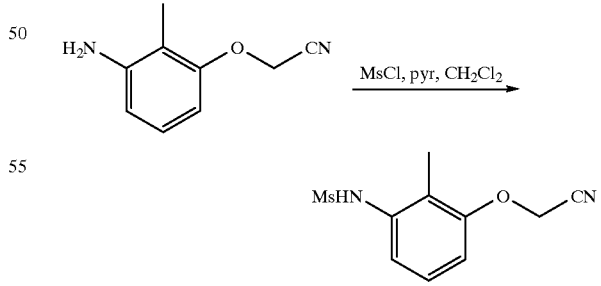

N-(3-cyanomethoxy-2-methylphenyl)-methanesulfonamide was prepared from (2-methyl-3-aminophenoxy)acetonitrile in a manner similar to that described in Example 1 for the preparation of N-(3-cyanomethoxyphenyl)-methanesulfonamide from (3-aminophenoxy)-acetonitrile.

4. Preparation of N-(6-chloro-3-cyanomethoxy-2-methylphenyl)-methanesulfonamide

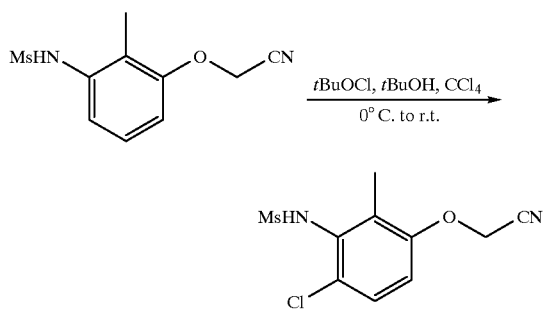

N-(3-cyanomethoxy-2-methylphenyl)-methanesulfonamide (1.87 g, 7.78 mmol) was suspended in a 1:1 mixture of t-butanol and carbon tetrachloride (80 ml) and cooled in an ice bath. t-Butyl hypochlorite (TCl, 0.85 g, 7.78 mmol) was added dropwise. The mixture was maintained at −4° C. overnight then warmed to room temperature. The volatiles were removed at reduced pressure. N-(6-chloro-3-cyanomethoxy-2-methylphenyl)-methanesulfonamide (1.05 g, 49% yield) was obtained by recrystallization from toluene.

5. N-[6-chloro-3-(4,5-dihydro-1H-imidazol-2-ylmethoxy-2-methylphenyl]-methanesulfonamide hydrochloride

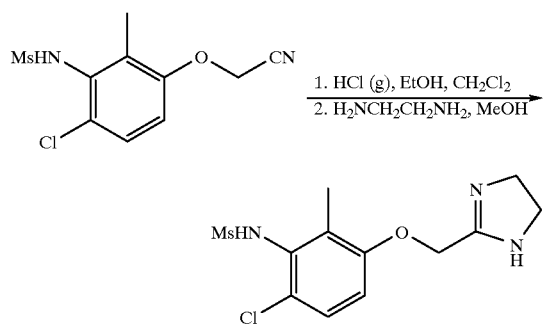

N-[6-chloro-3-(4,5-dihydro-1H-imidazol-2-ylmethoxy-2-methylphenyl]-methanesulfonamide hydrochloride was prepared from N-(6-chloro-3-cyanomethoxy-2-methylphenyl)-methanesulfonamide in a manner similar to that described in Example 1 for the preparation of N-[3-(4,5-dihydro-1H-imidazol-2-ylmethoxy)phenyl]methanesulfonamide hydrochloride from (3-aminophenoxy)acetonitrile.

Example 2G

Preparation of N-[3-(4,5-dihydro-1H-imidazol-2-ylmethoxy)-2,6-dimethylphenyl] methanesulfonamide

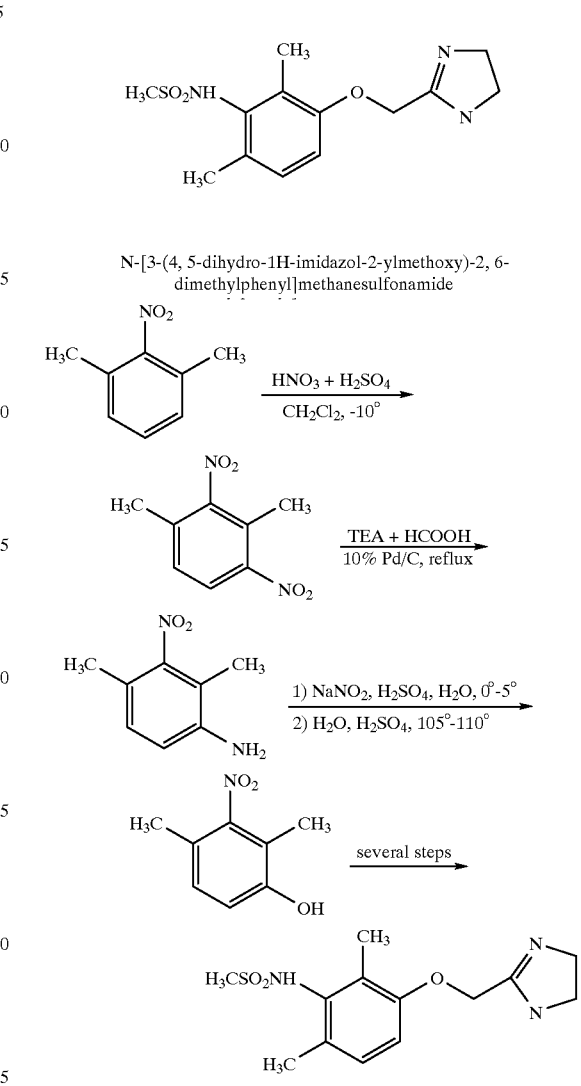

1. Preparation of 2,4-dinitro-m-xylene
   2,6-dinitro-m-xylene was prepared according to the methods described in U.S. Pat. No. 4,564,640.
2. Preparation of 2,4-dimethyl-3-nitroaniline
   A mixture of 2,6-dinitro-m-xylene (11.2 g) and 10% palladium on charcoal (620 mg) was stirred in triethylamine (36 mL) under an atmosphere of nitrogen and heated to reflux. Formic acid (9.25 mL) was added dropwise to the above mixture with vigorous stirring. After addition, the mixture was allowed to stir at reflux for an additional 15 min, then cooled to room temperature. The reaction mixture was diluted with ethyl acetate (100 mL) and filtered through celite. The filtrate was washed with brine and dried over magnesium sulfate. Evaporation afforded 9.51 g as a yellow solid.

3. Preparation of 2,4-dimethyl-3-nitrophenol 2,4-Dimethyl-3-nitroaniline (9.5 g) was heated in a solution of concentrated sulfuric acid (15.5 mL) and water (57 mL) until solution took place, then cooled to room temperature. Water (143 mL) was added and the mixture cooled to 0–5° C. A solution of sodium nitrite (4.03 g) in water (8 mL) was added dropwise to the above solution and then allowed to stir for an additional 15 min in the cold.

The above diazonium solution was added dropwise (via an ice-jacketed addition funnel) to a hot (105–110° C.) solution of concentrated sulfuric acid (60 mL) and water (91 mL); the rate of addition was adjusted to maintain the temperature at 105–110° C. After addition, the mixture was heated for an additional 15 min. The reaction mixture was cooled to room temperature, then extracted with three portions of ethyl acetate (250 mL). The combined extracts were washed with brine, then dried over magnesium sulfate. The crude material was flash chromatographed on silica and eluted with methylene chloride to afford 5.15 g as an orange solid.

4. Preparation of N-[3-(4,5-dihydro-1H-imidazol-2-ylmethoxy-2,6-dimethylphenyl]methanesulfonamide N-[3-(4,5-dihydro-1H-imidazol-2-ylmethoxy-2,6-dimethylphenyl]methanesulfonamide, mp 216.3–216.8° C., was prepared in a similar manner to that described above for N-[6-chloro-3-(4,5-dihydro-1H-imidazol-2-ylmethoxy-2-methylphenyl]methane-sulfonamide, except the starting material was 2,4-dimethyl-3-nitrophenol from above.

Example 2H

Preparation of N-[5-(4,5-dihydro-1H-imidazol-2-ylmethoxy-2,4-dimethylphenyl]methanesulfonamide hydrochloride

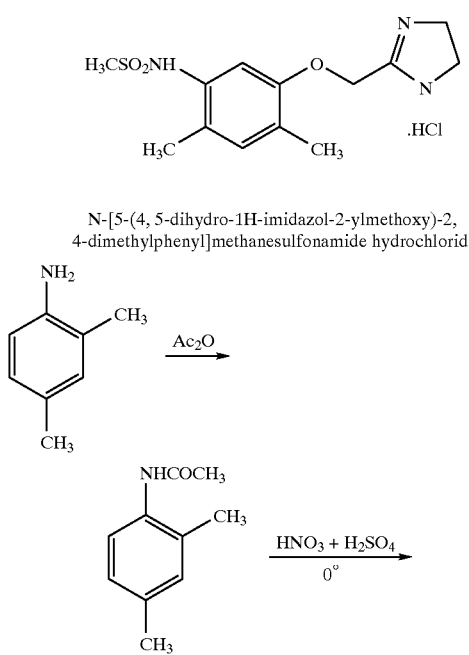

N-[5-(4, 5-dihydro-1H-imidazol-2-ylmethoxy)-2,4-dimethylphenyl]methanesulfonamide hydrochloride

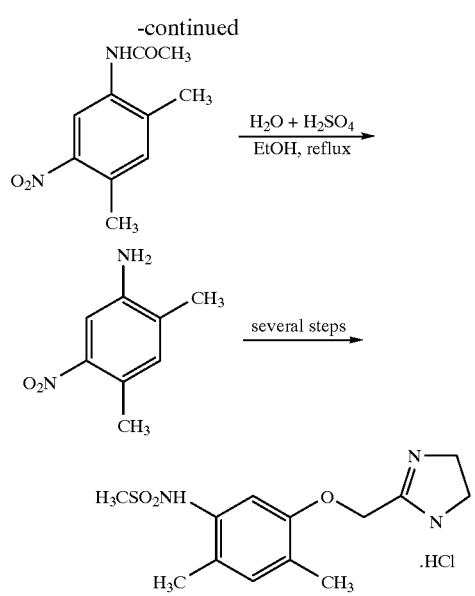

1. Preparation of N-(2,4-dimethylphenyl)acetamide 2,4-Dimethylaniline (10.0 g) and acetic anhydride (9.26 mL) were combined all at once and allowed to stir at room temperature for 2 hours. The solid mass which resulted was dissolved in ethyl acetate (300 mL), washed with 0.5M sodium hydroxide solution, brine and dried over magnesium sulfate. Evaporation of the solvent afforded 10.5 g as a white solid.

2. Preparation of N-(2.4-dimethyl-5-nitrophenyl)acetamide

A mixture of concentrated nitric acid (20 mL) and concentrated sulfuric acid (20 mL) was cooled in an ice-salt bath to 0° C. N-(2,4-dimethylphenyl)acetamide (9.5 g) was added portionwise at such a rate to maintain the temperature below 5° C. The mixture was then allowed to stir in the cold for an additional one hour.

The reaction mixture was poured into ice (500 g) with stirring and then extracted with ethyl acetate (1 L). The ethyl acetate extract was washed with brine and dried over magnesium sulfate. Evaporation afforded a crude material which was flash chromatographed on silica and eluted with ethyl acetate:hexane (1:1) to afford 9.64 g as a light yellow solid.

3. Preparation of 2,4-dimethyl-5-nitroaniline

A mixture of N-(2,4-dimethyl-5-nitrophenyl)acetamide, water (24 mL), concentrated sulfuric acid (12 mL), and ethanol (120 mL) was heated at reflux under an atmosphere of nitrogen for 4 hours. The ethanol was evaporated under reduced pressure and the residue partitioned between ethyl acetate (250 mL) and brine (150 mL). The brine solution was reextracted with ethyl acetate. The combined ethyl acetate extracts were then dried over magnesium sulfate. Evaporation afforded a crude product which was flash chromatographed on silica and eluted with ethyl acetate:hexane (1:4) to afford 4.63 g as a pale yellow solid.

4. Preparation of N-[5-(4,5-dihydro-1H-imidazol-2-ylmethoxy-2,4-dimethylphenyl]methanesulfonamide hydrochloride N-[5-(4,5-dihydro-1H-imidazol-2-ylmethoxy-2,4-dimethylphenyl]methanesulfonamide hydrochloride, mp 219.7–219.9° C., was prepared in a similar manner to that described above for N-[6-chloro-3-(4,5-dihydro-1H-imidazol-2-ylmethoxy-2-methylphenyl]methane-sulfonamide, except the starting material was 2,4-dimethyl-5-nitroaniline from above.

Example 2I

Preparation of N,N-dimethyl-N-[3-(4,5-dihydro-1H-imidazol-2-ylmethoxy-2,6-dimethylphenyl]sulfamide hydrochloride

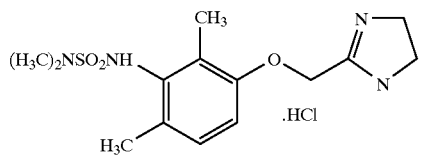

N,N-dimethyl-N -[3-(4,5-dihydro-1H-imidazol-2-ylmethoxy-2,6-dimethyl-phenyl]sulfamide hydrochloride, mp 227.7–228.1° C., was prepared in a similar manner to that described above for N-[3-(4,5-dihydro-1H-imidazol-2-ylmethoxy-2,6-dimethylphenyl]methane-sulfonamide, except the starting material was 3-amino-2,4-dimethylphenoxy)acetonitrile from above and N,N-dimethylsulfamoyl chloride.

Example 2J

Preparation of N-[5-(4,5-dihydro-1H-imidazol-2ylmethoxy-2-hydroxy-phenyl]methanesulfonamide hydrochloride

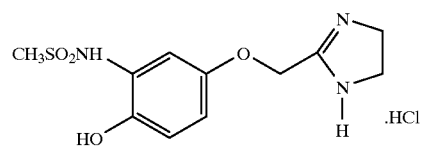

N-[5-(4, 5-dihydro-1H-imidazol-2ylmethoxy)-2-hydroxy-phenyl]-methanesulfonamide hydrochloride

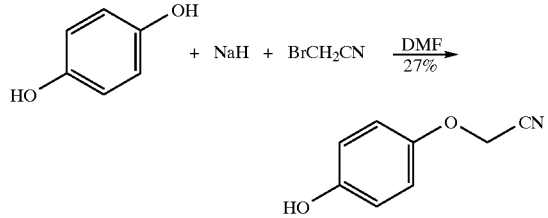

1. Preparation of (4-hydroxy-phenoxy)-acetonitrile

A suspension of 4.36 g of 60% sodium hydride in mineral oil (oil removed by hexane washing) in 50 ml of N,N-dimethylformamide was cooled in an ice bath and added to a solution of 10 g of hydroquinone in 50 ml of N,N-dimethylformamide. After the bubbling subsided, the mixture was heated to 70° C. for 3 hours and cooled again in an ice bath. 12.0 g of bromoacetonitrile was added dropwise. After the addition, the ice bath was removed and the mixture stirred at room temperature for 1 hour. The mixture was poured into ethyl acetate and ice water added. The mixture was acidified with concentrated hydrochloric acid, washed with brine, dried (MgSO$_4$), and evaporated to dryness. The residue was purified by silica gel chromatography eluting with ethyl acetate/dichloromethane (3:97) and obtained 3.86 g of (4-hydroxy-phenoxy)-acetonitrile as a yellow oil.

2. Preparation of (4-hydroxy-3-nitro-phenoxy)-acetonitrile

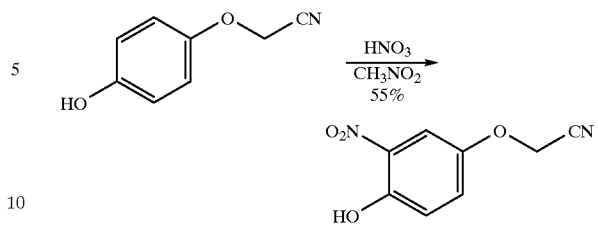

A solution of 7.5 g of (4-hydroxy-phenoxy)-acetonitrile dissolved in 60 ml of nitromethane was cooled in an ice bath and 3.88 ml of 70% nitric acid was added dropwise. After 45 minutes, the reaction mixture was poured into ethyl acetate, washed with brine, dried (MgSO$_4$), and evaporated to dryness. The crude product was purified by silica gel chromatography eluting with ethyl acetate/hexane (1:3), giving 5.45 g of (4-hydroxy-3-nitro-phenoxy)-acetonitrile as a yellow solid, mp 113.1–114.1° C.

3. Preparation of (4-benzyloxy-3-nitro-phenoxy)-acetonitrile

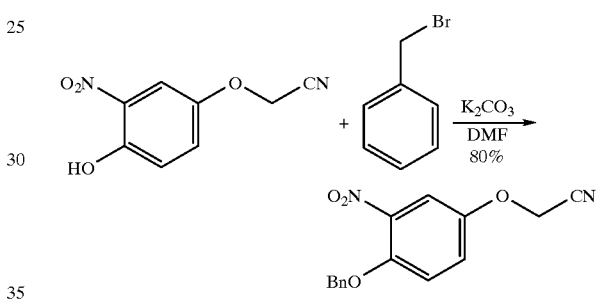

A heterogeneous mixture of 6.0 g of (4-hydroxy-3-nitro-phenoxy)-acetonitrile, 50 ml N,N-dimethylformamide, 12.8 g of potassium carbonate, and 5.8 g of benzyl bromide was heated with stirring at 70° C. for 22 hours. The mixture was cooled to room temperature, poured into ethyl acetate, washed with water, washed with 1N sodium hydroxide, again with water, dried (MgSO$_4$), evaporated, and obtained 7.06 g of (4-benzyloxy-3-nitro-phenoxy)-acetonitrile as a tan solid.

4. Preparation of (3-amino-4-benzyloxy-phenoxy)-acetonitrile

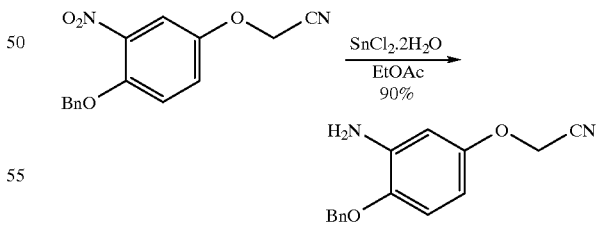

A solution of 6.9 g (4-benzyloxy-3-nitro-phenoxy)-acetonitrile, 200 ml of ethyl acetate, and 27.4 g of tin (II) chloride dihydrate was stirred at room temperature for 17 hours, poured into ethyl acetate, added saturated sodium bicarbonate solution, extracted twice with ethyl acetate, dried (MgSO$_4$), evaporated, and obtained 6.0 g of (3-amino-4-benzyloxy-phenoxy)-acetonitrile as a light brown oil.

5. Preparation of N-(2-benzyloxy-5-cyanomethoxy-phenyl)-methanesulfonamide

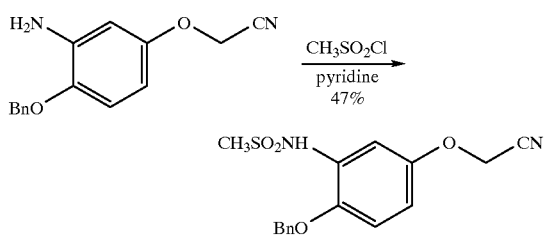

A solution of 5.9 g of (3-amino-4-benzyloxy-phenoxy)-acetonitrile and 24 ml of pyridine was cooled in an ice bath and treated at a dropwise rate with 3.46 g of methanesulfonyl chloride and stirred for 1 hour. The mixture was treated with 5 ml of water, removed the ice bath, and stirred at room temperature for 30 minutes. The mixture was poured into ethyl acetate, ice added, acidified with concentrated hydrochloric acid, washed with brine, dried (MgSO$_4$), and evaporated. The residue was purified on silica gel eluting with ethyl acetate/hexane (2:5) and obtained 3.57 g of N-(2-benzyloxy-5-cyanomethoxy-phenyl)-methanesulfonamide as a cream solid.

6. Preparation of N-[2-benzyloxy-5-(4,5-dihydro-1H-imidazol-2-ylmethoxy)-phenyl]-methanesulfonamide

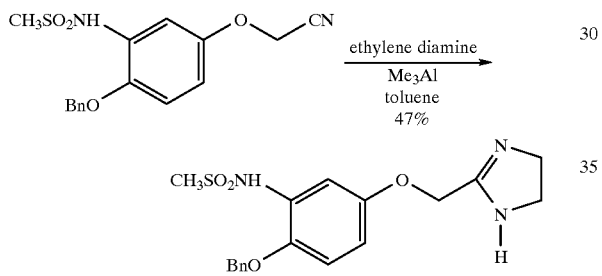

A solution of 1.49 g of ethylene diamine in 20 ml of toluene was cooled in an ice bath and a solution of 12.4 ml of 2M trimethylaluminum in toluene was slowly added. The ice bath was removed, and the mixture stirred at room temperature for 1 hour. A mixture of 2.73 g of N-(2-benzyloxy-5-cyanomethoxy-pheny)-methanesulfonamide and 40 ml of toluene was treated with the above complex and heated to 125° C. for 14 hours. The mixture was cooled to room temperature, diluted with dichloromethane, and the excess reagent was decomposed with methanol, filtered through a Celite pad, and evaporated to dryness. The residue was purified by silica gel chromatography eluting with ethyl acetate/methanol/isopropyl amine (96:2:2), giving 1.43 g of N-[2-benzyloxy-5-(4,5-dihydro-1H-imidazol-2-ylmethoxy)-phenyl]-methanesulfonamide as a white solid.

7. Preparation of N-[5-(4,5-dihydro-1H-imidazol-2-ylmethoxy-2-hydroxy-phenyl]-methanesulfonamide

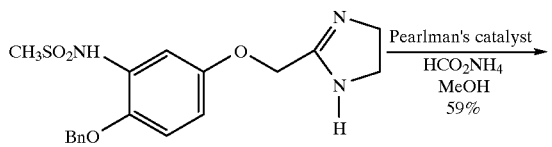

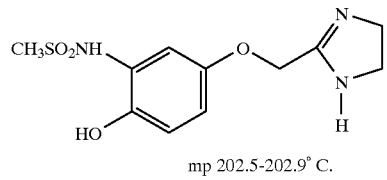

mp 202.5-202.9° C.

A solution of 900 mg of N-[2-benzyloxy-5-(4,5-dihydro-1H-imidazol-2-ylmethoxy)-phenyl]-methanesulfonamide in 40 ml of methanol was treated with 900 mg of ammonium formate and 450 mg of Pearlman's catalyst (20% Pd) and heated to reflux for 2 hours. The reaction mixture was cooled to room temperature, the catalyst filtered off, and the mixture evaporated to dryness. The mixture was purified by silica gel chromatography eluting with ethyl acetate/methanol/isopropyl amine (85:10:5), giving 404 mg of free base which was converted to the salt, N-[5-(4,5-dihydro-1H-imidazol-2-ylmethoxy-2-hydroxy-phenyl]-methanesulfonamide hydrochloride, mp 202.5–202.9° C.

Example 2K

Preparation of N-[5-(4,5-dihydro-1H-imidazol-2-ylmethoxy-3-chloro-phenyl]-methanesulfonamide hydrochloride

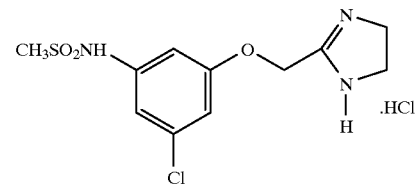

N-[5-(4,5-dihydro-1H-imidazol-2-ylmethoxy-3-chloro-phenyl]-methanesulfonamide hydrochloride 1. Preparation of (3,5-dinitrophenoxy)-acetonitrile

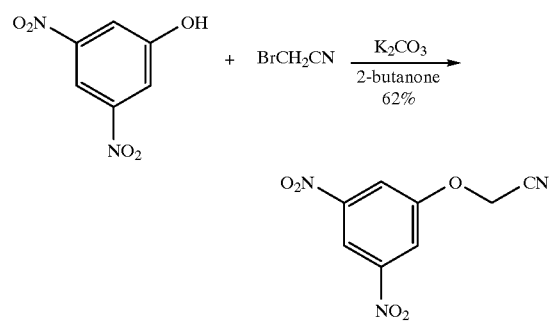

3,5-Dinitrophenol (15.0 g) and 10.75 g of bromoacetonitrile were dissolved in 85 ml of 2-butanone and the solution was treated with 33.78 g of potassium carbonate. The heterogenous mixture was stirred and heated at 70° C. for 5 hours, cooled to room temperature, poured into ethyl acetate, washed with water, dried over magnesium sulfate, and evaporated. The residue was purified by silica gel chromatography eluting with dichloromethane/hexane (3:1) to give 11.24 g of (3,5-dinitrophenoxy)-acetonitrile as a light yellow solid.

2. Preparation of (3-amino-5-nitro-phenoxy)-acetonitrile

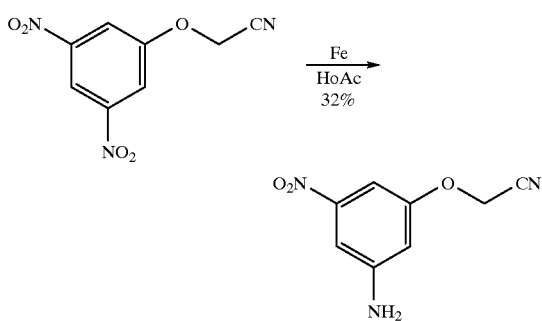

(3,5-Dinitrophennoxy)-acetonitrile (12.5 g) was dissolved in 150 ml of warm acetic acid, and 9.4 g of iron powder added. The mixture was stirred and heated to 50° C. when an exothermic reaction occurred. The mixture was heated at 50° C. for 2 hours. The mixture was cooled to room temperature, poured into ice water, filtered, and the solid residue dissolved in ethyl acetate, dried over magnesium sulfate, filtered, and evaporated to dryness. The residue was purified using a silica gel column eluting with ethyl acetate to give 7.76 g of (3-amino-5-nitro-phenoxy)-acetonitrile as a yellow solid.

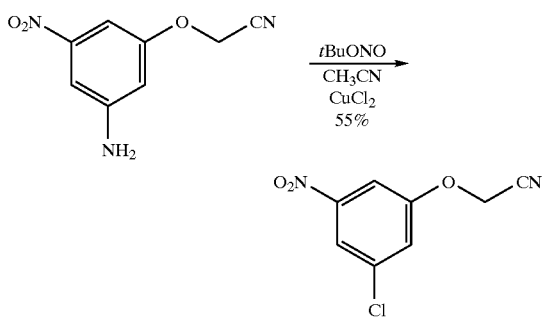

3. Preparation of (3-chloro-5-nitro-phenoxy)-acetonitrile

A dark suspension of 9.05 g of copper (II) chloride in 100 ml of acetonitrile and ml of tert-butyl nitrite was stirred and heated to 60° C. To this mixture was added a solution of 10.84 g of (3-amino-5-nitro-phenoxy)-acetonitrile in 100 ml of acetonitrile. After 15 minutes at 60° C., the solvent was evaporated, water added, and the mixture extracted twice with ethyl acetate, dried (MgSO$_4$), and evaporated. The residue was purified by silica gel chromatography eluting with dichloromethane and giving 9.89 g of (3-chloro-5-nitro-phenoxy)-acetonitrile as a cream solid.

4. Preparation of (3-amino-5-chloro-phenoxy)-acetonitrile

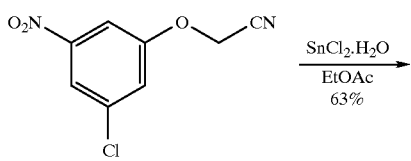

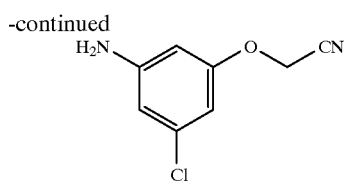

A warm solution of 8.23 g of (3-chloro-5-nitro-phenoxy)-acetonitrile in 150 ml of ethyl acetate was treated with 34.9 g of tin (II) chloride dihydrate and the solution was heated at 70° C. for 2 hours. The reaction mixture was cooled to room temperature, diluted with ethyl acetate, basified with saturated sodium bicarbonate solution, extracted twice with ethyl acetate, dried (MgSO$_4$), and evaporated to dryness. The residue was purified by silica gel chromatography using ethyl acetate/hexane (35:65) as solvent and obtained 4.42 g of (3-amino-5-chloro-phenoxy)-acetonitrile as a cream solid.

5. Preparation of N-[5-(4,5-dihydro-1H-imidazol-2-ylmethoxy-3-chloro-phenyl]-methanesulfonamide hydrochloride

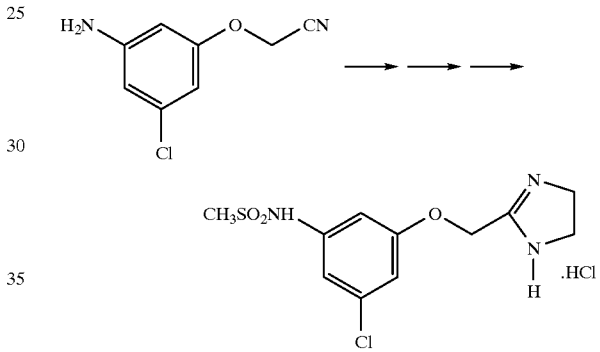

N-[5-(4,5-dihydro-1H-imidazol-2-ylmethoxy-3-chloro-phenyl]-methanesulfonamide hydrochloride, mp 176.5–180.5° C., was prepared in a similar manner to Example 1, except starting with (3-amino-5-chloro-phenoxy)-acetonitrile.

Example 2L

Preparation of N-[3-(4,5-dihydro-1H-imidazol-2ylmethoxy-5-fluoro-phenyl]-methanesulfonamide hydrochloride

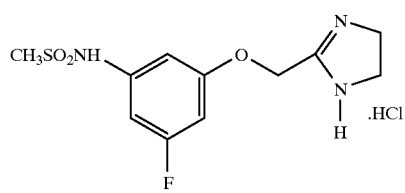

N-[3-(4,5-dihydro-1H-imidazol-2ylmethoxy-5-fluoro-phenyl]-methanesulfonamide hydrochloride, mp 203.2–204.2° C., was prepared in a similar manner to Example 1, except starting with 3-fluoro-5-nitro-phenol which was prepared according to Degiorgi, et al., *Bull. Soc. Chim. Fr.* (1937)1636.

Example 2M

N-[3-(4,5-dihydro-1H-imidazol-2-ylmethoxy-5-methyl-phenyl]-methanesulfonamide hydrochloride

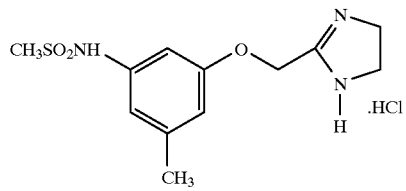

N-[3-(4,5-dihydro-1H-imidazol-2-ylmethoxy-5-methyl-phenyl]-methanesulfonamide hydrochloride, mp 207.8–208.6° C., was prepared in a similar manner to Example 1, except starting with 3-methyl-5-nitro-phenol which was prepared according to Nevile, et al., Chem. Ber. (1882) 15:2986.

Example 2N

Alternative preparation of N-[6-chloro-3-(4,5-dihydro-1H-imidazol-2-ylmethoxy-2-methylphenyl]-methanesulfonamide hydrochloride 1. Preparation of 3-amino-4-chloro-o-cresol To a stirred solution of 3-amino-o-cresol (60 g) in anhydrous methanesulfonic acid (300 ml) was added N-chlorosuccinimide (68.3 g in five equal portions) over 2 h and 10 min, keeping the reaction temperature between 10 and 12° C. by use of a cooling bath. The dark mixture was allowed to stir overnight and warm to room temperature. It was then added to 1000 ml water with stirring (final temperature approx. 51° C.). Concentrated ammonium hydroxide (370 ml) was added with stirring, keeping the temperature between 50 and 60° C. by use of a cooling bath. The product crystallized out near the end of the addition at 50–53° C. The product slurry was cooled to ice bath temperature and held for 1 h. The product, isolated in 70.5% yield by filtration, washing with ice water, and drying in vacuo at 50° C., was 98.44% pure by area-normalized HPLC with correction for relative response factors. It contained only 0.8% of the 6-chloro isomer and 0.68% of the 4,6-dichloro impurity. Recrystallization from isopropanol-water with charcoal treatment gave, in 94% recovery, purified product that was 99.67% pure by HPLC (mp 143–144° C.).

2. Preparation of (2-methyl-3-amino-4-chlorophenoxy)acetonitrile

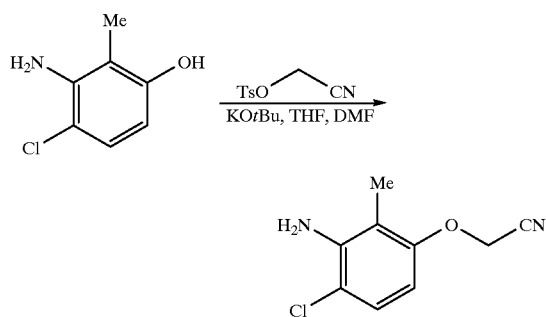

To a solution of potassium tert-butoxide (KOtBu) (7.15 g) in 4:1 tetrahydrofuran (THF)/N,N-dimethylformamide (DMF) (36 mL) was added a solution of 3-amino-4-chloro-o-cresol (10.0 g) in the same solvent system (20 mL) at a rate such that the reaction temperature did not exceed 25° C. After 30 min, a solution of cyanomethyl tosylate (13.00 g) in in 4:1 tetrahydrofuran/N,N-dimethylformamide (16 mL) was slowly added to the phenoxide solution, keeping the temperature at or below 25° C. The resultant slurry was stirred for 3 h, at which point TLC analysis indicated complete reaction. The crude mixture was partitioned between toluene (100 mL) and water (100 mL), and the aqueous phase was extracted with a 50 mL portion of toluene. The combined organics were washed with 1N NaOH and water, then concentrated to an oil (11.81 g, 97.6% crude yield). The crude product was typically carried directly into the next step without purification. Alternatively, the product could be recrystallized from a mixture of toluene and cyclohexane to give a pale tan crystalline solid (>98% pure by HPLC).

3. Preparation of N-(6-chloro-3-cyanomethoxy-2-methylphenyl)-methanesulfonamide

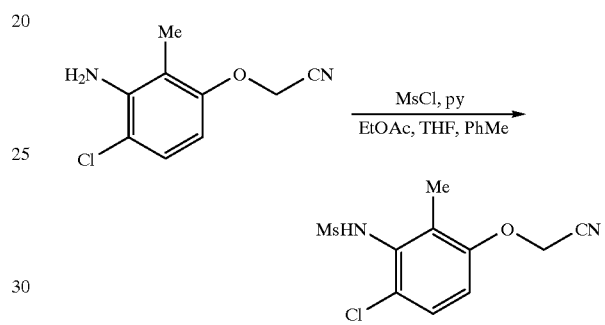

To a solution of crude (2-methyl-3-amino-4-chlorophenoxy)acetonitrile (11.53 g) in toluene (PhMe) (60 mL) was added methanesulfonyl chloride (MsCl) (4.5 mL, 6.7 g) and the resultant solution was warmed to 35–40° C. Pyridine (py) (4.7 mL, 4.6 g) was then added slowly over 2 h. The resultant mixture was permitted to cool to ambient temperature and stirred for 24 h. The crude product mixture was then partitioned between 1N hydrochloric acid (100 mL), and a mixture of ethyl acetate (300 mL) and tetrahydrofuran (100 mL). The organic phase was washed with water, then concentrated to ca. 200 mL, leading to crystallization of the desired product. The white crystalline product was collected, rinsed with toluene, and dried to afford 10.40 g (65.1% field) of N-(6-chloro-3-cyanomethoxy-2-methylphenyl)-methanesulfonamide (>97% pure by HPLC). This material could optionally be recrystallized from isopropanol.

4. Preparation of N-[6-chloro-3-(4,5-dihydro-1-H-imidazol-2-yl-methoxy-2-ethylphenyl]-methanesulfonamide hydrochloride

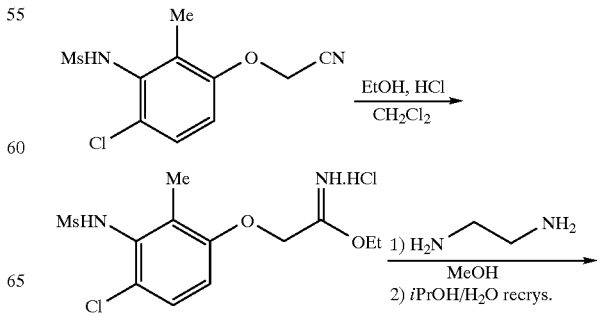

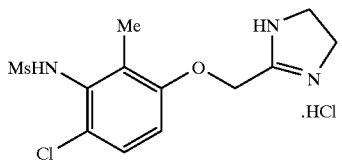

Gaseous hydrogen chloride was bubbled through a suspension of of N-(6-chloro-3-cyanomethoxy-2-methylphenyl)-methanesulfonamide (10.0 g) in a mixture of dichloromethane (100 mL) and ethanol (2.5 mL) for 5 min (to saturation), keeping the temperature below 15° C. The resultant mixture was stirred at ambient temperature for 2 h, during which time the intermediate imidate ester hydrochloride precipitates. Excess hydrogen chloride was purged from the reaction vessel by nitrogen, and the resultant slurry was completely dissolved by the addition of methanol (40 mL). This solution was then added over 15 min to a solution of ethylene diamine (2.4 mL, 2.2 g) in methanol (40 mL), keeping the temperature below 25° C. The desired product salt began to spontaneously precipitate from the reaction mixture within 5 min. After 1 h, the solvent was replaced by a 4:1 mixture of isopropanol and water (100 mL) via distillation. After concentrating the mixture to ca. 90 mL, the resultant slurry was cooled, and the crystalline product was collected. After rinsing with isopropanol, the solid was dried to provide 8.69 g of N-[6-chloro-3-(4,5-dihydro-1-H-imidazol-2-yl-methoxy-2-methylphenyl]-methanesulfonamide hydrochloride (68.3% yield, 98.6% pure by HPLC). This material may optionally be recrystallized from 4:1 isopropanol/water.

Example 3

Preparation of N-[3-(1H-imidazol-4-ylmethyl-2-methyl-pheny]-methanesulfonamide

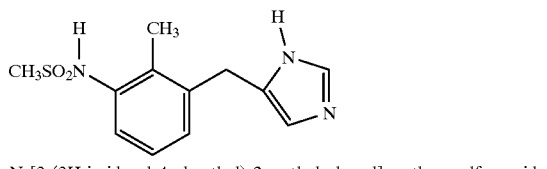

N-[3-(3H-imidazol-4-ylmethyl)-2-methyl-phenyl]-methanesulfonamide

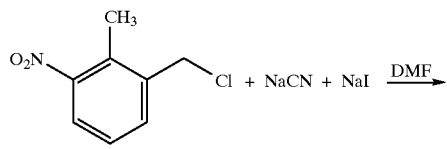

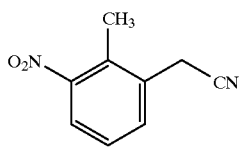

1-Chloromethyl-2-methyl-3-nitro-benzene (25g) was dissolved in 125 ml of N,N-dimethylformamide. To this mixture was added 10.89 g of sodium cyanide (Mallinckrodt, Paris, Ky.) and 0.4 g of sodium iodide (Mallinckrodt) and the heterogeneous mixture was heated to 80° C. for 21 hr. The reaction mixture was cooled to room temperature, poured into ether, washed several times with water, dried, and evaporated. The residue was purified by flash chromatography on silica gel eluting with dichloromethane, giving 16.83 g of (2-methyl-3-nitro-phenyl)-acetonitrile as a cream solid.

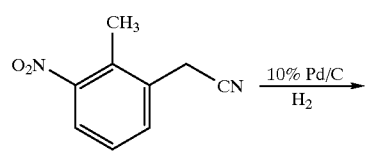

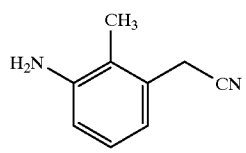

(2-Methyl-3-nitro-phenyl)-acetonitrile (16.6g ) was dissolved in 400 ml of ethyl acetate and 0.83g of 10% palladium on carbon (Degussa type) was added; and the reaction mixture was placed under 50 lb/in² of hydrogen on the Parr shaker for 4 hr. The catalyst was filtered off; the solvent was evaporated; and the residue was purified by flash chromatography on silica gel eluting with ethyl acetate:hexane (2:3), yielding 11.1 g of (3-amino-2-methyl-phenyl)-acetonitrile as a white solid.

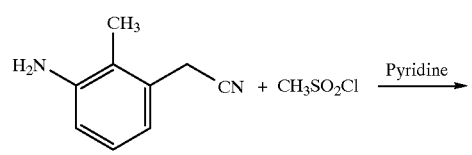

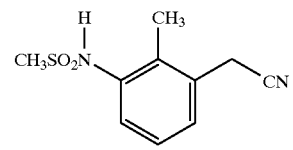

(3-Amino-2-methyl-phenyl)-acetonitrile (11.1 g) was dissolved in 80 ml of pyridine. The solution was cooled in an ice bath and 11.3g of methanesulfonyl chloride was added. The reaction mixture was removed from the ice bath and stirred at room temperature for 30 minutes; 10 ml of water was added, and the mixture was stirred for 30 minutes, poured into ethyl acetate (EtOAc), washed with cold hydrochloric acid, washed with water, dried, and evaporated to give 16.1 g of N-(3-cyanomethyl-2-methyl-phenyl)-methanesulfonamide as a light yellow solid.

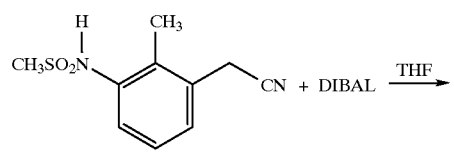

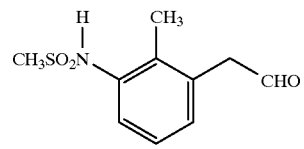

N-(3-cyanomethyl-2-methyl-phenyl)-methanesulfonamide (3.75 g) was dissolved in 50 ml of dry tetrahydrofuran and cooled in an ice bath under an atmosphere of nitrogen. To this mixture was added 67 ml of 1M diisobutylaluminum hydride (DIBAL) in tetrahydrofuran. The mixture was stirred at 5° C. for 75 minutes. Excess reagent was decomposed with methanol and the solvent was evaporated. The residue was treated with EtOAc, washed with cold 1M hydrochloric acid, washed with brine and dried, and the solvent was evaporated. The residue was purified by silica gel chromatography eluting with methanol:dichloromethane (5:95), giving 1.1 g of N-[2-methyl-3 (2-oxo-ethyl)-phenyl]-methanesulfonamide as a yellow oil.

N-[2-Methyl-3(2-oxo-ethyl)-phenyl]-methanesulfonamide (1.08 g) was dissolved in 30 ml of absolute ethanol and 1.02 g of (p-tolylsulfonyl)-methyl isocyanide (TosMIC) and 23 mg of sodium cyanide was added. The reaction mixture was stirred at room temperature for 14 hr. The precipitated solid was filtered, giving 1.24 g of N{2-methyl-3-[4-(toluene-4-sulfonyl)-4,5-dihydro-oxazol-5-methyl-phenyl}-methanesulfonamide as a tan solid.

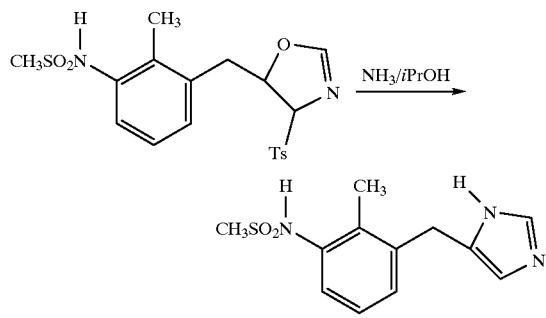

N-{2-methyl-3-[4-(toluene-4-sulfonyl)-4,5-dihydro-oxazol-5-methyl]-phenyl}-methanesulfonamide (1.2 g) was suspended in 15 ml of 2M ammonia in 2-propanol, placed in a sealed tube, and heated at 100° C. for 5 hr. The mixture was evaporated and the residue was purified by flash chromatography on silica gel eluting with methanol:dichloromethane (5:95) giving 437 mg, which was crystallized from ethanol to give 249 mg of N-[3-(3H-imidazol-4-ylmethyl-2-methyl-phenyl]-methanesulfonamide, mp 223.8–224.4° C.

Example 3A

Preparation of N-[3-(3H-imidazol-4-ylmethyl-2,5-dimethyl-phenyl]-methanesulfonamide oxalate

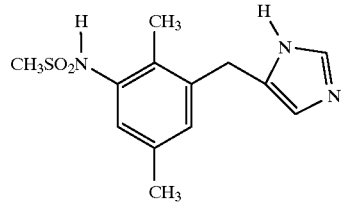

N-[3-(3H-imidazol-4-ylmethyl-2,5-dimethyl-phenyl]-methanesulfonamide oxalate, mp 181.1–182.9° C., was prepared in a manner similar to that described above in Example 3, except starting with 1-chloromethyl-2,5-dimethyl-3-nitro-benzene which was prepared according to the method described by Winchester, et al., *J. Heterocyclic Chemistry* (1975) 12:547.

Example 4

Preparation of N-[5-(3H-imidazol-4-ylmethyl-2-methyl-phenyl]-methanesulfonamide

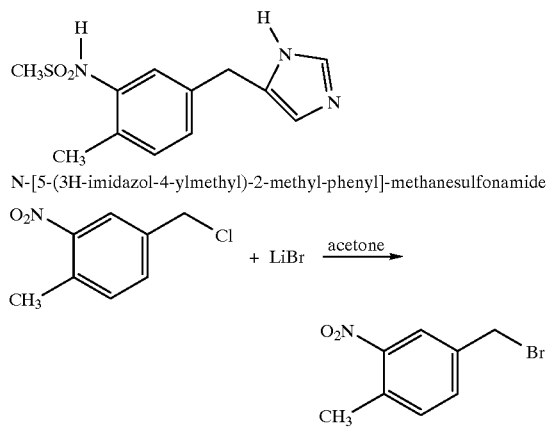

N-[5-(3H-imidazol-4-ylmethyl)-2-methyl-phenyl]-methanesulfonamide

4-Chloromethyl-1-methyl-2-nitro-benzene (5 g) was dissolved in 50 ml of acetone and 23.4 g of lithium bromide was added. The reaction mixture was heated at reflux for 18 hr. The solvent was evaporated off and the residue was tritrated with hexane to give 5.3 g of 4-bromomethyl-1-methyl-2-nitro-benzene as a tan solid.

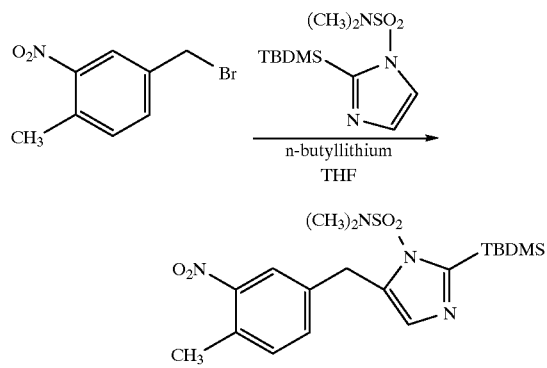

2-(tert-Butyl-dimethyl-silyl)-4,5-dihydro-imidazole-1-sulfonic acid dimethylamide (5.03 g) (prepared as described by Ngochindo, *J. Chem. Soc. Perkin Trans.* (1990) 1:1645) was dissolved in 100 ml of dry tetrahydrofuran and cooled in a dry ice-acetone bath to −78° C.; 11.9 ml of 1.6M n-butyllithium in hexane was added to this mixture. After 1 hr at −78° C., the reaction mixture was treated dropwise with 5.0 g of 4-bromomethyl-1-methyl-2-nitro-benzene dissolved in 25 ml of dry tetrahydrofuran (THF). The mixture was stirred at −78° C. for 1 hr and then allowed to come to room temperature overnight. The mixture was treated with saturated ammonium chloride, extracted with ethyl acetate, washed the combined extracts with saturated sodium chloride, dried, and evaporated to dryness. The residue was purified by flash chromatography on silica gel and eluted with ethyl acetate:hexane (1:4) to give 2.39 g of 2-(tert-butyl-dimethyl-silyl)-5-(4-methyl-3-nitro-benzyl)-imidazole-1-sulfonic acid dimethylamide as a yellow oil.

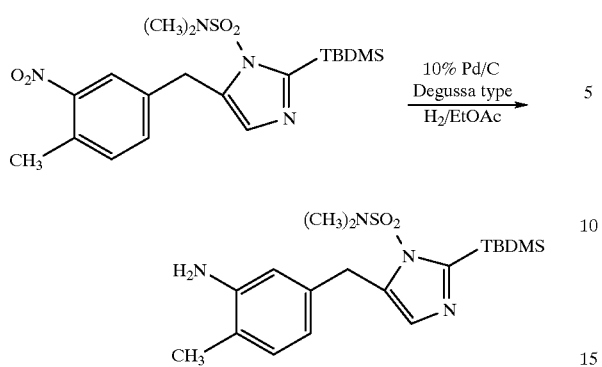

2-(tert-Butyl-dimethyl-silyl)-5-(4-methyl-3-nitro-benzyl)-imidazole-1-sulfonic acid dimethylamide (2.32 g) was dissolved in 125 ml of ethyl acetate and 0.50 g of 10% palladium over charcoal (Pd/C) was added. The reaction mixture was hydrogenated on a Parr shaker at 44 lb/in² for 14 hr. The catalyst was removed by filtration and the solvent was evaporated. The residue was purified by silica gel chromatography eluting with ethyl acetate:hexane (1:3), giving 1.05 g of 5-(3-amino-4-methyl-benzyl)-2-(tert-butyl-dimethyl-silyl)-imidazole-1-sulfonic acid dimethylamide as a white solid.

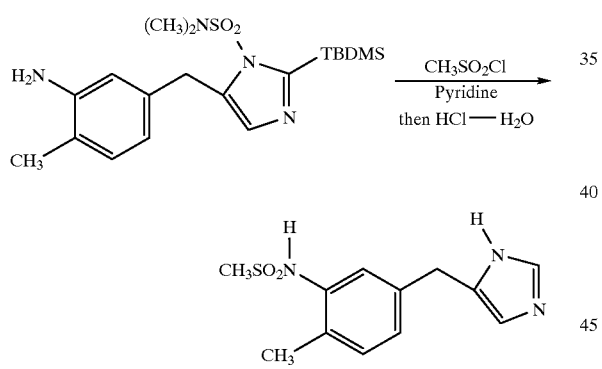

5-(3-Amino-4-methyl-benzyl)-2-(tert-butyl-dimethyl-silyl)-imidazole-1-sulfonic acid dimethylamide (1.02 g) was dissolved in 7 ml of pyridine, cooled in an ice bath, and 0.34 g of methanesulfonyl chloride was added. After stirring the reaction mixture at 5° C. for 1 hr, 2 ml of water was added and the mixture was evaporated to a small volume, dissolved in ethyl acetate, washed with water, dried, and evaporated, leaving 0.85 g of brown oil. The residue was dissolved in 25 ml of methanol, treated with 2 ml of 6M hydrochloric acid, and heated at 70° C. for 16 hr. The solvent was evaporated and the residue was purified by flash chromatography on silica gel eluting with ethyl acetate:methanol:isopropyl amine (92:5:3) giving 0.42 g, which was crystallized from ethanol to give 0.31 g of N-[5-(3H-imidazol-4-ylmethyl)-2-methyl-pheny]-methanesulfonamide, mp 170.1–170.4° C.

Example 5

Preparation of N-[3-(4,5-dihydro-1H-imidazol-2-ylmethyl)-phenyl]-methanesulfonamide hydrochloride

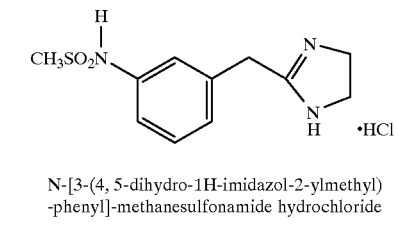

N-[3-(4, 5-dihydro-1H-imidazol-2-ylmethyl)-phenyl]-methanesulfonamide hydrochloride

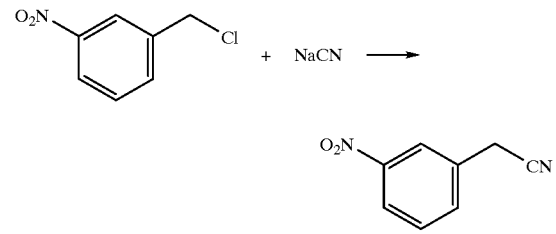

1-Chloromethyl-3-nitro-benzene (5 g) and 4.28 g of sodium cyanide were dissolved in a mixture of 15 ml of water and 50 ml of dioxane and the two phase mixture was heated to 100° C. for 12 hr. The dioxane was removed by evaporation and the aqueous solution was extracted with dichloromethane. The organic extract was washed with brine, dried, and evaporated. The residue was purified by flash column chromatography eluting with EtOAc:hexane (1:4) to afford 2.86 g of a tan solid, mp 51.7–52.7° C., of (3-nitro-phenyl)-acetonitrile.

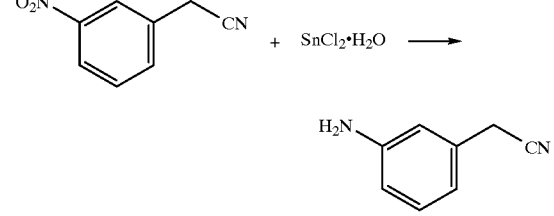

(3-Nitro-phenyl)-acetonitrile (2.79 g) was dissolved in 50 ml of ethyl acetate and the mixture was treated with 19.5 g of tin (II) chloride dihydrate and stirred at room temperature for 72 hr. The mixture was diluted with ethyl acetate and treated with saturated sodium bicarbonate solution, separated, and extracted with ethyl acetate. The extracts were combined, dried, and evaporated, leaving 2.1 g of tan oil of (3-amino-phenyl)-acetonitrile.

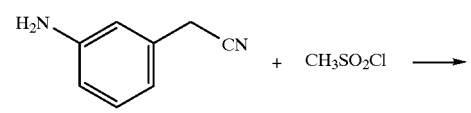

-continued

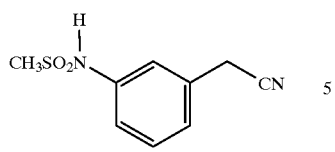

(3-Amino-phenyl)-acetonitrile (2.9 g) was dissolved in 8 ml of pyridine, cooled in an ice bath, treated with 2.6 g of methanesulfonyl chloride, and stirred at room temperature for 1 hr. The reaction mixture was diluted with ethyl acetate, washed with hydrochloric acid, then with brine, dried over magnesium sulfate, and evaporated giving 2.6 g of cream solid of N-(3-cyanomethyl-phenyl)-methanesulfonamide.

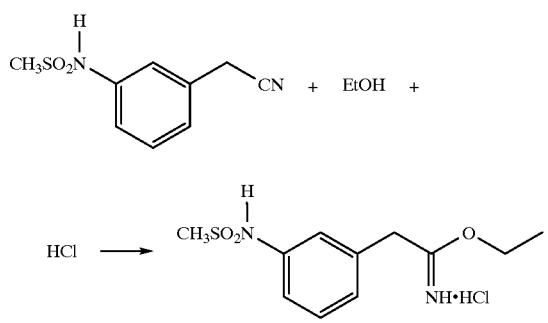

N-(3-cyanomethyl-phenyl)-methanesulfonamide (1.5 g) was dissolved in 50 ml of dichloromethane and 0.49 ml of ethyl alcohol and cooled in an ice bath. Hydrogen chloride gas was added by bubbling until a saturated solution was formed. The mixture was stirred at 5° C. for 1 hr. and then at room temperature for 14 hr. The solvent was evaporated to give 2.2 g of white solid of 2-(3-methanesulfonylamino-phenyl)-acetimidic acid ethyl ester hydrochloride.

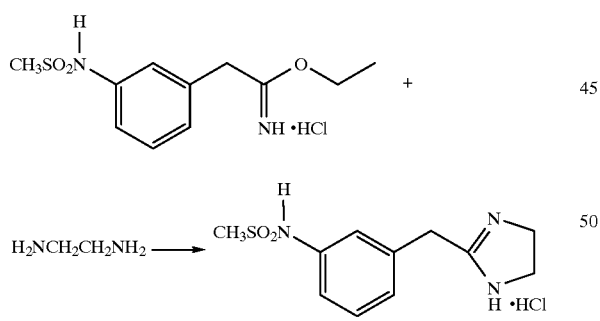

2-(3-Methanesulfonylamino-phenyl)-acetimidic acid ethyl ester hydrochloride (2.1 g) was dissolved in 30 ml of ethyl alcohol, treated with 0.51 g of ethylene diamine, and stirred at room temperature for 16 hr. The solvent was evaporated and the residue was purified by flash chromatography on silica gel eluting with methyl alcohol:dichloromethane (15:85) to give the free base which was converted to the hydrochloride salt by the addition of 1M hydrogen chloride in ether, N-[3-(4,5-dihydro-1H-imidazol-2-ylmethyl)-phenyl]-methanesulfonamide hydrochloride, mp 194.8–195.2° C.

Example 5A

Preparation of N-[3-(4,5-dihydro-1H-imidazol-2-ylmethyl)-2-methyl-phenyl]-methanesulfonamide hydrochloride

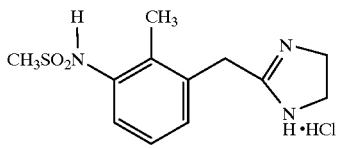

N-[3-(4,5-dihydro-1H-imidazol-2-ylmethyl)-2-methyl-phenyl]-methanesulfonamide hydrochloride, mp 185.3–185.5° C., was prepared in a manner similar to that described above in Example 5, except that the starting material was 1-chloromethyl-2-methyl-3-nitro-benzene.

Example 5B

Preparation of N-[5-(4,5-dihydro-1H-imidazol-2-ylmethyl)-2-methyl-phenyl]-methanesulfonamide hydrochloride

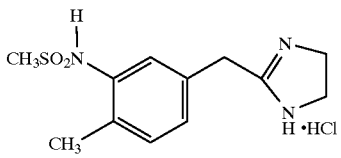

N-[5-(4,5-Dihydro-1H-imidazol-2-ylmethyl)-2-methyl-phenyl]-methanesulfonamide hydrochloride, mp 262–263° C., was prepared in a similar manner to that described above in Example 5, except the starting material was 1-chloromethyl-4-methyl-3-nitro-benzene.

Example 5C

Preparation of N-[3-(4,5-dihydro-1H-imidazol-2-ylmethyl)-5-methyl-phenyl]-methanesulfonamide hydrochloride N-[3-(4,5-dihydro-1H-imidazol-2-ylmethyl)-5-methyl-phenyl]-methanesulfonamide hydrochloride, mp 182.9–183.4° C., was prepared in a manner similar to that described above for Example 5, except starting with 1-bromomethyl-3-methyl-5-nitro-benzene which was prepared according to the method described by Makosza, et al., *Tetrahedron* (1984) 40:1863.

Example 5D

Preparation of N-[3-(4,5-dihydro-1H-imidazol-2-ylmethyl)-2,6-dimethyl-phenyl]-methanesulfonamide hydrochloride

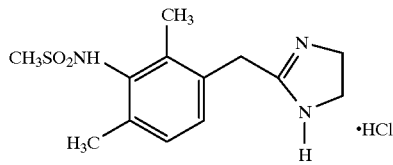

N-[3-(4,5-dihydro-1H-imidazol-2-ylmethyl)-2,6-dimethyl-phenyl]-methanesulfonamide hydrochloride, mp 245–245.7° C., was prepared in a manner similar to that described above for Example 5, except starting with 1-chloromethyl-2,4-dimethyl-3-nitro-benzene which was prepared according to the method described by Goldstein, et al., *J. Org. Chem.* (1984) 49:1613.

Example 5E

Preparation of N-[3-(4,5-dihydro-1H-imidazol-2ylmethyl)-2,5-dimethyl-phenyl]-methanesulfonamide hydrochloride

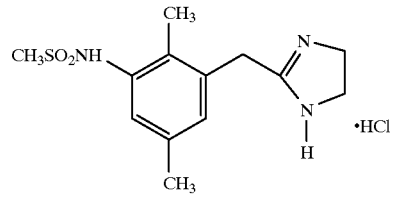

N-[3-(4,5-dihydro-1H-imidazol-2ylmethyl)-2,5-dimethyl-phenyl]-methanesulfonamide hydrochloride, mp 177–178.5° C., was prepared in a manner similar to that described above for Example 5, except starting with 1-chloromethyl-2,5-dimethyl-3-nitro-benzene which was prepared according to the method described by Winchester, et al., *J. Het. Chem.* (1975) 12:547.

Example 5F

Preparation of N-[3-(4,5-dihydro-1H-imidazol-2-ylmethyl)-2,4-dimethyl-phenyl]-methanesulfonamide hydrochloride

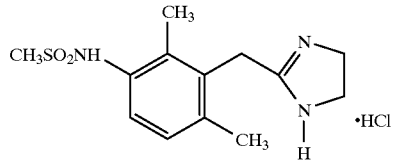

N-[3-(4, 5-dihydro-1H-imidazol-2-ylmethyl)
-2, 4-dimethyl-phenyl]-methanesulfonamide
hydrochloride

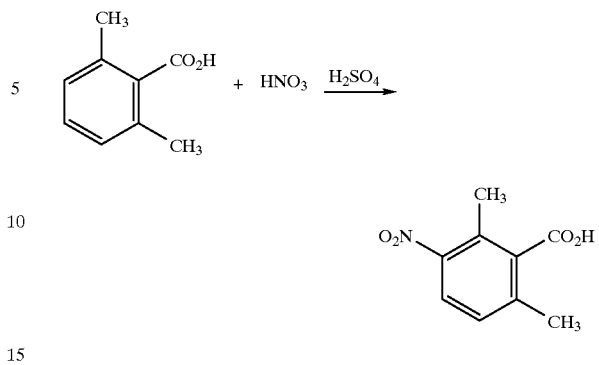

2,6-Dimethylbenzoic acid (15 g) dissolved in 350 ml of nitromethane was cooled in an ice bath and treated with 18.9 ml of 70% nitric acid and then 14 ml of concentrated sulfuric acid. The bath was removed and the mixture was stirred at room temperature for 22 hr. The mixture was poured into ethyl acetate, washed several times with water, dried, evaporated, and 17.2 g of 2,6-dimethyl-3-nitrobenzoic acid, mp 115.9–116.5° C., was obtained.

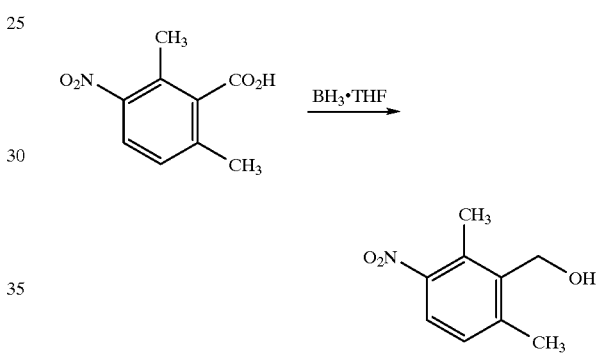

2,6-Dimethyl-3-nitrobenzoic acid (10 g) was dissolved in 100 ml of dry tetrahydrofuran and 165 ml of 1M borane in tetrahydrofuran added. The mixture was heated to 75° C. for 4 hr. The mixture was cooled to room temperature and the excess reagent slowly decomposed with water and the solvent evaporated. The residue was treated with ethyl acetate, washed with 1M hydrochloric acid, then with water, dried, and evaporated to give 8.71 g of (2,6-dimethyl-3-nitro-phenyl)-methanol, mp 94.5–96.1° C.

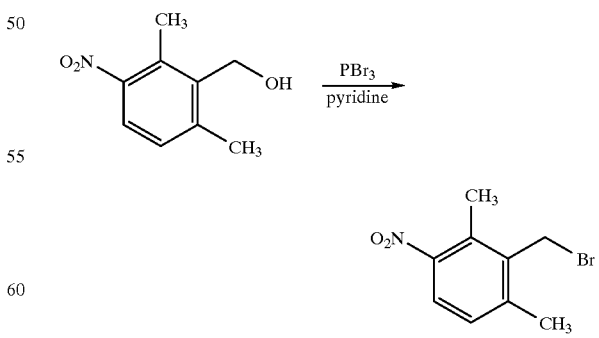

(2,6-Dimethyl-3-nitro-phenyl)-methanol (7.3 g) was dissolved in 73 ml of dichloromethane and 3.6 ml of pyridine added. The mixture was cooled in an ice bath, 12.3 g of phosphorus tribromide added, and stirred at 5° C. for 30 minutes. The mixture was poured into ethyl acetate, washed twice with brine, dried over magnesium sulfate, evaporated to dryness, and 8.3 g of crude 2-bromomethyl-1,3-dimethyl-4-nitro-benzene obtained as a cream solid.

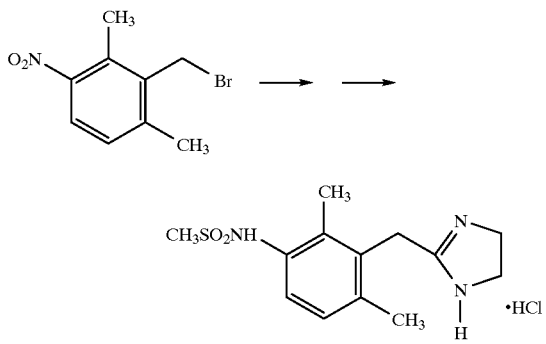

N-[3-(4,5-Dihydro-1H-imidazol-2-ylmethyl)-2,4-dimethyl-phenyl]-methanesulfonamide hydrochloride, mp 107–124° C., was prepared in a manner similar to that described above for Example 5, except starting with 2-bromomethyl-1,3-dimethyl-4-nitro-benzene.

Example 5G

Preparation of N-[5-(4,5-dihydro-1H-imidazol-2-ylmethyl)-2-fluoro-phenyl]-methanesulfonamide hydrochloride

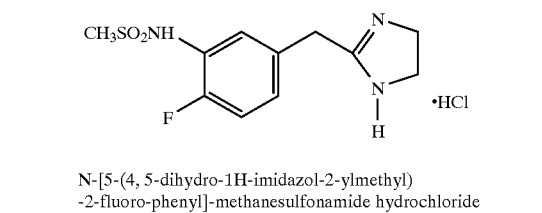

N-[5-(4, 5-dihydro-1H-imidazol-2-ylmethyl)
-2-fluoro-phenyl]-methanesulfonamide hydrochloride

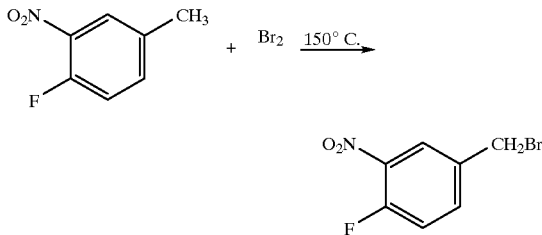

To a stirred melt of 1-fluoro-4-methyl-2-nitro-benzene (10 g) at 150° C. under a sunlamp was slowly added 3.65 ml of bromine over a 5 hr period. Cooled the brown mixture to 50° C. and poured into 125 ml of hexane. Cooled in an ice bath, filtered, and obtained 10.1 g of 4-bromomethyl-1-fluoro-2-nitro-benzene as white crystals.

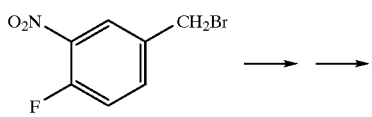

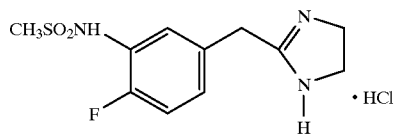

N-[5-(4,5-Dihydro-1H-imidazol-2-ylmethyl)-2-fluoro-phenyl]-methanesulfonamide hydrochloride, mp 205.2–205.7° C., was prepared in a manner similar to that described above for Example 5, except starting with 4-bromomethyl-1-fluoro-2-nitrobenzene.

Example 5H

Preparation of N-[3-(3,4-dihydro-1H-imidazol-2-ylmethyl)-4-fluoro-phenyl]-methanesulfonamide hydrochloride

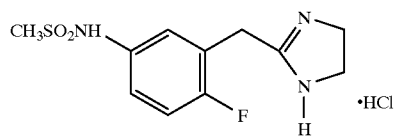

N-[3-(3,4-dihydro-1H-imidazol-2-ylmethyl)-4-fluoro-phenyl]-methanesulfonamide hydrochloride, mp 245.4–245.7° C., was prepared in a manner similar to that described above for Example 5, except starting with 2-bromomethyl-1-fluoro-4-nitro-benzene which was prepared according to the method described by O'Neill, et al., *J. Med. Chem.* (1994) 37:1362.

Example 5I

Preparation of N-[2-chloro-3-(4,5-dihydro-1H-imidazol-2-ylmethyl)-phenyl]-methanesulfonamide hydrochloride

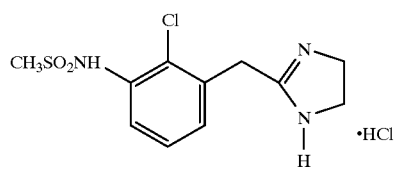

N-[2-Chloro-3-(4,5-dihydro-1H-imidazol-2-ylmethyl)-phenyl]-methanesulfonamide hydrochloride, mp 199.9–201.0° C., was prepared in a manner similar to that described above for Example 5, except starting with 1-bromomethyl-2-chloro-3-nitrobenzene which was prepared according to the method described by Uneme, et al., *Biosci. Biotechnol. Biochem.* (1992) 56:2023.

Example 5J

Preparation of N-[5-(4,5-dihydro-1H-imidazol-2ylmethyl)-2-chloro-phenyl]-methanesulfonamide hydrochloride

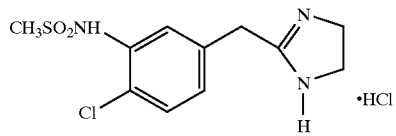

N-[5-(4,5-dihydro-1H-imidazol-2-ylmethyl)-2-chloro-phenyl]-methanesulfonamide hydrochloride, mp 238.9–240.4° C., was prepared in a manner similar to that described above for Example 5, except starting with 4-bromomethyl-1-chloro-2-nitrobenzene which was prepared according to the method described by Kelley, et al., *J. Med. Chem.* (1989) 32:1757.

Example 5K

Preparation of N-[3-bromo-5-(4,5-dihydro-1H-imidazol-2-ylmethyl)-phenyl]-methanesulfonamide hydrochloride

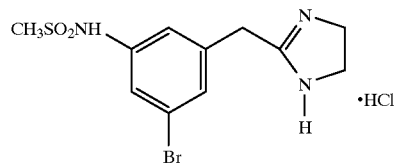

N-[3-Bromo-5-(4, 5-dihydro-1H-imidazol-2-ylmethyl)-phenyl]-methanesulfonamide hydrochloride

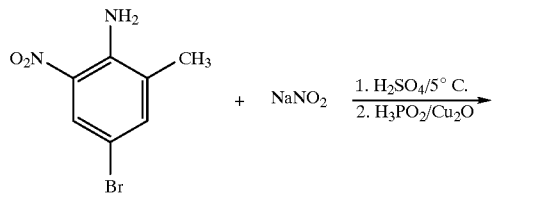

A solution of 10 g of 4-bromo-2-methyl-6-nitrophenylamine in 100 ml of concentrated sulfuric acid in an ice bath was treated dropwise with 3.58 g of sodium nitrite in 10 ml of water keeping the temperature below 10° C. The mixture was then treated simultaneously over 1 hr with 6.81 g of copper (I) oxide and 31.4 ml of hypophosphorus acid. Poured into ice water, extracted with ether, washed with water, dried over magnesium sulfate, and evaporated to dryness. The residue was purified by flash column chromatography on silica gel eluting with ethyl acetate/hexane (1:9) giving 7.73 g of 1-bromo-3-methyl-5-nitrobenzene.

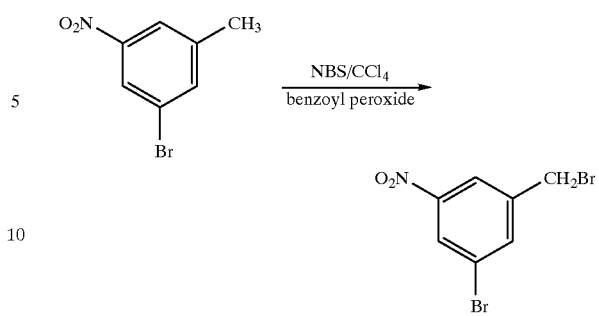

A solution of 7.68 g of 1-bromo-3-methyl-5-nitrobenzene, 6.64 g of N-bromosuccinimide, and 86 mg of benzoyl peroxide in 100 ml of carbon tetrachoride was heated to 90° C. for 16 hr, cooled to room temperature, filtered, evaporated the filtrate, and 11 g of crude 1-bromo-3-bromomethyl-5-nitrobenzene obtained as a brown, partially crystallized oil. Used this oil without purification.

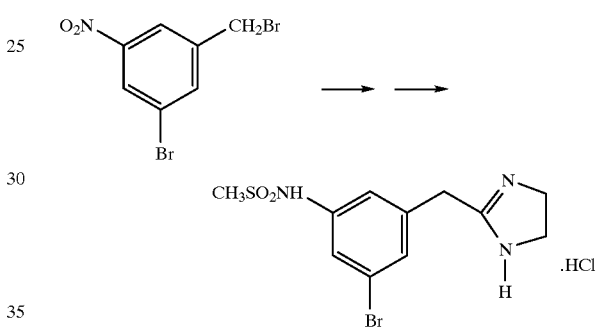

N-[3-Bromo-5-(4,5-dihydro-1H-imidazol-2-ylmethyl)-phenyl]-methanesulfonamide hydrochloride, mp 216.9–217.5° C., was prepared in a manner similar to that described above for Example 5, except starting with 1-bromo-3-bromomethyl-5-nitrobenzene.

Example 5L

Preparation of N-[3-(4,5-dihydro-1H-imidazol-2-ylmethyl)-2-methoxy-phenyl]-methanesulfonamide hydrochloride

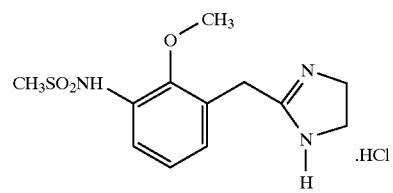

N-[3-(4,5-dihydro-1H-imidazol-2-ylmethyl)-2-methoxy-phenyl]-methanesulfonamide hydrochloride

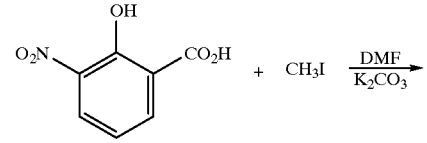

-continued

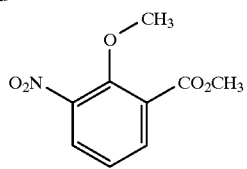

A solution of 15 g of 2-hydroxy-3-nitro-benzoic acid in 200 ml of N,N-dimethylformamide was treated with 58.1 g of iodomethane and 56.6 g of potassium carbonate, and the resultant heterogeneous mixture was stirred and heated to 45° C. for 20 hr. The mixture was cooled to room temperature, poured into ether, washed with water, washed with saturated sodium carbonate solution, washed with water, dried over magnesium sulfate, evaporated, and 14.2 g of 2-methoxy-3-nitro-benzoic acid methyl ester obtained as an oil which crystallized to a white solid.

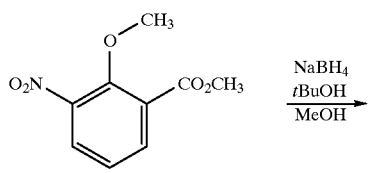

A solution of 14.0 g of 2-methoxy-3-nitro-benzoic acid methyl ester in 245 ml of tert-butanol was treated with 6.75 g of sodium borohydride, and the heterogeneous mixture to 80° C. Methonol (62 ml) was slowly added at a dropwise rate over 2 hr. After 3 hr at 80° C., the solvent was evaporated at 40° C. under reduced pressure and the residue was treated with water, acidified with hydrochloric acid, extracted with ethyl acetate, the extracts washed with brine, dried, and evaporated to dryness. Purification of the residue by flash column chromatography on silica gel afforded 8.3 g of (2-methoxy-3-nitro-phenyl)-methanol as a brown solid.

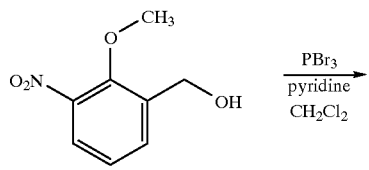

A solution of 14.7 g of (2-methoxy-3-nitro-phenyl)-methanol dissolved in 140 ml of dichloromethane and 5.5 ml of pyridine was cooled in an ice bath and slowly added 6.48 ml of phosphorus tribromide. After 45 minutes at 5° C., the reaction mixture was diluted with dichloromethane, washed with water, dried, and evaporated to dryness. The residue was purified by flash chromatography on silica gel eluting with ethyl acetate/hexane (5:95) giving 7.3 g of 1-bromomethyl-2-methoxy-3-nitrobenzene as a yellow solid.

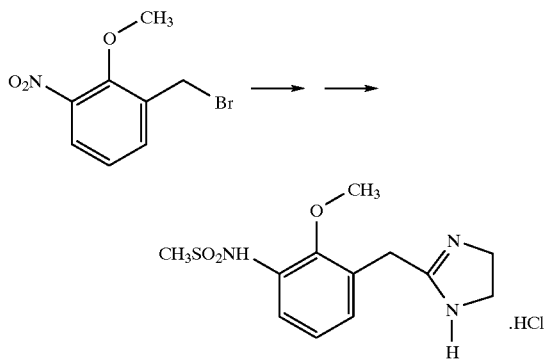

N-[3-(4,5-Dihydro-1H-imdazol-2-ylmethyl)-2-methoxy-phenyl]-methanesulfonamide hydrochloride, mp 207.6–208.1° C., was prepared in a manner similar to that described above for Example 5, except starting with 1-bromomethyl-2-methoxy-3-nitrobenzene.

Example 5M

Preparation of N-[5-(4,5-dihydro-1H-imidazol-2-ylmethyl)-2-methoxy-phenyl]-methanesulfonamide hydrochloride

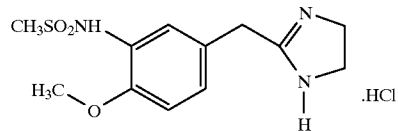

N-[5-(4,5-Dihydro-1H-imidazol-2-ylmethyl)-2-methoxy-phenyl]-methanesulfonamide hydrochloride, mp 201.2–201.5° C., was prepared in a manner similar to that described above for Example 5, except starting with 4-bromomethyl-1-methoxy-2-nitrobenzene which was prepared according to the method described in Shoesmith, et al., J. Chem. Soc. (1924) 125:1317.

Example 5N

Preparation of N-[5-(4,5-dihydro-1H-imidazol-2-ylmethyl)-2-hydroxy-phenyl]-methanesulfonamide hydrobromide

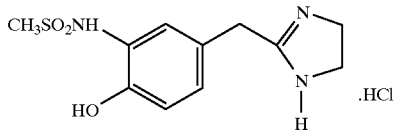

N-[5-(4,5-dihydro-1H-imidazol-2-ylmethyl)-2-hydroxy-phenyl]-methanesulfonamide hydrobromide -continued

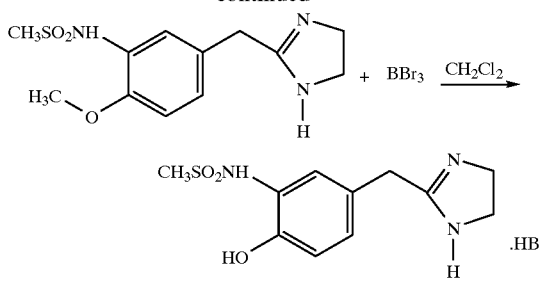

A solution of 420 mg of N-[5-(4,5-dihydro-1H-imidazol-2-ylmethyl)-2-methoxy-phenyl]-methanesulfonamide (free base) in 24 ml of dichloromethane was cooled in an ice bath and treated with 10.3 ml of 1M boron tribromide in dichloromethane. Removed the ice bath, stirred at room temperature for 3 hr, added methanol, and evaporated. The residue was purified by flash chromatography on silica gel eluting with dichloromethane/methanol/concentrated ammonium hydroxide (85:5:3) and crystallized from ethanol/ether to afford 58 mg of N-[5-(4,5-dihydro-1H-imidazol-2-ylmethyl)-2-hydroxy-phenyl]-methanesulfonamide hydrobromide, mp 209–209.5° C.

Example 50

N-[3-chloro-5-(4,5-dihydro-1H-imidazol-2-ylmethyl)-2-methylphenyl]-methanesulfonamide hydrochloride

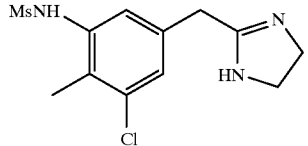

1. Preparation of 3-amino-4-methyl-5-nitrobenzoic acid

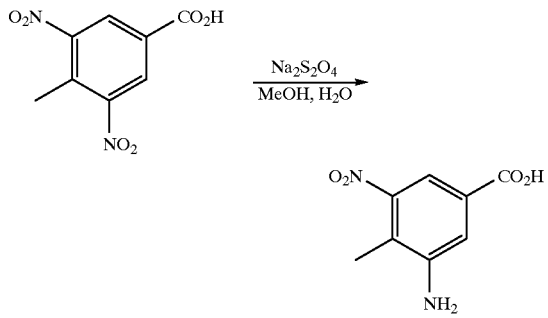

3-Amino-4-methyl-5-nitrobenzoic acid was prepared from 4-methyl-3,5-benzoic acid in a manner similar to that described in Example 6D for the preparation of 5-chloro-2-methyl-3-nitrophenylamine from 5-chloro-2-methyl-1,3-dintrophenylamine.

2. Preparation of 3-chloro-4-methyl-5-nitro benzoic acid

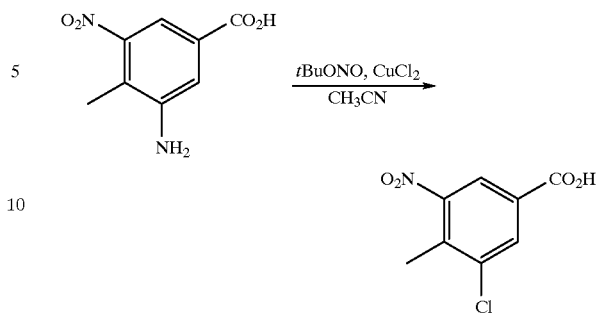

3-Chloro-4-methyl-5-nitro benzoic acid was prepared from 3-amino-4-methyl-5-nitrobenzoic acid in a manner similar to that described in Example 24 for the preparation of 3-chloro-2,6-dintrotoluene from 2,4-dinitro-3-methyl aniline.

3. Preparation of (3-chloro-4-methyl-5-nitrophenyl) methanol

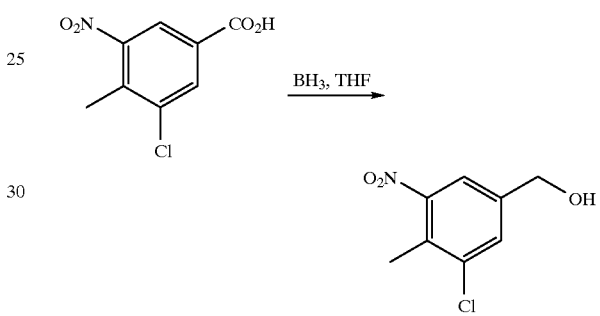

4.2 g of 3-chloro-4-methyl-5-nitro benzoic acid was dissolved in 20 ml dry THF and the solution was cooled to 0° C. BH$_3$-THF (28 ml) solution was added in 2 ml portions. After 1 hr, the reaction mixture was poured onto 100 g of ice containing saturated NaHCO$_3$ solution. The mixture was extracted with ether (3×75 ml). The extracts were washed with brine, dried (anhydrous MgSO$_4$), filtered, and concentrated. The resultant brown oil was applied to a SiO$_2$ column as a solution in toluene and eluted with 25% ethyl acetate in hexane to give 1.96 g of (3-chloro-4-methyl-5-nitrophenyl) methanol.

4. Preparation of 5-bromomethyl-1-chloro-2-methyl-3-nitrobenzene

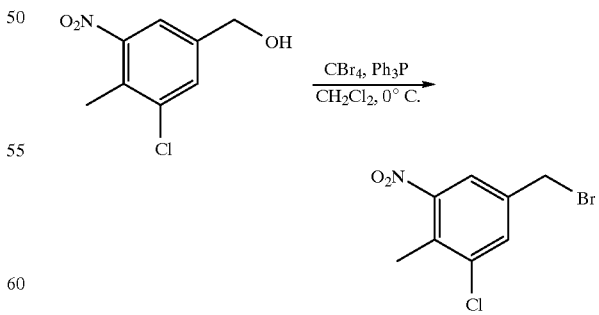

5-Bromomethyl-1-chloro-2-methyl-3-nitrobenzene was prepared from (3-chloro-4-methyl-5-nitrophenyl)methanol in a manner similar to that described in Example 10 for the preparation of N-methanesulfonyl-6-bromomethylindole from N-methanesulfonyl-6-hyroxymethyl indole.

5. Preparation of (3-chloro-4-methyl-5-nitrophenyl) acetonitrile

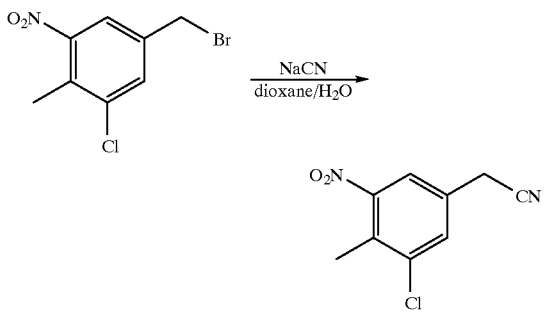

(3-Chloro-4-methyl-5-nitrophenyl) acetonitrile was prepared from 5-bromomethyl-1-chloro-2-methyl-3-nitrobenzene in a manner similar to that described in Example 10 for the preparation of N-methanesulfonyl-6-cyanomethyl indole from N-methanesulfonyl-6-bromomethyl indole.

6. Preparation of (3-amino-5-chloro-4-methylphenyl) acetonitrile

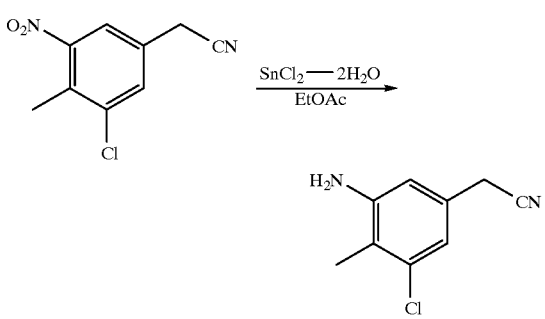

(3-Amino-5-chloro-4-methylphenyl) acetonitrile was prepared from (3-chloro-4-methyl-5-nitrophenyl) acetonitrile in a manner similar to that described in Example 2 for the preparation of (3-amino-4-methylphenoxy) acetonitrile from (4-methyl-3-nitrophenoxy) acetonitrile.

7. Preparation of N-(3-chloro-5-cyanomethyl-2-methylphenyl) methanesulfonamide

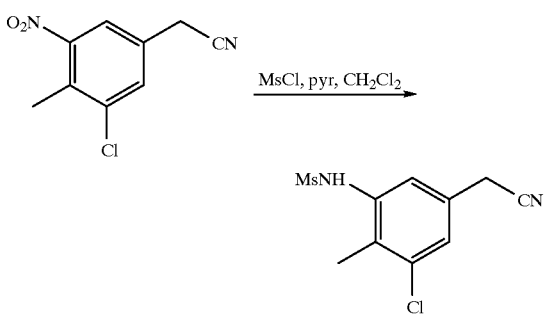

wherein Ms = CH$_3$SO$_2$

N-(3-chloro-5-cyanomethyl-2-methylphenyl) methanesulfonamide was prepared from (3-amino-5-chloro-4-methylphenyl) acetonitrile in a manner similar to that described in Example 1 for the preparation of N-(3-cyanomethoxyphenyl)-methanesulfonamide from (3-aminophenoxy)-acetonitrile.

8. Preparation of N-[3-chloro-5-(4,5-dihydro-1H-imidazol-2-ylmethyl)-2-methylphenyl]-methanesulfonamide hydrochloride

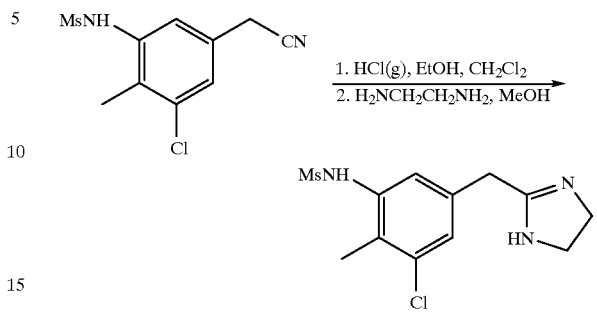

wherein Ms = CH$_3$SO$_2$

N-[3-chloro-5-(4,5-dihydro-1H-imidazol-2-ylmethyl)-2-methylphenyl]methanesulfonamide hydrochloride (mp 256.2–256.7° C.) was prepared from N-(3-chloro-5-cyanomethyl-2-methylphenyl) methanesulfonamide in a manner similar to that described in Example 1 for the preparation of N-[3-(4,5-dihydro-1H-imidazol-2-ylmethoxy)phenyl]methanesulfonamide hydrochloride from (3-aminophenoxy)acetonitrile.

Example 5P

N-[3-bromo-5-(4,5-dihydro-1H-imidazol-2-ylmethyl)-2-methylphenyl]-methanesulfonamide hydrochloride

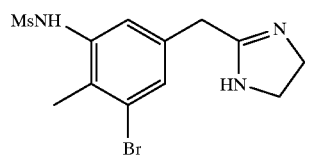

wherein Ms = CH$_3$SO$_2$

N-[3-bromo-5-(4,5-dihydro-1H-imidazol-2-ylmethyl)-2-methylphenyl]methanesulfonamide hydrochloride (mp 262.4–262.8° C.) was prepared from in a manner similar to that described N-[3-chloro-5-(4,5-dihydro-1H-imidazol-2-ylmethyl)-2-methylphenyl]methanesulfonamide hydrochloride, except that copper (II) bromide was used place of copper(II) chloride.

Example 6

Preparation of N-[3-(imidazolidin-2-ylideneamino)-2-methyl-phenyl]-methanesulfonamide

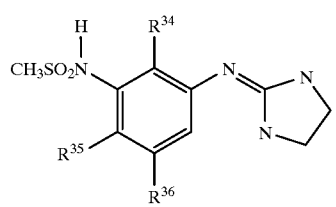

N-[3-(imidazolidin-2-ylideneamino)-2-methyl-phenyl]-methanesulfonamide

1. Preparation of N-(2-methyl-3-nitro-phenyl)-methanesulfonamide and N-(3-amino-2-methyl-phenyl)-methanesulfonamide

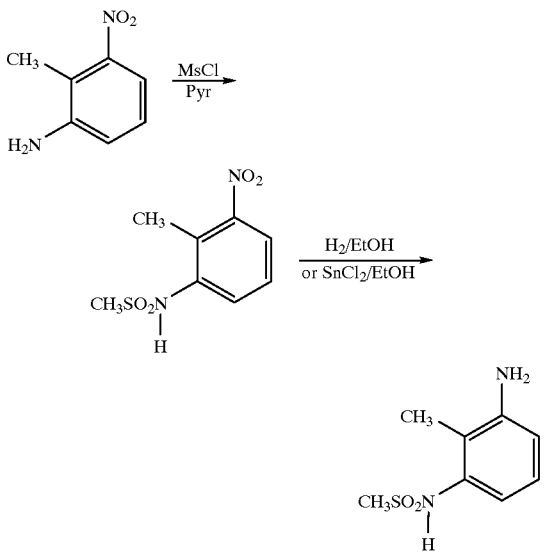

A mixture of 2-methyl-3-nitro-phenylamine (3 g) and methanesulfonyl chloride (1.6 mL) in pyridine (30 mL, from Mallinckrodt) was stirred at room temperature overnight. Pyridine was removed under reduced pressure. The residue was taken up with dichloromethane (Mallinckrodt) and washed with water and brine. After drying over sodium sulfate and evaporation of the solvent, N-(2-Methyl-3-nitro-phenyl)-methanesulfonamide (4 g) was obtained.

A mixture of N-(2-methyl-3-nitro-phenyl)-methanesulfonamide (1.5 g) and tin(II) chloride dihydrate (7.4 g) in ethanol (15 mL) and ethyl acetate (15 mL, from Burdick and Jackson, Muskegon, Mich.) was stirred at room temperature overnight. The reaction mixture was treated with saturated sodium bicarbonate solution to pH>9. The mixture was filtered and the filtrate was washed with water and brine. After drying over anhydrous sodium sulfate and evaporation of solvent, N-(3-amino-2-methyl-phenyl)-methanesulfonamide (1 g) was obtained.

2. Preparation of N-[3-(imidazolidin-2-ylideneamino)-2-methyl-phenyl]-methanesulfonamide

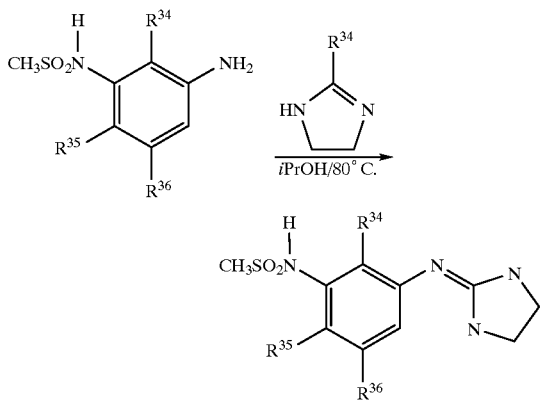

N-[3-(imidazolidin-2-ylideneamino)-2-methyl-phenyl]-methanesulfonamide ($R^{34}$=$CH_3$, $R^{35}$ and $R^{36}$=H) was prepared as follows: 2-Chloro-2-imidazoline sulfate salt (0.5 g, prepared from 2-imidazoline thione and chlorine gas according to the procedure reported by Trani, et al., *J. Heterocycl. Chem.* (1974) 11:257) was treated with 1N NaOH solution (10 mL). 2-Chloro-2-imidazoline was quickly extracted with $CH_2Cl_2$, dried over $K_2CO_3$ and filtered into a flask with N-(3-amino-2-methyl-phenyl)-methanesulfonamide (0.3 g, from above) in isopropyl alcohol (10 mL). The mixture was concentrated in vacuo to about .5–6 ml volume and diluted with isopropyl alcohol (about 10–12 mL). The mixture was then heated at reflux for 4 hr and the solvent was evaporated. The residue was chromatographed on silica gel eluting with ethyl acetate:methanol:isopropyl amine (85:10:5) to isolate the desired product (0.2 g), which was recrystallized from methanol to give pure N-[3-(imidazolidin-2-ylideneamine-2-methyl-phenyl]-methanesulfonamide, mp 243–244° C.

Example 6A

Preparation of N-[3-(imidazolidin-2-ylideneamino)-phenyl]-methanesulfonamide

1. Preparation of N-(3-nitro-phenyl)-methanesulfonamide and N-(5-amino-2-methyl-phenyl)-methanesulfonamide N-(3-nitro-phenyl)-methanesulfonamide and N-(5-amino-2-methyl-phenyl)-methanesulfonamide were prepared in a manner similar to that described above in Example 6, part 1, using 3-nitroaniline as starting material.

2. Preparation of N-[3-(Imidazolidin-2-ylideneamino)-phenyl]-methanesulfonamide

N-[3-(Imidazolidin-2-ylideneamino)-phenyl]-methanesulfonamide ($R^{34}$, $R^{35}$ and $R^{36}$=H), mp 229.1–229.6° C., was prepared in a similar manner to that described above in Example 6, part 2, using N-(5-Amino-2-methyl-phenyl)-methanesulfonamide from above.

Example 6B

Preparation of N-[5-(imidazolidin-2-ylideneamino)-2-methyl-phenyl]-methanesulfonamide 1. Preparation of N-(2-methyl-5-nitro-phenyl)-methanesulfonamide and N-(5-amino-2-methyl-phenyl)-methanesulfonamide N-(2-methyl-5-nitro-phenyl)-methanesulfonamide and N-(5-amino-2-methyl-phenyl)-methanesulfonamide were prepared in a manner similar to that described above in Example 6, part 1, using 2-methyl-5-nitroaniline as starting material.

2. Preparation of N-[5-(imidazolidin-2-ylideneamino)-2-methyl-phenyl]-methanesulfonamide N-[5-(imidazolidin-2-ylideneamino)-2-methyl-phenyl]-methanesulfonamide ($R^{34}$, $R^{35}$=$CH_3$, $R^{36}$=H), mp 123.8–125.5° C., was prepared in a similar manner to that described above in Example 6 except the starting material was N-(5-amino-2-methyl-phenyl)-methanesulfonamide from above.

Example 6C

Preparation of N-[2-chloro-5-(imidazolidin-2-ylideneamino)-phenyl]-methanesulfonamide hydrochloride 1. Preparation of N-(2-chloro-5-nitro-phenyl)-methanesulfonamide and N-(5-amino-2-chloro-phenyl)-methanesulfonamide N-(2-chloro-5-nitro-phenyl)-methanesulfonamide and N-(5-amino-2-chloro-phenyl)-methanesulfonamide were prepared in a manner similar to that described above in Example 6, part 1, using 2-chloro-5-nitroaniline as starting material.

2. Preparation of N-[2-chloro-5-(imidazolidin-2-ylideneamino)-phenyl]-methanesulfonamide hydrochloride N-[2-chloro-5-(imidazolidin-2-ylideneamino)-phenyl]-methanesulfonamide hydrochloride ($R^{34}$=H, $R^{35}$=Cl, $R^{36}$=

H), 253.5–254° C., was prepared in a similar manner to that described above in Example 6, except the starting material was N-(5-amino-2-chloro-phenyl)-methanesulfonamide from above.

Example 6D

Preparation of N-[5-chloro-3-(imidazolidin-2-ylideneamino)-2-methyl-phenyl]-methanesulfonamide

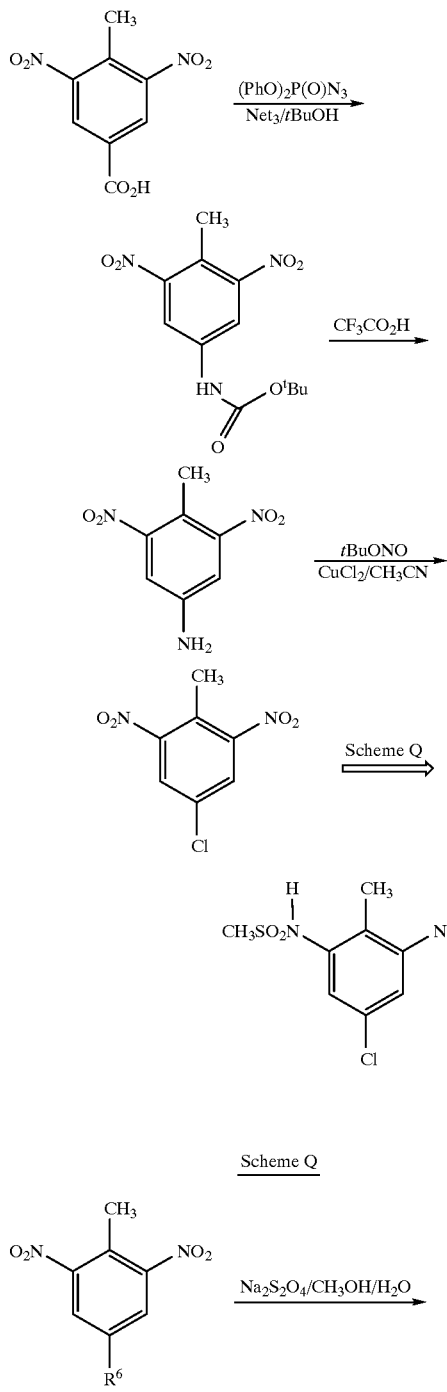

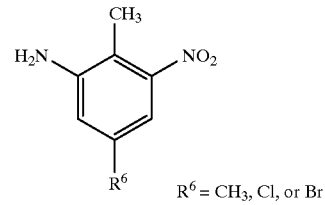

R⁶ = CH₃, Cl, or Br

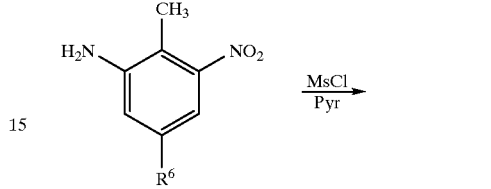

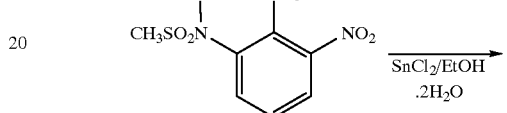

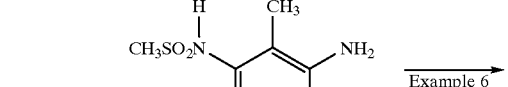

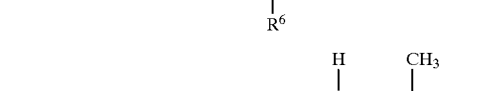

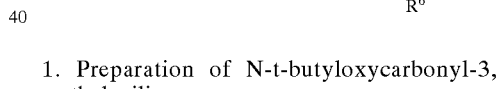

1. Preparation of N-t-butyloxycarbonyl-3,5-dinitro-4-methylaniline

A mixture of 3,5-dinitro-p-toluic acid (20 g), diphenylphosphoryl azide (29.2 g) and triethyl amine (10.7 g, from Mallinckrodt) in tert-butyl alcohol (200 mL) under nitrogen was heated at reflux for 1 hr. The solvent was evaporated under reduced pressure. The residue was partitioned between ethyl acetate (300 mL) and 1N HCl (300 mL). The ethyl acetate solution was washed with half-saturated sodium chloride solution, 1N sodium hydroxide solution (300 mL), and dried over magnesium sulfate. The solvent was evaporated and the residue was chromatographed on silica gel eluting with ethyl acetate:hexane (1:9) to afford N-t-butyloxycarbonyl-3,5-dinitro-4-methylaniline (7.8 g).

2. Preparation of 4-methyl-3,5-dinitro-phenylamine

A mixture of N-t-butyloxycarbonyl-3,5-dinitro-4-methylaniline (7.8 g, from above) and trifluoroacetic acid (100 mL) was stirred at room temperature for 15 min. After evaporation of the solvent under reduced pressure, the residue was taken up in ethyl acetate (100 mL), washed with saturated sodium bicarbonate solution, half-saturated sodium chloride solution, and dried over magnesium sulfate. After evaporation of the solvent, the residue was purified by flash column chromatography on silica gel eluting with acetone:hexane (1:3) to give 4-methyl-3,5-dinitro-phenylamine (2.45 g).

3. Preparation of 5-chloro-2-methyl-1,3-dinitro-benzene

To a mixture of t-butyl nitrite (1.65 g) and copper (II) chloride (1.72 g) in acetonitrile (40 mL, from Mallinckrodt) was added 4-methyl-3,5-dinitro-phenylamine (2.1 g, from above) portionwise over 5 min. The mixture was heated at 65° C. for 10 min and cooled to room temperature. The mixture was partitioned between 6N HCl (200 mL) and diethyl ether (200 mL, from Mallinckrodt). The ether layer was separated and washed with 6N HCl (200 mL) and brine. After drying over magnesium sulfate and evaporation of the solvent, the residue was purified by flash column chromatography on silica gel eluting with ethyl acetate:hexane (5:95) to isolate 5-chloro-2-methyl-1,3-dinitro-benzene (2.2 g).

4. Preparation of 5-chloro-2-methyl-3-nitro-phenylamine

5-Chloro-2-methyl-1,3-dinitro-benzene (1.96 g, from above) was suspended in methanol (80 mL) and water (20 mL) under $N_2$. Sodium dithionite (5.51 g) was added portionwise and the mixture was stirred at room temperature for 3 hr. The reaction mixture was filtered and washed with methanol. The filtrate was then removed under reduced pressure and the residue was partitioned between ethyl acetate (150 mL) and brine (150 mL). The organic layer was dried over magnesium sulfate and evaporated to afford 5-chloro-2-methyl-3-nitro-phenylamine (1.45 g).

5. Preparation of N-[5-chloro-3-(imidazolidin-2-ylideneamino)-2-methyl-phenyl]-methanesulfonamide N-[5-chloro-3-(imidazolidin-2-ylideneamino)-2-methyl-phenyl]-methanesulfonamide ($R^{34}$=$CH_3$, $R^{35}$=H, $R^{36}$=Cl), 230.5–233° C., was prepared in a similar manner to that described above in Example 6, except the starting material was 5-chloro-2-methyl-3-nitro-phenylamine from above.

Example 6E

Preparation of N-[5-bromo-3-(imidazolidin-2-ylideneamino)-2-methyl-phenyl]-methanesulfonamide 1. Preparation of 5-bromo-2-methyl-1,3-dinitro-benzene

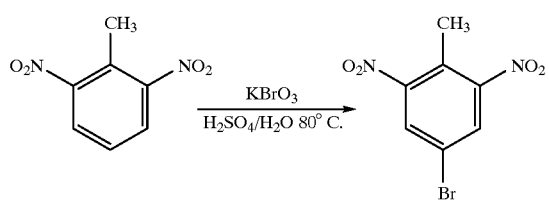

To a mixture of 2-methyl-1,3-dinitro-benzene (10 g) and 1:1 concentrated sulfuric acid-water (100 mL) at 80° C. was added potassium bromate (10.1 g) portionwise over 2–2½ hr. The mixture was stirred at 80° C. for an additional 2 hr and cooled to room temperature. The mixture was poured into 500 g ice and then extracted with diethyl ether (300 mL). The ether layer was washed with 10% sodium bicarbonate solution (250 mL), brine and dried over magnesium sulfate. After evaporation of the solvent, the residue was purified by flash column chromatography on silica gel eluting with ethyl acetate:hexane (4:96) to afford 5-bromo-2-methyl-1,3-dinitro-benzene (5.3 g).

2. Preparation of 5-bromo-2-methyl-3-nitro-phenylamine

This compound was prepared in a manner similar to that described above Example 6D using the 5-bromo-2-methyl-1,3-dinitro-benzene (5.3 g) prepared above.

3. Preparation of N-[5-bromo-3-(imidazolidin-2-ylideneamino)-2-methyl-phenyl]-methanesulfonamide N-[5-bromo-3-(imidazolidin-2-ylideneamino)-2-methyl-phenyl]-methanesulfonamide ($R^{34}$=$CH_3$, $R^{35}$=H, $R^{36}$=Br), mp 261.8–262.3° C., was prepared in a similar manner to that described above in Example 6, except the starting material was 5-bromo-2-methyl-3-nitro-phenylamine from above.

Example 6F

Preparation of N-[3-(imidazolidin-2-ylideneamino)-2,5-dimethyl-phenyl-methanesulfonamide

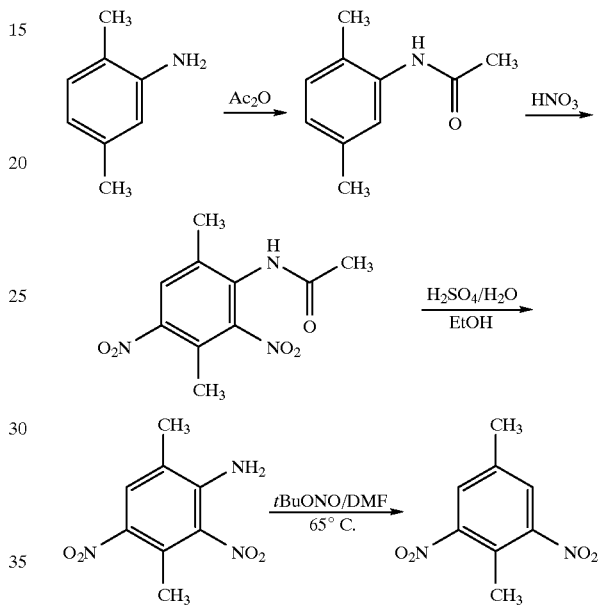

1. Preparation of N-(2,5-dimethyl-phenyl)-acetamide

Acetic anhydride (9.2 g) was added cautiously to 2,5-dimethylaniline (10.0 g). The mixture became hot and crystallized on cooling to room temperature. The gray mass was recrystallized to afford 12.6 g of the desired product.

2. Preparation of N-(3,6-dimethyl-2.4-dinitro-phenyl)-acetamide

Fuming nitric acid (90 mL) was cooled in an ice bath, and N-(2,5-dimethyl-phenyl)-acetamide (11.2 g, from above) was added portionwise over 30 min. The mixture was allowed to stir in the cold for an additional 1 hr, then allowed to warm to room temperature during 30 min. The reaction mixture was carefully poured into 900 g ice. After the ice melted the mixture was filtered and the light yellow product was washed with water. After drying at 80° C. under vacuum, N-(3,6-dimethyl-2.4-dinitro-phenyl)-acetamide (15.5 g) was obtained.

3. Preparation of 3,6-dimethyl-2.4-dinitro-phenylamine

A mixture of N-(3,6-dimethyl-2.4-dinitro-phenyl)-acetamide (14.4 g, from above), concentrated sulfuric acid (15 mL), water (30 mL) and ethanol (150 mL) was heated at reflux for 24 hr. The precipitated product was filtered, washed with little ethanol and dried to afford 3,6-dimethyl-2.4-dinitro-phenylamine (10.3 g).

4. Preparation of 2,5-dimethyl-1,3-dinitro-benzene

To a solution of t-butyl nitrite (t-BuONO) (7.32 g) in dimethyl formamide (DMF) (50 mL, from Mallinckrodt) at 65° C. was added dropwise a solution of 3,6-dimethyl-2,4-dinitro-phenylamine (10 g, from above) in DMF (50 mL) during 5–10 min. The mixture was heated at 65° C. for 15 min and the solvent was removed under reduced pressure. The residue was partitioned between dichloromethane (300 mL) and half-saturated sodium chloride solution. The dichloromethane solution was washed with additional half-saturated sodium chloride solution (300 mL) and dried over magnesium sulfate. After evaporation of the solvent, the residue was taken up in dichloromethane (250 mL) and passed through a short column (silica gel). Eluting with dichloromethane gave 2,5-dimethyl-1,3-dinitro-benzene (7.75 g).

5. Preparation of 2,5-dimethyl-3-nitro-phenylamine 2,5-Dimethyl-3-nitro-phenylamine was prepared from 2,5-dimethyl-1,3-dinitro-benzene (7.32 g, from above) in a manner similar to that described above in Example 6D4.

6. Preparation of N-[3-(imidazolidin-2-ylideneamino)-2,5-dimethyl-phenyl-methanesulfonamide N-[3-(imidazolidin-2-ylideneamino)-2,5-dimethyl-phenyl]-methanesulfonamide ($R^{34}$ and $R^{35}$=$CH_3$, $R^{36}$=H), 232.2–233.4° C., was prepared in a similar manner to that described above in Example 6, except the starting material was 2,5-dimethyl-3-nitro-phenylamine from above.

Example 6G

Preparation of N-[5-(imidazolidin-2-ylideneamino)-2,3-dimethyl-phenyl]-methanesulfonamide N-(3,4-dimethyl-phenyl)acetamide, N-(3,4-dimethyl-2,6-dinitro-phenylacetamide, 3,4-dimethyl-2,6-dinitro-phenylamine and 1,2-dimethyl-3,5-dinitrobenzene were prepared in a manner similar to that described above in Example 6F.

1. Preparation of 2,3-dimethyl-5-nitro-phenylamine 1,2-Dimethyl-3,5-dinitrobenzene (2.5 g, prepared as described in the above scheme) was dissolved in glacial acetic acid (25 mL, from Mallinckrodt) under $N_2$ and heated to reflux. The heat source was removed and iron (2.13 g) was added all at once. After the initial vigorous reaction, the mixture was heated at reflux for 10 min and then cooled to room temperature. The reaction mixture was filtered through a celite pad and washed with ethyl acetate. The filtrate was evaporated under reduced pressure. The residue was dissolved in ethyl acetate and refiltered through a celite pad and then washed with saturated sodium bicarbonate solution and half-saturated sodium chloride solution. After drying over magnesium sulfate and evaporation of the solvent, 2,3-dimethyl-5-nitro-phenylamine (1.41 g) was obtained.

2. Preparation of N-[5-(imidazolidin-2-ylideneamino)-2,3-dimethyl-phenyl]-methanesulfonamide N-[5-(imidazolidin-2-ylideneamino)-2,3-dimethyl-phenyl]-methanesulfonamide ($R^{34}$=H. $R^{35}$ and $R^{36}$=$CH_3$), mp 253.6–255.2° C., was prepared in a similar manner to that described above in Example 6, except the starting material was 2,3-dimethyl-5-nitro-phenylamine from above.

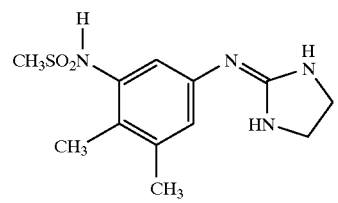

N-[5-(imidazolidin-2-ylideneamino)-2,3-dimethyl-phenyl]-methanesulfonamide

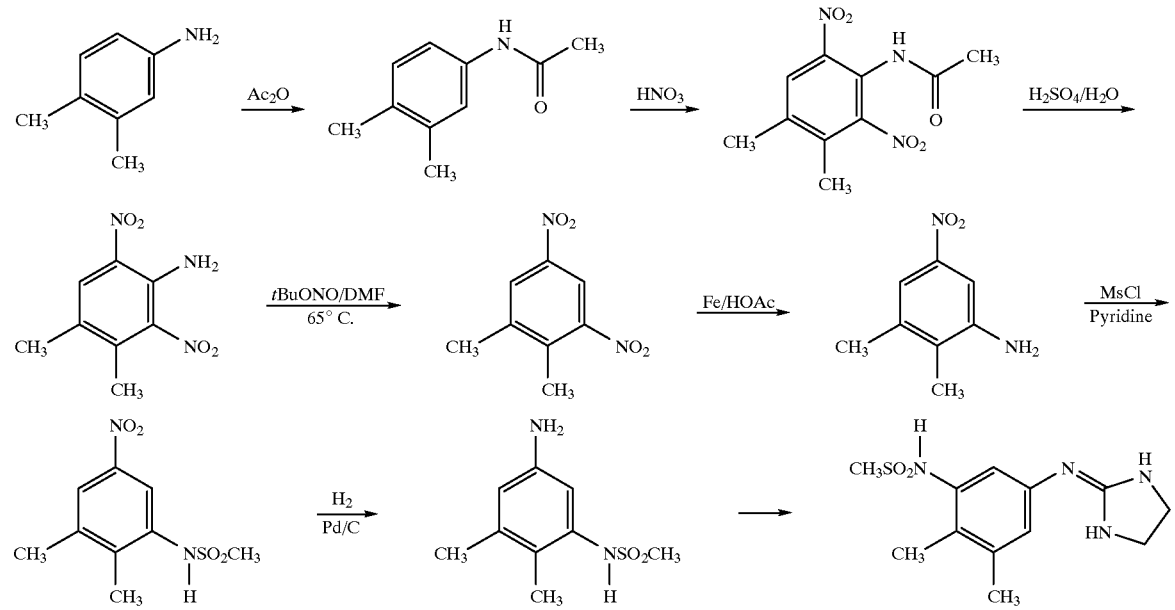

Example 6H

Preparation of N-[5-(imidazolidin-2-ylideneamino)-3-methyl-phenyl]methanesulfonamide 1. Preparation of 3,5-diaminotoluene

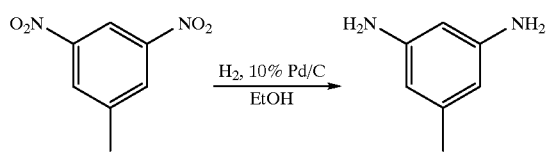

A mixture of 3,5-dinitrotoluene (2.85 g, 15.6 mmol) (prepared from p-toluidine according to procedures described in Example 6F) and 10% Pd/C (1.65 g, 1.56 mmol) in 50 mL of absolute ethanol was hydrogenated under a balloon of hydrogen gas for 20 hr. The mixture was filtered (Whatman GF/F) and the ethanol was removed at reduced pressure to give an amber oil which was used immediately in the next step.

2. Preparation of 1-N-methanesulfonamido-3-amino-5-methylbenzene

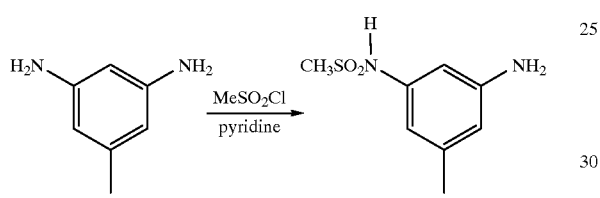

The 3,5-diaminotoluene (about 1.71 g, 1.53 mmol) was dissolved in pyridine (35 mL) and the resultant solution was cooled to 0° C. Mesyl chloride (1.53 g, 1.32 mmol, Aldrich) was added dropwise and the reaction was allowed to warm to room temperature. After stirring 14 hr, the solvent was removed at reduced pressure. The mixture was diluted with brine and extracted with ethyl acetate. The extracts were dried (MgSO$_4$) and concentrated to give 2.7 g of an orange-red solid. The crude product was preadsorbed onto SiO$_2$ with methanol and chromatographed (200 g SiO$_2$, 45% ethyl acetate/hexane) to give 0.41 g of product (Me=CH$_3$).

3. Preparation of N-[5-(imidazolidin-2-ylideneamino)-3-methyl-phenyl]-methanesulfonamide N-[5-(imidazolidin-2-ylideneamino)-3-methyl-phenyl]-methanesulfonamide ($R^{34}$=H, $R^{35}$=H, $R^{35}$=CH$_3$), mp 54–77° C., was prepared in a similar manner to that described above in Example 6, except the starting material was 1-N-methanesulfonamido-3-amino-5-methylbenzene.

Example 6I

Preparation of N-[5-imidazolidin-2-ylideneamino)-3-chloro-phenyl]methanesulfonamide N-[5-imidazolidin-2-ylideneamino)-3-chloro-phenyl]methanesulfonamide, mp 232.9–233.7° C. was prepared in a similar manner to that described above in Example 6H, except the starting material was 5-chloro-1,3-phenylenediamine.

Example 6J

Preparation of N-[5-imidazolidin-2-ylideneamino)-3-methoxy-phenyl]methanesulfonamide N-[5-imidazolidin-2-ylideneamino)-3-methoxy-phenyl]methanesulfonamide, mp 219.3–219.7° C., was prepared in a similar manner to that described above in Example 6H, except the starting material was 3,5-dinitro-anisole.

Example 6K

Preparation of N-[3-imidazolidin-2-ylideneamino)-5-isopropyl-2-methyl-phenyl]methanesulfonamide N-[3-imidazolidin-2-ylideneamino)-5-isopropyl-2-methyl-phenyl]methanesulfonamide, mp 231.8–232.3° C., was prepared in a similar manner to that described above in Example 6H, except the starting material was 5-isopropyl-2-methyl-1,3-dinitro-benzene.

Example 7

Preparation of N-[3-(1H-imidazol-4-ylmethoxy)-phenyl]methanesulfonamide

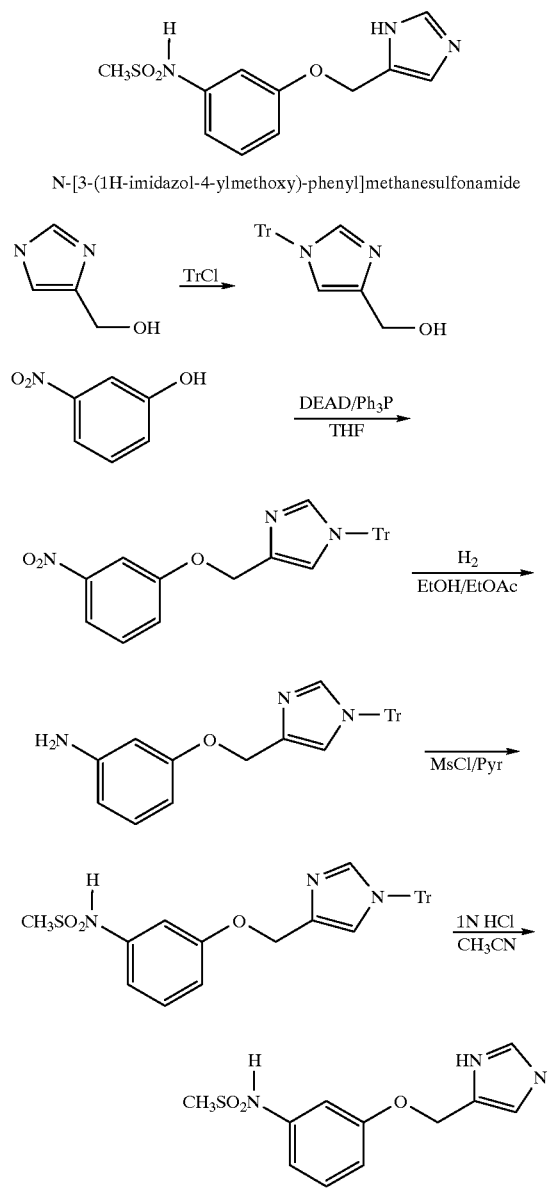

1. Preparation of 4-(3-nitro-phenoxymethyl)-1-trityl-1H-imidazole

To a solution of diethyl azodicarboxylate (2.1 mL) in tetrahydrofuran (THF) (40 mL) was added (1-trityl-1H-imidazole-4-yl)methanol (2.23 g, prepared as described in *J. Med. Chem.* (1977)20:721) and 3-nitrophenol (2 g). To this mixture at 0° C. was added dropwise a solution of triphenyl phosphine (3.44 g) in THF (60 mL). The reaction mixture was stirred at room temperature overnight. After evaporation of the solvent the residue was chromatographed on silica gel eluting with ethyl acetate:hexane (40:60) to isolate 4-(3-nitro-phenoxymethyl)-1-trityl-1H-imidazole (2 g).

2. Preparation of 3-(1-trityl-1H-imidazol-4-ylmethoxy) phenylamine

A mixture of 4-(3-nitro-phenoxymethyl)-1-trityl-1H-imidazole (1.5 g, from above) and 10% Pd/C (0.18 g) in ethyl acetate (60 mL) and ethanol(30 mL) was hydrogenated at 1 atmosphere overnight. The reaction mixture was filtered through a celite pad and the filtrate was evaporated under reduced pressure. The residue was purified by flash column chromatography on silica gel eluting with ethyl acetate:hexane (40:60) to afford 3-(1-trityl-1H-imidazol-4-ylmethoxy) phenylamine (0.6 g).

3. Preparation of N-[3-(1-trityl-1H-imidazol-4-ylmethoxy)-phenyl]methanesulfonamide A mixture of 3-(1-trityl-1H-imidazol-4-ylmethoxy) phenylamine (0.7 g, from above) and methanesulfonyl chloride (0.3 mL) in pyridine (12 mL) was stirred at room temperature overnight. Pyridine was removed under reduced pressure. The residue was dissolved in dichloromethane and washed with water and brine. After drying over sodium sulfate and evaporation of the solvent, N-[3-(1-trityl-1H-imidazol-4-ylmethoxy)-phenyl]methanesulfonamide (0.7 g) was obtained.

4. Preparation of N-[3-(1H-imidazol-4-ylmethoxy)-phenyl] methanesulfonamide

A mixture of N-[3-(1-trityl-1H-imidazol-4-ylmethoxy)-phenyl]methanesulfonamide (0.63 g, from above) and 1N HCl (10 mL) in acetonitrile (10 mL) was stirred at room temperature overnight. The solvent was removed and the residue was brought to basic pH with saturated potassium carbonate solution. The mixture was extracted with dichloromethane, washed with brine and dried over sodium sulfate. After evaporation of the solvent, the residue was chromatographed on silica gel eluting with methanol (containing 2% NH$_4$OH)/dichloromethane (7:93) to give N-(3-(1H-imidazol-4-ylmethoxy)-phenyl] methanesulfonamide. This was converted to N-[3-(1H-imidazol-4-ylmethoxy)-phenyl]methanesulfonamide oxalate salt, mp 178–180° C. by treating with 1M oxalic acid in ether.

Example 8

Preparation of N-[2-methyl-3-(oxazolidin-2-ylideneamino)-phenyl]-methanesulfonamide

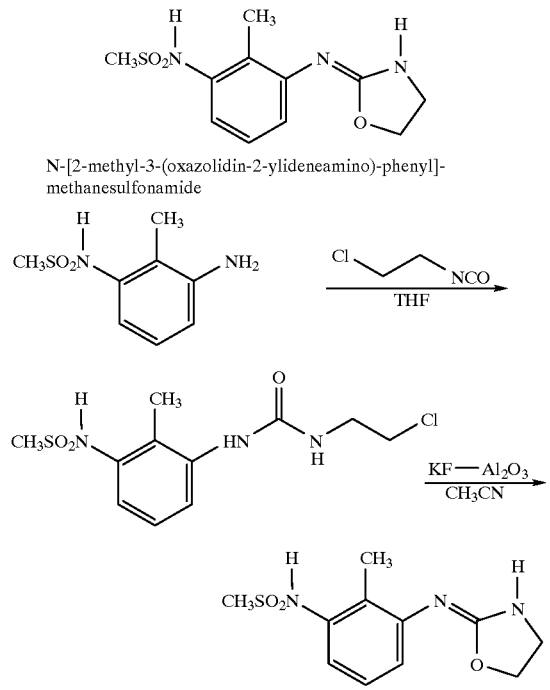

To a mixture of N-(3-amino-2-methyl-phenyl)-methanesulfonamide (1.5 g, from Example 6, part 1) in THF (30 mL) was added 2-chloroethylisocyanate (0.7 mL) dropwise at 0° C. The reaction mixture was slowly warmed to room temperature and stirred overnight. The precipitate was filtered, rinsed with THF, and dried to give N-{3-[3-(2-chloro-ethyl)-ureido]-2-methyl-phenyl}-methanesulfonamide (1.8 g). To the above compound (1.7 g) in acetonitrile (100 mL) was added potassium fluoride (40 wt. % on alumina) (3.5 g). The mixture was heated at 80° C. for 8 hr and filtered, washed with methanol. The filtrate was evaporated under reduced pressure. The residue was purified by flash chromatography on silica gel eluting with methanol:dichloromethane (5:95) to afford N-[2-methyl-3-(oxazolidin-2-ylideneamino)-phenyl]-methanesulfonamide. This was converted to oxalate salt (0.5 g), mp 124–140° C. in a manner similar to that described above in Example 7, part 4.

Example 9

Preparation of N,N-dimethyl-N'-[3-(4,5-dihydro-1H-imidazol-2-ylmethoxy)phenyl]sulfamide hydrochloride

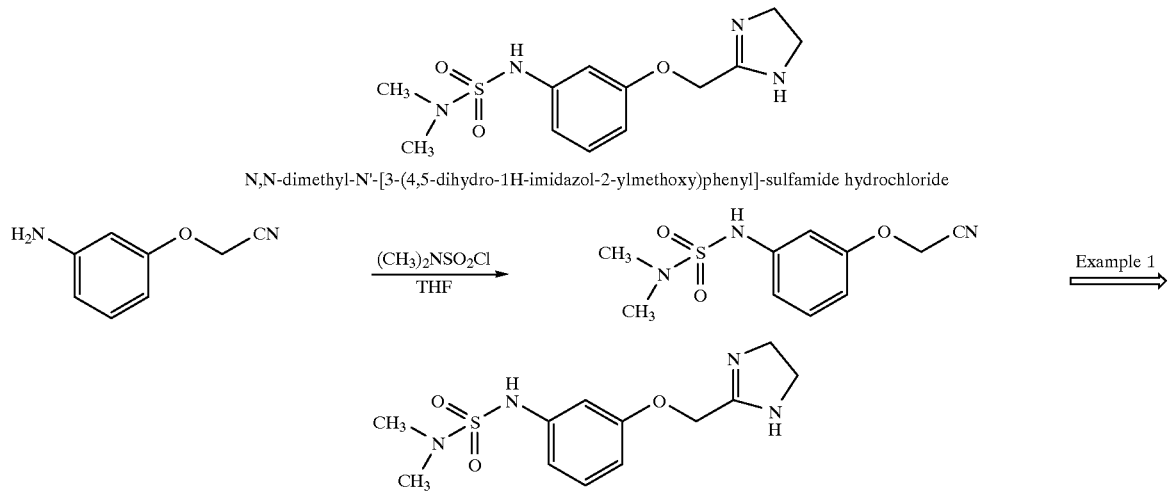

N,N-dimethyl-N'-[3-(4,5-dihydro-1H-imidazol-2-ylmethoxy)phenyl]-sulfamide hydrochloride 1. Preparation of N,N-dimethyl-N'-(3-cyanomethoxyphenyl)-sulfamide To a solution of (3-aminophenoxy)-acetonitrile (1.5 g, from Example 1), triethylamine (3.22 mL) in THF (35 mL) was added dimethylsulfamoyl chloride (4.2 mL) dropwise over 10 min. After stirring at room temperature for 1 hr, the solvent was evaporated and the residue was partitioned between dichloromethane and water. The organic layer was washed with 5% HCl solution and dried over magnesium sulfate. After evaporation of the solvent, the residue was purified by flash chromatography on silica gel eluting with ethyl acetate:dichloromethane (10:90) to give N,N-dimethyl-N'-(3-cyanomethoxyphenyl)-sulfamide (1.11 g).

2. Preparation of N,N-dimethyl-N'-[3-(4,5-dihydro-1H-imidazol-2-ylmethoxy)phenyl]-sulfamide hydrochloride N,N-dimethyl-N'-[3-(4,5-dihydro-1H-imidazol-2-ylmethoxy)phenyl]-sulfamide hydrochloride, mp 198.5–201° C., was prepared from N,N-dimethyl-N'-(3-cyanomethoxyphenyl)-sulfamide in a manner similar to that described above in Example 1.

Example 10

Preparation of N-methanesulfonyl-6-(4,5-dihydro-1H-imidazol-2-ylmethyl)indole hydrochloride

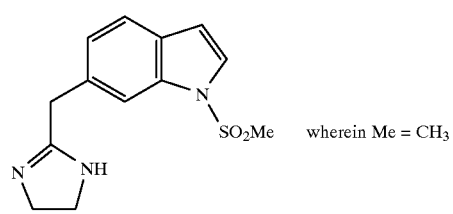

wherein Me = CH₃

1. Preparation of N-methanesulfonyl-6-carbomethoxyindole

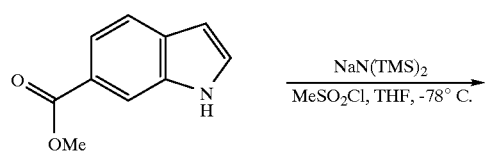

-continued

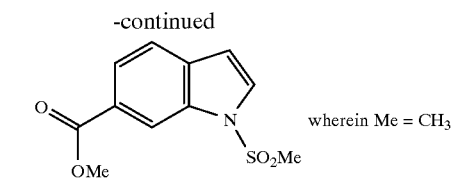

wherein Me = CH₃

A solution of NaN(TMS)₂ (1M) in THF (11 mmol, 11 ml) was added dropwise to a −78° C. solution of 6-carbomethoxyindole (876 mg, 5 mmol, prepared according to the procedure of Batcho, et al., *Org. Synth. Coll.* 7:34) in dry THF (10 ml). After stirring for 30 min, MeSO₂Cl (1.47 mL) (Me=CH₃) was added. The mixture was allowed to stir overnight then poured onto 100 ml of water. The mixture was extracted with CH₂Cl₂ (2×75 ml). The extracts were washed with brine, dried (Na₂SO₄), and the solvent was removed by rotary evaporation to give a light brown solid. The solid was purified by flash column chromatography (silica gel, 20% ethyl acetate/hexane) to give 510 mg of N-methanesulfonyl-6-carbomethoxyindole.

2. Preparation of N-methanesulfonyl-6-hydroxymethylindole

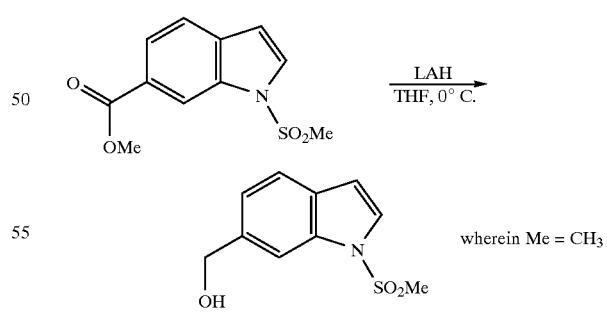

wherein Me = CH₃

A solution of lithium aluminum hydride (1M) in THF (2.57 mmol, 2.57 ml) was added dropwise to a 0° C. solution of N-methanesufonyl-6-carbomethoxyindole in dry THF (10 mL, from above). After 30 min, 0.5 ml of water was added dropwise followed by the addition of 0.5 ml 1.0M NaOH solution. Celite was added and the mixture was filtered through a coarse fritted funnel. The solids were washed with 20 ml ethyl acetate. The filtrate was concentrated under vacuum. The product was purified by flash column chromatography (silica gel, applied to column with toluene, gradient elution 20–50% ethyl acetate/hexane) to give 370 mg of N-methanesulfonyl-6-hydroxymethylindole, a white solid (80% yield).

3. Preparation of N-methanesulfonyl-6-bromomethylindole

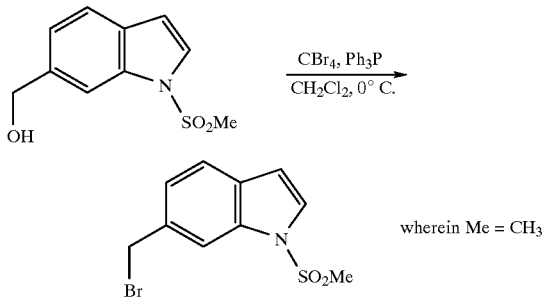

A solution of N-methanesulfonyl-6-hydroxymethylindole (340 mg, 1.51 mmol, from above) and triphenylphosphine (Ph₃P) (415 mg, 1.58 mmol) in 5 ml of dry CH$_2$Cl$_2$ was cooled to 0° C. and a solution of carbon tetrabromide (551 mg, 1.66 mmol) in 3 ml dry CH$_2$Cl$_2$ was added dropwise via cannula (2 ml CH$_2$Cl$_2$ rinse). The reaction mixture was allowed to warm to room temperature. After 4 hr, the solvent was removed by rotary evaporation and the resultant purple oil was purified by flash column chromatography (silica gel, 20% ethyl acetate/hexane) to give 290 mg of N-methanesulfonyl-6-bromomethylindole, a colorless oil which solidified on standing (67% yield).

4. Preparation of N-methanesulfonyl-6-cyanomethylindole

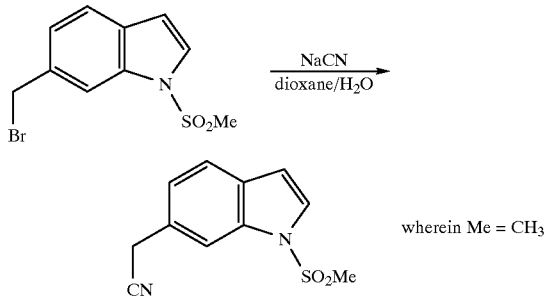

N-methanesulfonyl-6-bromomethylindole (280 mg, 0.97 mmol, from above) was dissolved in 1 ml of dioxane. Water (1 mL) was added followed by NaCN (52 mg, 1.07 mmol). The mixture was stirred for 9 days at room temperature. The reaction mixture was diluted with 30 ml of ethyl acetate and washed with 10 ml water. The aqueous layer was washed with 30 ml ethyl acetate. The combined extracts were washed with brine, dried (Na$_2$SO$_4$), and concentrated. The crude product was purified by flash column chromatography (silica gel, 40% ethyl acetate/hexane) to give 216 mg of the desired N-methanesulfonyl-6-cyanomethylindole (95% yield).

5. Preparation of 6-(N-methanesulfonylindolyl)acetimidic acid ethyl ester hydrochloride

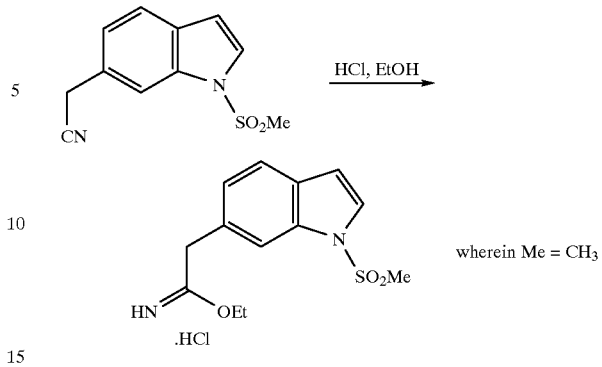

A 0° C. solution of the N-methanesulfonyl-6-cyanomethylindole (192 mg, 0.82 mmol, from above) in 5 ml of dry CH$_2$Cl$_2$ containing 0.24 ml anhydrous ethanol was treated with a stream of HCl gas for 1 min. The reaction flask was capped and the mixture was allowed to warm to room temperature. After stirring 36 hr, all the volatile were removed to give a foamy white solid which was used without purification.

6. Preparation of N-methanesulfonyl-6-(4,5-dihydro-1H-imidazol-2-ylmethyl)indole hydrochloride

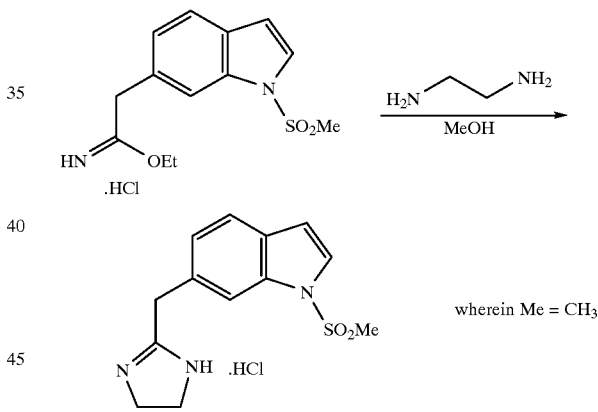

Ethylenediamine (82 μl, 1.23 mmol) was added to a solution of 6-(N-methanesulfonylindolyl)acetimidic acid ethyl ester hydrochloride (0.26 g, from above) in 5 ml of dry methanol. The mixture was stirred for 18 hr at room temperature. Silica gel (5 g) was added and the mixture was dried by rotary evaporation. The resultant powder was applied to a silica gel column and eluted with 85:10:5 mixture of ethyl acetate:methanol:isopropyl amine to give 161 mg of N-methanesulfonyl-6-(4,5-dihydro-1H-imidazol-2-ylmethyl)indole. The product was dissolved in 1.5 ml of methanol and treated with 1.5 ml of HCl in diethyl ether (1.0M). The solvents were removed by rotary evaporation. The product was cooled to −4° C. and the resultant crystals were washed with acetone to give 210 mg of N-methanesulfonyl-6-(4,5-dihydro-1H-imidazol-2-ylmethyl)indole after drying.

Example 11

Preparation of N-methanesulfonyl-6-(imidazolidin-2-ylideneamino)indole hydrochloride

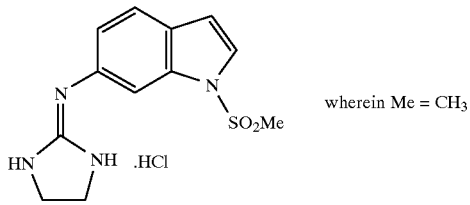

1. Preparation of N-methanesulfonyl-6-nitroindole

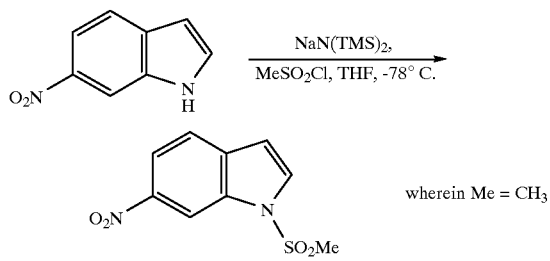

A solution of NaN(TMS)$_2$ in THF (12 ml, 12 mmol) was added to a −78° C. solution of 6-nitroindole (1.62 g, 10.0 mmol) in dry THF. After 20 min. MeSO$_2$Cl (1.37 g 12.0 mmol) was added. The reaction mixture was warmed to room temperature and after 1 hr filtered. The solids were boiled with aqueous methanol (30 ml) then filtered again. 2.07 g of product was obtained after drying under vacuum to constant weight (86% yield).

2. Preparation of N-methanesulfonyl-6-aminoindole

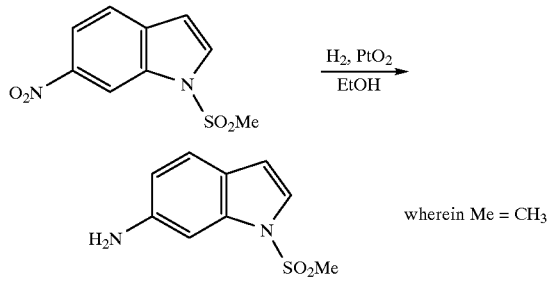

A mixture of N-methanesulfonyl-6-nitroindole (2.52 g, 10.5 mmol, from above) and platinum oxide (119 mg, 0.52 mmol) in 100 ml of methanol was hydrogenated in a Parr apparatus for approximately 1 hr until a constant pressure was obtained (42 psi H$_2$ initially). The catalyst was removed by filtration (Whatman GF/F filter) and the filtrate was concentrated by rotary evaporation to give N-methanesulfonyl-6-aminoindole, an oil which solidified on standing under an argon atmosphere.

Denny W.A. et al, Journal of Medicinal Chemistry, vol. 25, No. 3, Mar. 1982, pp. 276–315, Potential Antitumor Agents. 26. Quantitative Relationships between Experimental Antitumor Activity, Toxicity, and Structure for the General Class of 9–Anilinoacridine Antitumor Agents.

3. Preparation of N-methanesulfonyl-6-(imidazolidin-2-ylideneamino)indole hydrochloride

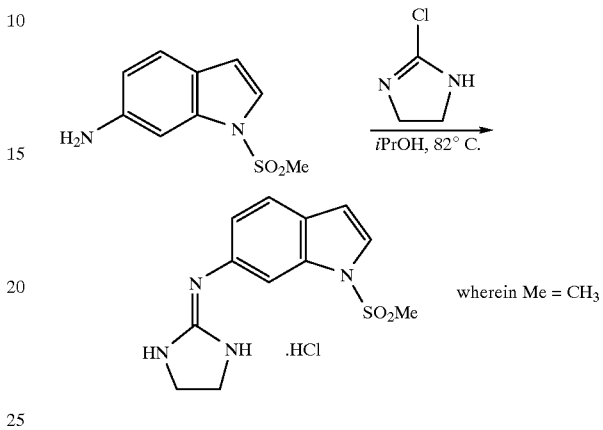

3.82 g of 2-chloroimidazoline hydrogen sulfate (see Example 6A) was treated with 50 ml of 1M NaOH solution and immediately extracted with CH$_2$Cl$_2$ (3×20 ml). The extracts were dried (K$_2$CO$_3$) and the solution decanted. 10 ml of isopropanol was added and the CH$_2$Cl$_2$ was removed at reduced pressure. The resultant isopropanol solution was added to a refluxing solution of the N-methanesulfonyl-6-aminoindole (2.02 g, 9.61 mmol) in isopropanol (10 mmol). The mixture was refluxed for 3 hr, cooled, and concentrated under vacuum. A portion (800 mg) of the crude product was dissolved in MeOH:H$_2$O (5:1) then 10 g of silica gel was added. The mixture was dried under vacuum and the resulting powder was applied to a silica gel column and eluted with ethyl acetate:MeOH:iPrNH$_2$ (93:5:2) (iPr=isopropyl). The white solid obtained was suspended in MeOH (4 ml) and treated with 3 ml of 1.0M HCl/ether. The solid dissolved then a precipitate formed which was filtered off after chilling the mixture in an ice bath. 590 mg of N-methanesulfonyl-6-(imidazolidin-2-ylideneamino)indole hydrochloride were obtained (mp 167.6–170.6° C.).

Example 11A

Preparation of 6-(Imidazolidin-2-ylideneamino) indole-1-sulfonic acid dimethylamide hydrochloride

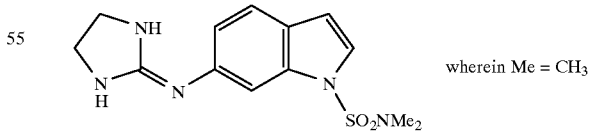

6-(Imidazolidin-2-ylideneamino)indole-1-sulfonic acid dimethylamide hydrochloride (mp 192.4–193.0° C.) was prepared from 6-nitroindole (Lancaster) in a manner similar to that described above in Example 11, except starting with N,N-dimethylsulfamoyl chloride in place of methanesolfonyl chloride.

Example 11B

Preparation of imidazolidin-2-ylidene-[1-(propane-1-sulfonyl)-1H-indol-6-yl]-amine

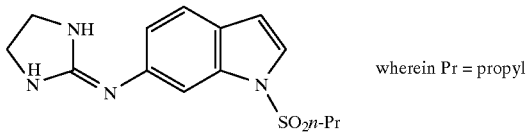

wherein Pr = propyl

Imidazolidin-2-ylidene-[1-(propane-1-sulfonyl)-1H-indol-6-yl]-amine (mp 212.6–213.1° C.) was prepared from 6-nitroindole (Lancaster) in a manner similar to that described above in Example 11, except starting with propylsulfonyl chloride in place of methanesolfonyl chloride.

Example 11C

Preparation of 6-(4,5-dihydro-1H-imidazol-2-ylmethoxy)-1-methanesulfonyl-1H-indole hydrochloride

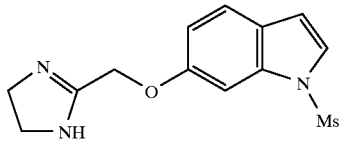

1. Preparation of 1-Methansulfonyl-1H-indol-6-ol

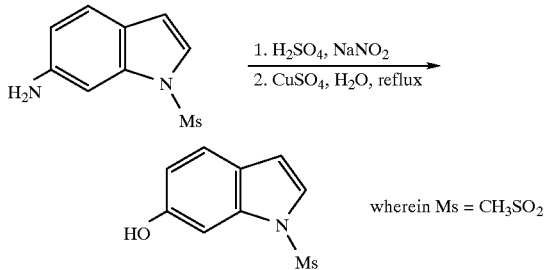

wherein Ms = CH$_3$SO$_2$

N-methansulfonyl-6-amino indole (2.10 g, 10.0 mmol), prepared as described in Forbes, et al., *J. Med. Chem.* (1996) 39:4968, was suspended in 40 ml of water, then cooled in an ice bath. Concentrated sulfuric acid (3 ml) was added slowly dropwise. The mixture was warmed to room temperature for 5 min then cooled back down to 0° C. A solution of NaNO$_2$ (Mallinckrodt, 0.76 g, 11.0 mmol) in 10 ml of water was added slowly and the resultant foam was treated with 10 ml of ethanol. The mixture was added in portions to a boiling solution of CUSO$_4$ (J. T. Baker, 16.0 g, 0.1 mol) in 75 ml of water. After 15 min, the mixture was cooled. The brown solid which had formed was broken up with a glass stirring rod. NaHCO$_3$ was added to neutralize the reaction and the product was extracted with ethyl acetate (2×100 ml). The extracts were dried (anhydrous MgSO$_4$) and concentrated to give 1-methansulfonyl-1H-indol-6-ol (1.62 g), a brown oil which was used with out purification.

2. Preparation of (1-Methansulfonyl-1H-indol-6-yloxy)acetonitrile

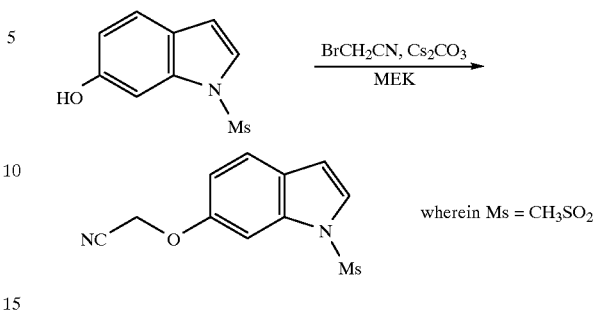

wherein Ms = CH$_3$SO$_2$

The 1-methansulfonyl-1H-indol-6-ol (1.62 g, 7.7 mmol) was dissolved in 10 ml methylethyl ketone. Cs$_2$CO$_3$ (Aldrich, 7.5 g, 23.0 mmol) was added followed by bromoacetonitrile (1.85, 15.4 mmol). The mixture was allowed to stir overnight. The mixture was diluted with water and the product was extracted with ethyl acetate. The extracts were washed with brine, then dried (anhydrous MgSO$_4$) and concentrated by rotory evaporation. (1-Methansulfonyl-1H-indol-6-yloxy)acetonitrile was purified by chromatography (SiO$_2$, elution with 30% ethyl acetate/hexane). 780 mg (37% yield from 1-methansulfonyl-1H-indol-6-ol) was obtained.

3. Preparation of 6-(4,5-dihydro-1H-imidazol-2-ylmethoxy)-1-methanesulfonyl-1H-indole hydrochloride

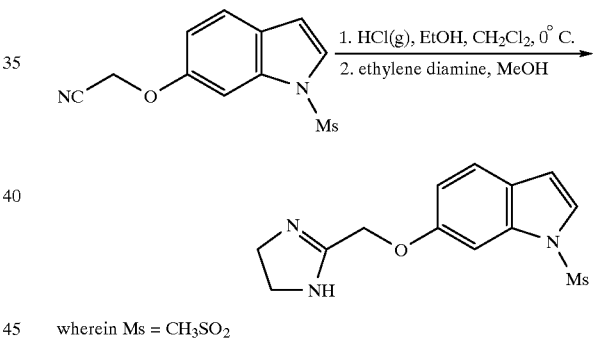

wherein Ms = CH$_3$SO$_2$

1-Methansulfonyl-1H-indol-6-ol acetronitrile (0.78 g, 3.12 mmol) was dissolved in 5 ml of dry CH$_2$Cl$_2$. Dry ethanol (2 ml) was added and the resultant solution was cooled to 0° C. A stream of HCl gas was passed over the solution for 1 min. The mixture was capped tightly and stored at room temperature for 24 hr. The volatiles were removed at reduced pressure to give a foamy solid which was dissolved in dry methanol (5 ml) and treated with ethylene diamine (0.38 g, 6.24 mmol) by dropwise addition. After 8 hr, the solvent was removed and the crude product was purified by chromatography (SiO2; eulution with 93% ethyl acetate/5% methanol/3% isopropyl amine) gave 520 mg of the free base. This was dissolved in acetone and 6 ml of 1M HCl in ether was added dropwise, producing a cystalline salt which was isolated by decanting the solvents. 540 mg of 6-(4,5-dihydro-1H-imidazol-2-ylmethoxy)-1-methanesulfonyl-1H-indole hydrochloride were obtained (52% yield, mp 135.4–136.3° C.).

Example 11D

Preparation of imidazolidin-2-ylidene-(1-methanesulfonyl-3-bromo-1H-indol-6-yl)-amine hydrochloride

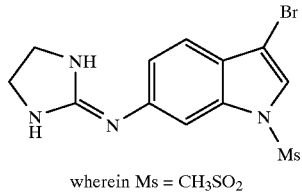

wherein Ms = CH₃SO₂

1. Preparation of 3-bromo-6-nitroindole

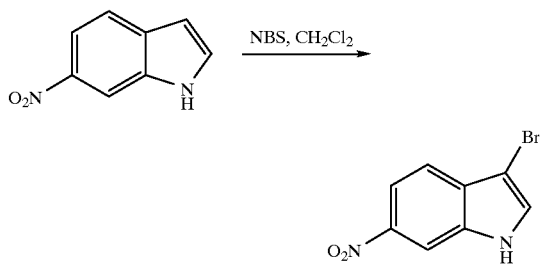

N-bromocuccinimide (2.31 g, 12.95 mmol) was added in portions over 5 min to a solution of 6-nitroindole (Lancaster, 2.0 g, 12.33 mmol) in 20 ml dry CH₂Cl₂. After 18 hr, the solvent was removed and the solids were chromatographed (200 g SiO₂, eluted with 2:1 hexane/ethyl acetate) to give 2.62 g of 3-bromo-6-nitroindole, a yellow solid (88% yield).

2. Preparation of 1-methanesulfonyl-3-bromo-6-nitro-1H-indole

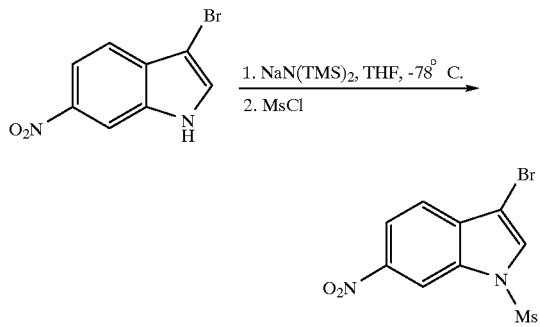

wherein Ms = CH₃SO₂

3-bromo-6-nitroindole (1.50 g, 6.22 mmol) was dissolved in 10 ml of dry THF. The solution was cooled to −78° C. The NaN(TMS)₂ (7.5 ml, 7.5 mmol, 1.0M in THF) was added dropwise creating a deep crimson solution. Methansulfonylchloride (0.71 g, 6.22 mmol) was added dropwise quenching the crimson color. The reaction was allowed to warm to room temperature. After 2 hr, the mixture was poured onto water and extracted with ethyl acetate. The extracts were dried (anhydrous MgSO₄) and concentrated. The resultant solid was boiled with 5 ml of acetone, then acetone was removed by pipet to give 1.55 g of product (78% yield).

3. Preparation of 1-methanesulfonyl-3-bromo-6-amino-1H-indole

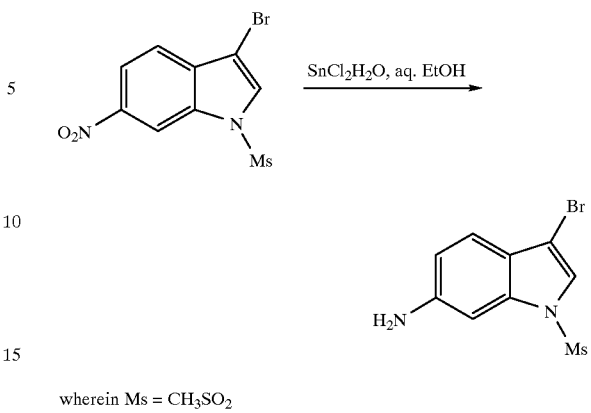

wherein Ms = CH₃SO₂

The 3-bromo-6-nitro-N-methanesulfonylindole (1.15 g, 3.67 mmol) was suspended in 40 ml of ethanol and 10 ml of water. The stannous chloride dihydrate (8.29 g, 36.7 mmol) was added and the mixture was stirred for 72 hr. Saturated NaHCO₃ solution was added until CO₂ evolution stopped. The mixture was filtered through celite and the solids were washed several times with methanol. The solvent was removed at reduced pressure and the resultant aqueous mixture was extracted with ethyl acetate. The extracts were washed with brine, then dried (anhydrous MgSO₄) and concentrated to give 680 mg of product which required no purification (64% yield).

4. Preparation of imidazolidin-2-ylidene-(1-methanesulfonyl-3-bromo-1H-indol-6-yl)-amine hydrochloride

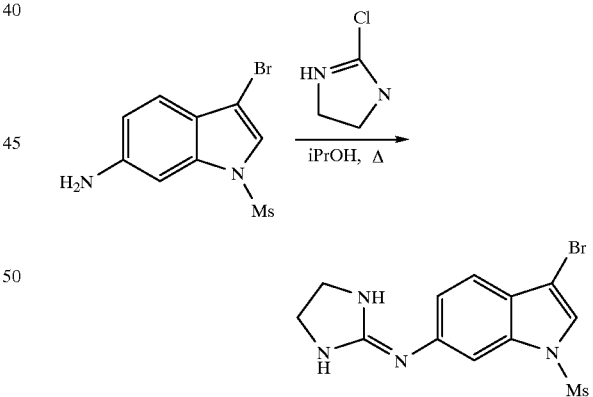

wherein Ms = CH₃SO₂

N-methanesulfonyl-6-(imidazolidin-2-ylideneamino)-3-bromoindole hydrochloride (mp 243–244.6° C.) was prepared from N-methanesulfonamide-3-bromo-6-amino indole by a procedure which was similar to that for the preparation of N-methanesulfonyl-6-(imidazolidin-2-ylideneamino)indole hydrochloride from N-methanesulfonyl-6-aminoindole.

Example 11E

Preparation of imidazolidin-2-ylidene-(1-methanesulfonyl-3-methyl-1H-indol-6-yl)-amine hydrochloride

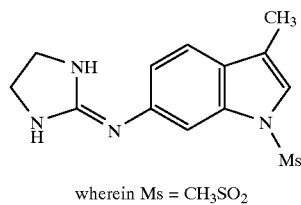

wherein Ms = CH₃SO₂

Preparation of N-(2-bromo-5-nitrophenyl) methanesulfonamide

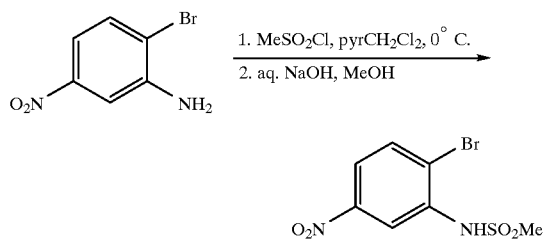

wherein Ms = CH₃SO₂

Methansulfonyl chloride (1.26 g, 18.43 mmol) was added to a 0° C. solution of 4-nitro-2-aminobromobenzene (1.6 g, 7.37 mmol) and triethlyamine (1.86 g, 18.43 mmol) in 20 ml of CH₂Cl₂. The reaction mixture was allowed to warm to room temperature and stirred 72 hr. The mixture was poured onto 50 ml of 1M HCl and extracted with 2×100 ml ethyl acetate. The extracts were washed with brine then dried (anhydrous MgSO₄) and concentrated. The material was dissolved in 10 ml of methanol and treated with 10 ml of 3M NaOH solution. The mixture was stirred overnight. The methanol was removed at reduced pressure, then 10 ml of water were added and the solution was washed with 50 ml of CH₂Cl₂. The aqueous was acidified to pH 1 by the dropwise addition of concentrated HCl. The product was extracted with ethyl acetate (2×75 ml). The extracts were dried (anhydrous MgSO₄) and concentrated to give 2.46 g of N-(2-bromo-5-nitrophenyl)methanesulfonamide.

2. Preparation of N-allyl-N-(2-bromo-5-nitrophenyl)-methanesulfonamide

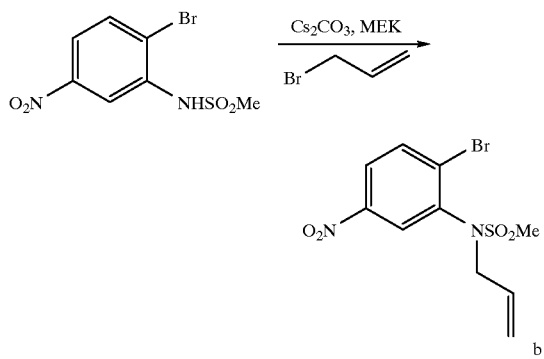

Allyl bromide (1.36 g, 11.25 mmol) was added to a mixture of N-(2-bromo-5-nitrophenyl)methanesulfonamide (1.66 g, 5.62 mmol) and cesium carbonate (5.49 g, 16.86 mmol) in methylethylketone (20 ml). The mixture was heated to reflux for 2 hr. The mixture was cooled and poured onto water. The product was extracted into ethyl acetate (2×75 ml) and the extracts were dried (anhydrous MgSO₄) and concentrated to provide 1.88 g of N-allyl-N-(2-bromo-5-nitrophenyl)methanesulfonamide which required no purification.

3. Preparation of 1-methanesulfonyl-3-methyl-6-nitro-1H-indole

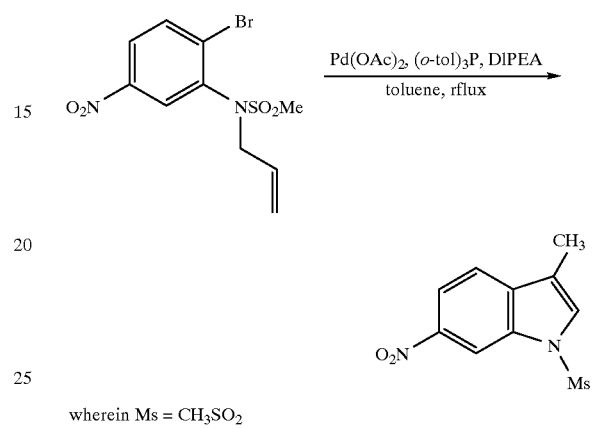

wherein Ms = CH₃SO₂

According to the method of Martin, *Helv. Chem. Acta.* (1989) 72:1554, a mixture of N-allyl-N-(2-bromo-5-nitrophenyl)methanesulfonamide (2.45 g, 7.31 mmol), palladium acetate (83 mg, 0.37 mmol), tri-o-tolyl phosphine (222 mg, 0.73 mmol) and diisopropylethylamine (1.42 g, 11.0 mmol) in 10 ml of toluene was heated to reflux for 18 hr. The reaction was cooled and filtered through a fine Whatman glass fiber filter to remove the palladium. The mixture was diluted with 100 ml of ethyl acetate, then washed successively with 1M HCl (50 ml) and brine. The extracts were dried (anhydrous MgSO₄) and concentrated. The crude product was dissolved in acetone. Silica gel (10 g) was added then the solvent was removed at reduced pressure. The resultant powder was applied to silica gel column (110 g) and eluted with 25% ethyl acetate/hexane to give 1.17 g of 1-methanesulfonyl-3-methyl-6-nitro-1H-indole (63% yield).

4. Preparation of 1-methanesulfonyl-3-methyl-6-amino-1H-indole

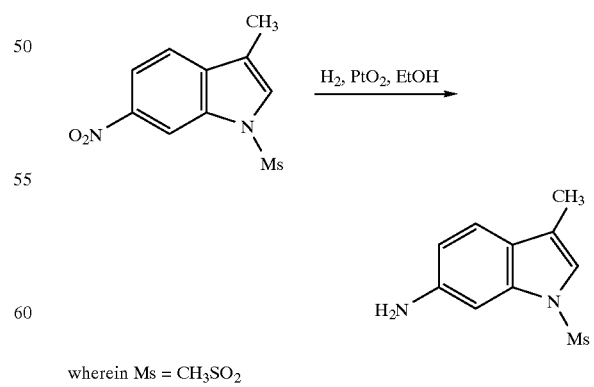

wherein Ms = CH₃SO₂

A mixture of 1-methanesulfonyl-3-methyl-6-nitro-1H-indole (1.17 g, 4.60 mmol) and platinum oxide (52 mg, 0.23 mmol) in 20 ml of absolute ethanol was stirred at room temperature under an atmosphere of hydrogen gas for 12 hr. The mixture was filtered through a fine Whatman glass fiber filter to remove the catalyst. A quantitative amount of 1-methanesulfonyl-3-methyl-6-amino-1H-indole was obtained after removing the ethanol at reduced pressure.

5. Preparation of Imidazolidin-2-ylidene-(1-methanesulfonyl-3-methyl-1H-indol-6-yl)-amine hydrochloride

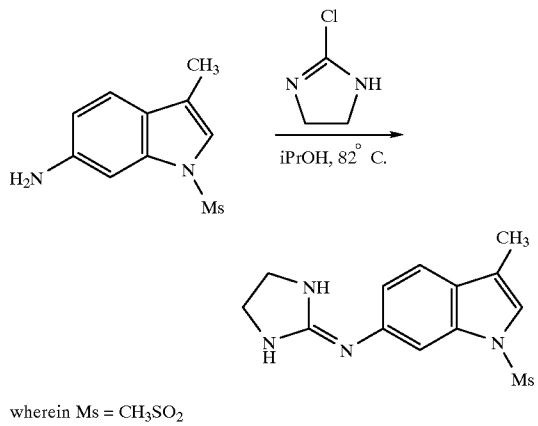

wherein Ms = CH$_3$SO$_2$

Imidazolidin-2-ylidene-(1-methanesulfonyl-3-methyl-1H-indol-6-yl)-amine hydrochloride (mp 236.4–236.7° C.) was prepared from 1-methanesulfonyl-3-methyl-6-amino-1H-indole by a procedure which was similar to that for the preparation of N-methanesulfonyl-6-(imidazolidin-2-ylideneamino)indole hydrochloride.

Example 11F

Imidazolindin-2-ylidene-(1-methanesulfonyl-3-chloro-1H-indol-6-yl)-amine hydrochloride Imidazolindin-2-ylidene-(1-methanesulfonyl-3-chloro-1H-indol-6-yl)-amine hydrochloride (mp 232.5–234.0° C.) was prepared in a manner similar to that described above in Example 11D for imidazolidin-2-ylidene-(1-methanesulfonyl-3-bromo-1H-indole-6-yl) amine hydrochloride, except starting with N-chloro succinimide in place of N-bromo succinimide.

Example 11G

Imidazolindin-2-ylidene-(1-methanesulfonyl-3-cyano-1H-indol-6-yl)-amine hydrochloride Imidazolindin-2-ylidene-(1-methanesulfonyl-3-cyano-1H-indol-6-yl)-amine hydrochloride (mp 199–199.5° C.) was prepared in a manner similar to that described above in Example 11D for imidazolidin-2-ylidene-(1-methanesulfonyl-3-bromo-1H-indole–6-yl) amine hydrochloride, except starting with chlorosulfonyl isocyanate in place of N-bromo succinimide according to the process described by Mehta, et al., *Synthesis* (1978) 374.

Example 12

Composition for Oral Administration

| The composition contains: | % wt./wt. |
|---|---|
| Active ingredient | 20.0% |
| Lactose | 79.5% |
| Magnesium stearate | 0.5% |

The two ingredients are mixed and dispensed into capsules containing 100 mg each; one capsule would approximate a total daily dosage.

Example 13

Composition for Oral Administration

| The composition contains: | % wt./wt. |
|---|---|
| Active ingredient | 20.0% |
| Magnesium stearate | 0.5% |
| Crosscarmellose sodium | 2.0% |
| Lactose | 76.5% |
| PP (polyvinylpyrrolidine) | 1.0% |

The above ingredients are combined and granulated using methanol as solvent. The formulation is then dried and formed into tablets (containing 20 mg of active compound) with an appropriate tableting machine.

Example 14

Parenteral Formulation (IV)

| The composition contains: | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 15

Suppository Formulation

| The composition contains: | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 16

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

Example 17

Nasal Spray Formulations

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–12 hr.

Example 18

Assays for Alpha$_{1A/1L}$-Adrenoceptor Activity

Compounds used in this Example 18 were from Sigma Chemical Co., St. Louis, Mo., U.S.A.) unless specified otherwise.

A. In Vitro Assay

Male white New Zealand rabbits (3–3.5 kg) and Sprague-Dawley rats (250–400 g) were euthanized by $CO_2$ asphyxiation. The bladder (rabbit) or aorta (rat) were removed, extraneous tissue was dissected away, and tissues were placed in oxygenated Krebs' solution (mM: NaCl, 118.5; $NaHCO_3$, 25; dextrose, 5: KCl, 4.8; $CaCl_2$, 2.5; $MgSO_4$, 1.2 and $KH_2PO_4$, 1.2). Cocaine (30 $\mu$M), corticosterone (30 $\mu$M), ascorbic acid (100 $\mu$M), indomethacin (10 $\mu$M), and propranolol (1 $\mu$M) were added to the Krebs' solution to block neuronal uptake, extraneuronal uptake, auto-oxidation of catecholamines, prostanoid synthesis, and beta-adrenoceptors, respectively. The alpha$_2$-adrenoceptor antagonist idazoxan (0.3 $\mu$M, Research Biochemicals, Inc., Natick, Mass., U.S.A.) and the calcium channel antagonist nitrendipine (1 $\mu$M, Research Biochemico International, Natick, Mass., U.S.A.) were added the Krebs' solution for rabbit and rat experiments, respectively. Strips of bladder neck (rabbit) approximately 0.8–1.2 cm in length and 2–3 mm in width and aortic rings (2–4 per rat) approximately 3 mm in width, cut as near the heart as possible, were suspended in water-jacketed tissue baths at a resting tension of 1. Tissues were maintained at 34° C. and bubbled continuously with an oxygen/carbon dioxide mixture.

Tissues were primed with norepinephrine (10 $\mu$M) and washed for 60 minutes before constructing a first cumulative concentration-effect to norepinephrine. Tissues were then washed for 60 minutes before constructing a second concentration-effect curve to a test agonist. The concentration producing the half maximal response (pEC$_{50}$) and the intrinsic activity (relative to norepinephrine) were recorded. Results for standards and representative compounds of the present invention were determined. Representative compounds of the invention showed activity in this assay.

B. In Vivo Assay: Anesthetized Pig Urethra/Blood Pressure Model:

Female Yucatan micropigs (12–35 kg; $\geq$10 months old) were anesthetized with ketamine (Aveco Co., Ft. Dodge, Iowa, U.S.A.) followed by pentobarbital (Schering Plough Animal Health Corp., Kenilworth, N.J., U.S.A.). A cuffed endotracheal tube was placed in the trachea and the pig mechanically ventilated with room air under positive pressure. The right or left femoral artery and vein were isolated and cannulated. One of the two cannulae inserted into the femoral vein was used to infuse pentobarbital (5–20 mg/kg/hr) via an infusion pump. The second cannula was used to administer test compounds. The cannula inserted into the femoral artery was connected to a blood pressure transducer (Gould/Statham Sprectamed P23 series) for the measurement of aortic blood pressure. Needle electrodes were placed subcutaneously to record a limb lead II ECG and heart rate was monitored by a tachometer triggered by the R-wave of the ECG. Body heat was maintained with an Aquamatic hot water blanket, model K-20, and rectal temperature was continuously monitored with a YSI TeleThermometer, model 43TA.

Following a ventral midline laparotomy, both ureters were cannulated for the exteriorization of urine. The bladder was emptied and a water-filled balloon catheter (reservoir tip of a latex condom attached to PE-190 tubing) attached to an external pressure transducer was inserted through the bladder via a stab incision. The balloon catheter was advanced into the urethra and secured with silk ligatures. Correct placement of the balloon was verified by palpating the urethra when inflating and deflating the balloon.

Following the surgical preparation, blood gases (analyzed by a Nova Stat Profile 3 blood gas analyzer) and pH were adjusted to within normal limits by adjusting respiratory rate, tidal volume, and/or positive-end expiratory pressure. Intraurethral pressure was adjusted to an appropriate baseline (20–40 cmH$_2$O) by inflating or deflating the balloon. Following a 30 minute stabilization period, the pig was pretreated with a beta-adrenoceptor antagonist (propranolol; 100 $\mu$g/kg, iv), a non-selective alpha$_2$-adrenoceptor antagonist [8aR-(8aa,12aa,13aa)]-N-[3-[(5,8a,9,10,11,12a,13,13a-octahydro-3-methoxy-6H-isoquinol[2,1-g][1,3]naphthyridin-12(8H)-yl)-sulfonyl]propyl]-methanesulfonamide (for example, prepared by procedures described by Clark et al., European Patent Application No. 524004 A1, for compounds according to the present invention, 300 $\mu$g/kg, iv), and a ganglionic antagonist (chlorisondamine; 200 $\mu$g/kg, iv, prepared according to the procedure described in U.S. Pat. No. 3,025,294). A single phenylephrine challenge (10 $\mu$g/kg, iv) was given to verify intraurethral and blood pressure responses. After the response returned to baseline, multiple escalating doses of agonists were administered intravenously and maximal intraurethral and diastolic blood pressure responses following each dose were recorded. Intervals between doses varied from 5–120 minutes to allow responses to return to baseline before giving the next dose. At the end of each experiment, pigs were euthanized by a lethal injection of pentobarbital. The maximum responses for intraurethral and diastolic blood pressure for standards and representative compounds of the invention were determined.

Representative compounds of the invention showed activity in this assay.

C. In Vivo Assay: Conscious Pig Urethra/Blood Pressure Model:

Female Yucatan micropigs (12–35 kg; ≧10 months old) were trained to rest quietly in a sling for a week prior to surgery. Only those pigs which acclimated to the sling were used for the study. Pigs were surgically instrumented under aseptic conditions. A telemetry device (Data Science International, St. Paul, Minn., U.S.A., model TA11PAD-70) was implanted into the pig with the cannula potion of the device inserted into the right external iliac artery and advanced into the abdominal aorta. The transmitter portion of the device was placed in a pocket created under the skin in close proximity to the insertion point of the cannula. A vascular access port (Sims Deltec, St. Paul, Minn., U.S.A.) with a silicon catheter was implanted for intravenous administration of test compounds. The catheter portion was inserted into the left or right jugular vein with the port under the skin in the shoulder area. A strain-gauge transducer (SF Products, Madison, Wis., U.S.A.) was sutured to the urethra and the wire exteriorized dorsally. Pigs were allowed at least one week to recover from surgery.

One each experimental day, pigs were placed in the sling and allowed to stabilize before administering a phenylephrine prime (10 μg/kg, iv) to verify the placement of the needle in the vascular access port and calibration of the telemetry and strain-gauge probes. After urethral tension and blood pressure returned to baseline values, a non-cumulative dose-response curve to phenylephrine was constructed. Intervals between doses varied form 5–120 minutes to allow blood pressure to return to baseline levels. Sixty minutes after the last phenylephrine dose returned to baseline, a second non-cumulative curve to test compound was constructed. Responses to test compounds were expressed as a percentage of the maximum response obtained with phenylephrine.

Representative compounds of the invention showed activity in this assay.

Example 19

Assays For Nasal Decongestion

1. In Vitro Dog Isolated Nasal Mucosa Assay

The upper jaw is removed postmortem and placed in standard Krebs' solution. The nasal mucosa tissue is then removed from the surrounding tissue and cut into strips. Each strip is suspended in a 10 ml tissue bath under a resting tension of 1 g in Krebs' solutions of the following composition (mM): NaCl 118.5; NaHCO$_3$ 25; dextrose 5; KCl 4.8; CaCl$_2$ 1.25; MgSO$_4$ 1.2 and KH$_2$PO$_4$ 1.2. The Krebs' solution also contains cocaine (30 μM); corticosterone (30 μM); propranolol (1 μM); indomethacin (10 μM) and ascorbic acid (100 μM) to block neuronal and extraneuronal uptake, β-adrenoceptor, prostanoid synthesis, and autooxidation of catecholamines, respectively. The baths are maintained at 37° C. and continuously aerated with 95% O$_2$/5% CO$_2$. The tissue strips are allowed to equilibrate for 1 hr, readjusting tension to maintain a testing tension of ig and washing tissues every 10 min with Krebs' solution. The strips are then exposed to a priming concentration of norepinephrine (1 μM) by direct administration into the bath. Tissues are washed every 5 min for half an hour or until a baseline tension of 1 g is maintained in every tissue.

Five min after the last wash, a cummulative concentration-effect curve is constructed by direct administration of norepinephrine into the baths. After obtaining a maximum response, tissues are washed every 5 min for the first 30 min and every 15 min for the next hour. A second cumulative concentration-effect curve is then constructed with either norepinephrine (in the absence or presence of antagonist) or test agonist.

2. In Vivo Dog Nasal Cavity Pressure Model

Male or female beagle dogs (8–12 kg) are fasted for 12–18 hr and then are anesthetized with sodium pentobarbital (33 mg/kg, iv). A cuffed endotracheal tube is placed in the trachea and the animal is ventilated with room air. The right femoral artery and vein are isolated and two polyethylene cannulae are inserted into the femoral vein. One of the cannulae is used to infuse sodium pentobarbital (5 mg/kg/hr) via infusion pump to maintain anesthesia. The second cannula, whose tip is advanced beyond that of the anesthetic cannula, is used to administer compounds. A fluid-filled cannula is inserted into the femoral artery and advanced into the abdominal aorta for measurement of aortic blood pressure and for the withdrawal of blood samples for blood gas analyses. The body temperature is monitored using a telethermometer rectal probe.

A water-filled balloon catheter (prepared by affixing the reservoir tip of a latex condom to the distal end of a cannula) attached to an external pressure transducer is inserted through the right nostril approximately 2.5 in deep into the nasal cavity.

Once the dog is stabilized, a single amidephrine challenge (1 μg/kg,iv) is given to verify nasal cavity pressure and blood pressure responses. Amidephrine (0.01–10 μg/kg, iv) is administered at 5–30 min intervals. After 50–60 min, when the nasal cavity pressure and blood pressure return to the baseline, a second curve to amidephrine (time control) or test agonist is administered at 5–30 minute intervals. Following the last dose, an alpha$_1$- and/or alpha$_2$-adrenoceptor antagonist is administered to determine the receptor mediating the nasal cavity pressure response. Blood pressure, heart rate, ECG and nasal cavity pressure are monitored throughout the experiment using a physiograph. At the end of the study the animal is killed by an intravenous overdose of sodium pentobarbital (5 ml, 389 mg/ml).

The non-selective alpha$_1$-adrenoceptor agonist, phenylephrine, and the alpha$_{1A}$-adrenoceptor selective agonist, amidephrine, are active in both of the above assays and are used as controls.

Representative compounds of the invention showed activity in these assays.

What is claimed is:

1. A compound represented by the Formula:

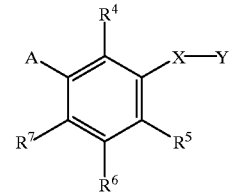

wherein:

A is $R^1_q(R^3R^{60}N)_m(Z)(NR^2)_n$;

m and q are each 0 or 1, with the proviso that when q is 1, m is 0 and when q is 0, m is 1;

Z is C=O or SO$_2$;

n is 1 with the proviso that, when Z is C=O, m is 1;

X is —NH—, —CH$_2$—, or —OCH$_2$—;

Y is 2-imidazoline or 4-imidazole;

$R^1$ is H, lower alkyl, or phenyl, with the proviso that, when $R^1$ is H, m is 1;

$R^2$, $R^3$, and $R^{60}$ are each independently H, lower alkyl, or phenyl;

$R^4$, $R^5$, $R^6$, and $R^7$ are each independently hydrogen, lower alkyl, —$CF_3$, lower alkoxy, halogen, phenyl, lower alkenyl, hydroxyl, lower alkylsulfonamido, or lower cycloalkyl, wherein $R^2$ and $R^7$ optionally may be taken together to form alkylene or alkenylene of 2 to 3 carbon atoms in an unsubstituted or optionally substituted 5- or 6-membered ring, wherein the optional substituents on the ring are halo, lower alkyl, or —CN, with the proviso that, when $R^7$ is hydroxyl or lower alkylsulfonamido, then X is not —NH— when Y is 2-imidazoline;

or a pharmaceutically acceptable salt thereof.

2. The compound of claim 1 wherein A is ($R^1SO_2NR^2$—), ($R^3R^{60}NSO_2NR^2$—), or ($R^3R^{60}NCONR^2$—); or a pharmaceutically acceptable salt thereof.

3. The compound of claim 1 wherein $R^1$ is methyl, ethyl, propyl, or phenyl; or a pharmaceutically acceptable salt thereof.

4. The compound of claim 3 wherein all but one of $R^4$, $R^5$, $R^6$, and $R^7$ are hydrogen and the remaining one is selected from the group consisting of methyl, ethyl, —$CF_3$, methoxy, chlorine, bromine, fluorine, isopropyl, cyclopropyl, ethenyl, hydroxy, and methylsulfonamido; or a pharmaceutically acceptable salt thereof.

5. The compound of claim 3 wherein all but two of $R^4$, $R^5$, $R^6$, and $R^7$ are hydrogen and the remaining two are each independently selected from the group consisting of methyl, ethyl, isopropyl, —$CF_3$, chlorine, bromine, and fluorine; or a pharmaceutically acceptable salt thereof.

6. The compound of claim 3 wherein $R^2$ and $R^7$ are taken together to form ethenylene in a 5-membered ring, or a pharmaceutically acceptable salt thereof.

7. The compound of claim 1 wherein X is —NH—, or a pharmaceutically acceptable salt thereof.

8. The compound of claim 1 wherein X is —$CH_2$—, or a pharmaceutically acceptable salt thereof.

9. The compound of claim 1 wherein X is —$OCH_2$—, or a pharmaceutically acceptable salt thereof.

10. The compound of claim 1 wherein Y is 2-imidazoline, or a pharmaceutically acceptable salt thereof.

11. The compound of claim 1 wherein Y is 4-imidazole, or a pharmaceutically acceptable salt thereof.

12. A compound represented by the Formula:

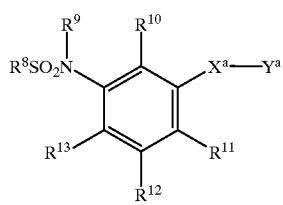

wherein:

$X^a$ is —NH—, —$CH_2$—, or —$OCH_2$—;

$Y^a$ is 2-imidazoline or 4-imidazole;

$R^8$ is lower alkyl, phenyl, or —$NR^{14}R^{15}$;

$R^9$, $R^{14}$, and $R^{15}$ are each independently H or lower alkyl;

$R^{10}$, $R^{11}$, $R^{12}$, and $R^{13}$ are each independently hydrogen, lower alkyl, —$CF_3$, lower alkoxy, halogon, phenyl, lower alkenyl, hydroxyl, lower alkylsulfonamido, or lower cycloalkyl, wherein $R^9$ and $R^{13}$ optionally may be taken together to form alkylene or alkenylene of 2 to 3 carbon atoms in a 5- or 6-membered ring, with the proviso that, when $R^{13}$ is hydroxyl or lower alkylsulfonamido, then $X^a$ is not —NH— when $Y^a$ is 2-imidazoline;

or a pharmaceutically acceptable salt thereof.

13. The compound of claim 12 wherein $R^8$ is methyl, ethyl, propyl, phenyl, amino, methylamino, or dimethylamino; or a pharmaceutically acceptable salt thereof.

14. The compound of claim 13 wherein all but one of $R^{10}$, $R^{11}$, $R^{12}$, and $R^{13}$ are hydrogen and the remaining one is selected from the group consisting of methyl, ethyl, —$CF_3$, methoxy, chlorine, bromine, fluorine, isopropyl, cyclopropyl, ethenyl, hydroxy, and methylsulfonamido; or a pharmaceutically acceptable salt thereof.

15. The compound of claim 13 wherein all but two of $R^{10}$, $R^{11}$, $R^{12}$, and $R^{13}$ are hydrogen and the remaining two are each independently selected from the group consisting of methyl, ethyl, isopropyl, —$CF_3$, chlorine, bromine, and fluorine; or a pharmaceutically acceptable salt thereof.

16. The compound of claim 13 wherein $R^9$ and $R^{13}$ are taken together to form ethenylene in a 5-membered ring, or a pharmaceutically acceptable salt thereof.

17. The compound of claim 12 wherein $X^a$ is —NH—, or a pharmaceutically acceptable salt thereof.

18. The compound of claim 12 wherein $X^a$ is —$CH_2$—, or a pharmaceutically acceptable salt thereof.

19. The compound of claim 12 wherein $X^a$ is —$OCH_2$—, or a pharmaceutically acceptable salt thereof.

20. The compound of claim 12 wherein $Y^a$ is 2-imidazoline, or a pharmaceutically acceptable salt thereof.

21. The compound of claim 12 wherein $Y^a$ is 4-imidazole, or a pharmaceutically acceptable salt thereof.

22. A compound represented by the Formula:

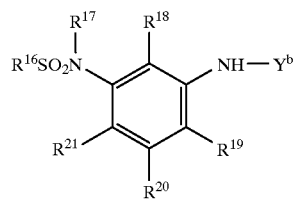

wherein:

$Y^b$ is 2-imidazoline;

$R^{16}$ is lower alkyl;

$R^{17}$ is H or lower alkyl;

$R^{18}$, $R^{19}$, $R^{20}$, and $R^{21}$ are each independently hydrogen, lower alkyl, —$CF_3$, lower alkoxy, or halogen;

or a pharmaceutically acceptable salt thereof.

23. The compound of claim 22 wherein $R^{16}$ is methyl, or a pharmaceutically acceptable salt thereof.

24. The compound of claim 22 wherein all but one of $R^{18}$, $R^{19}$, $R^{20}$, and $R^{21}$ are hydrogen and the remaining one is selected from the group consisting of methyl, ethyl, isopropyl, —$CF_3$, methoxy, fluorine, chlorine, and bromine; or a pharmaceutically acceptable salt thereof.

25. The compound of claim 22 wherein all but two of $R^{18}$, $R^{19}$, $R^{20}$, and $R^{21}$ are hydrogen and the remaining two are each independently selected from the group consisting of methyl, ethyl, isopropyl, —$CF_3$, methoxy, fluorine, chlorine, and bromine; or a pharmaceutically acceptable salt thereof.

26. The compound of claim 22 wherein $R^{16}$ is methyl and $R^{17}$ is H; or a pharmaceutically acceptable salt thereof.

27. A compound represented by the Formula:

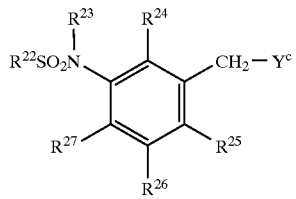

wherein:
$Y^c$ is 2-imidazoline or 4-imidazole;
$R^{22}$ is lower alkyl;
$R^{23}$ is H or lower alkyl;
$R^{24}$, $R^{25}$, $R^{26}$, and $R^{27}$ are each independently hydrogen, lower alkyl, lower alkoxy, halogen, phenyl, lower alkenyl, hydroxyl, or lower alkylsulfonamido;
or a pharmaceutically acceptable salt thereof.

28. The compound of claim 27 wherein $R^{22}$ is methyl, ethyl, or isopropyl; or a pharmaceutically acceptable salt thereof.

29. The compound of claim 27 wherein $R^{23}$ is hydrogen or methyl; or a pharmaceutically acceptable salt thereof.

30. The compound of claim 27 wherein all but one of $R^{24}$, $R^{25}$, $R^{26}$, and $R^{27}$ are hydrogen and the remaining one is selected from the group consisting of methyl, ethyl, isopropyl, ethenyl, —$CF_3$, methoxy, hydroxy, phenyl, fluorine, chlorine, bromine, and methylsulfonamido; or a pharmaceutically acceptable salt thereof.

31. The compound of claim 27 wherein all but two of $R^{24}$, $R^{25}$, $R^{26}$, and $R^{27}$ are hydrogen and the remaining two are each independently selected from the group consisting of methyl, ethyl, chlorine, and bromine; or a pharmaceutically acceptable salt thereof.

32. The compound of claim 27 wherein $Y^c$ is 2-imidazoline or 4-imidazole, $R^{22}$ is methyl, and $R^{23}$ is H; or a pharmaceutically acceptable salt thereof.

33. A compound represented by the Formula:

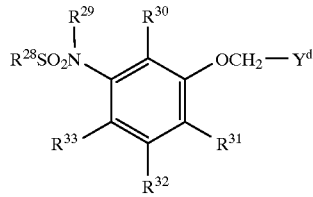

wherein:
$Y^d$ is 2-imidazoline or 4-imidazole;
$R^{28}$ is lower alkyl or phenyl;
$R^{29}$, $R^{30}$, $R^{31}$, $R^{32}$, and $R^{33}$ are each independently hydrogen, lower alkyl, halogen, hydroxyl, or lower cycloalkyl;
or a pharmaceutically acceptable salt thereof.

34. The compound of claim 33 wherein $R^{28}$ is methyl, ethyl, propyl, or phenyl; or a pharmaceutically acceptable salt thereof.

35. The compound of claim 33 wherein all but one of $R^{30}$, $R^{31}$, $R^{32}$, and $R^{33}$ are hydrogen and the remaining one is selected from the group consisting of cyclopropyl, chlorine, bromine, fluorine, hydroxy, methyl, and ethyl; or a pharmaceutically acceptable salt thereof.

36. The compound of claim 33 wherein all but two of $R^{24}$, $R^{25}$, $R^{26}$, and $R^{27}$ are hydrogen and the remaining two are each independently selected from the group consisting of methyl, ethyl, chlorine, and bromine; or a pharmaceutically acceptable salt thereof.

37. The compound of claim 33 wherein Yd is 2-imidazoline or 4-imidazole and $R^{28}$ is methyl; or a pharmaceutically acceptable salt thereof.

38. The compound of claim 37 wherein $Y^d$ is 2-imidazoline, $R^{30}$ is methyl, and $R^{33}$ is halogen; or a pharmaceutically acceptable salt thereof.

39. The compound of claim 38 wherein $R^{33}$ is chlorine or bromine.

40. A compound represented by the Formula:

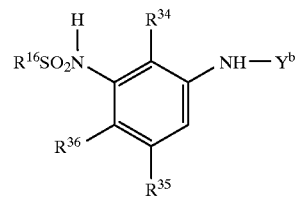

wherein:
$Y^b$ is 2-imidazoline;
$R^{16}$ is lower alkyl;
$R^{34}$, $R^{35}$, and $R^{36}$ are each independently H, Cl, Br, F, or lower alkyl;
or a pharmaceutically acceptable salt thereof.

41. The compound of claim 40 wherein $R^{16}$ is methyl, or a pharmaceutically acceptable salt thereof.

42. The compound of claim 40 wherein no more than one of $R^{34}$, $R^{35}$, and $R^{36}$ is Cl, Br, or F; or a pharmaceutically acceptable salt thereof.

43. The compound of claim 40 wherein $R^{34}$, $R^{35}$, and $R^{36}$ are each independently H, Cl, Br, F, methyl, or ethyl; or a pharmaceutically acceptable salt thereof.

44. A compound represented by the Formula:

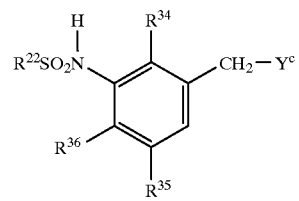

wherein:
$Y^c$ is 2-imidazoline or 4-imidazole;
$R^{22}$ is lower alkyl;
$R^{34}$, $R^{35}$, and $R^{36}$ are each independently H, Cl, Br, F, or lower alkyl;
or a pharmaceutically acceptable salt thereof.

45. The compound of claim 44 wherein $R^{22}$ is methyl, or a pharmaceutically acceptable salt thereof.

46. The compound of claim 44 wherein no more than one of $R^{34}$, $R^{35}$, and $R^{36}$ is Cl, Br, or F; or a pharmaceutically acceptable salt thereof.

47. The compound of claim 44 wherein $R^{34}$, $R^{35}$, and $R^{36}$ are each independently H, Cl, Br, F, methyl, or ethyl; or a pharmaceutically acceptable salt thereof.

48. A compound represented by the Formula:

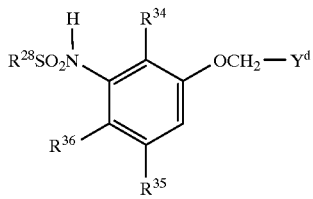

wherein:

$Y^d$ is 2-imidazoline or 4-imidazole;

$R^{28}$ is lower alkyl;

$R^{34}$, $R^{35}$, and $R^{36}$ are each independently H, Cl, Br, F, or lower alkyl;

or a pharmaceutically acceptable salt thereof.

49. The compound of claim 45 wherein $R^{28}$ is methyl, or a pharmaceutically acceptable salt thereof.

50. The compound of claim 48 wherein no more than one of $R^{34}$, $R^{35}$, and $R^{36}$ is Cl, Br, or F; or a pharmaceutically acceptable salt thereof.

51. The compound of claim 48 wherein $R^{34}$, $R^{35}$, and $R^{36}$ are each independently H, Cl, Br, F, methyl, or ethyl; or a pharmaceutically acceptable salt thereof.

52. A compound of the Formula,

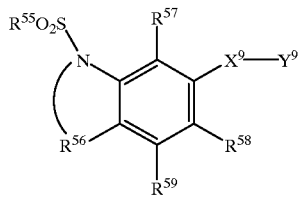

wherein:

$X^g$ is —NH—, —CH$_2$—, or —OCH$_2$—;

$Y^g$ is 2-imidazoline or 4-imidazole;

$R^{55}$ is lower alkyl or phenyl;

$R^{56}$ forms part of an unsubstituted or optionally substituted 5- or 6-membered ring, wherein the optional substituents on the ring aro halo, lower alkyl, or —CN and $R^{56}$ is (CH$_2$)$_k$ wherein k is 1 or 2, CH=CH, CH=CHCH$_2$, or CH$_2$CH=CH;

$R^{57}$, $R^{58}$, and $R^{59}$ are each independently hydrogen, lower alkyl, —CF$_3$, lower alkoxy, halogen, phenyl, lower alkenyl, hydroxyl, lower alkylsulfonamido, or lower cycloalkyl;

or a pharmaceutically acceptable salt thereof.

53. The compound of claim 52 wherein $R^{56}$ is CH=CH, $R^{57}$, $R^{58}$ and $R^{59}$ are H, and $Y^g$ is imidazolidine; or a pharmaceutically acceptable salt thereof.

54. A compound of the Formula:

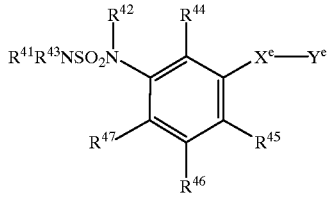

wherein:

$X^e$ is —NH—, —CH$_2$—, or —OCH$_2$—, $Y^e$ is 2-imidazoline or 4-imidazole;

$R^{41}$, $R^{42}$, and $R^{43}$ are each independently H, phenyl, or lower alkyl;

$R^{44}$, $R^{45}$, $R^{46}$, and $R^{47}$ are each independently hydrogen, lower alkyl, —CF$_3$, lower alkoxy, halogen, phenyl, lower alkenyl, hydroxyl, lower alkylsulfonamido, or lower cycloalkyl, wherein $R^{42}$ and $R^{47}$ optionally may be taken together to form alkylene or alkenylene of 2 to 3 carbon atoms in a 5- or 6-membered ring;

or a pharmaceutically acceptable salt thereof.

55. The compound of claim 54 wherein $X^e$ is OCH$_2$, $Y^e$ is 2-imidazoline, $R^{41}$ and $R^{43}$ are CH$_3$, and $R^{42}$, $R^{44}$, $R^{45}$, $R^{46}$, and $R^{47}$ are H; or a pharmaceutically acceptable salt thereof.

56. A composition suitable for administration to a mammal having a disease state that is alloviated by treatment with an alpha$_{1A/1L}$-adrenoceptor agonist, which composition comprises a therapeutically effective amount of a compound of the Formula:

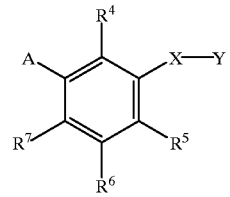

wherein:

A is $R^1_q(R^3R^{60}N)_m(Z)(NR^2)_n$;

m and q are each 0 or 1, with the proviso that when q is 1, m is 0 and when q is 0, m is 1;

z is C=O or SO$_2$;

n is 1 with the proviso that, when Z is C=O, m is 1;

X is —NH—, —CH$_2$—, or —OCH$_2$—;

Y is 2-imidazoline or 4-imidazole;

$R^1$ is H, lower alkyl, or phenyl, with the proviso that, when $R^1$ is H, m is 1;

$R^2$, $R^3$, and $R^{60}$ are each independently H, lower alkyl, or phenyl;

$R^4$, $R^5$, $R^6$, and $R^7$ are each independently hydrogen, lower alkyl, —CF$_3$, lower alkoxy, halogen, phenyl, lower alkenyl, hydroxyl, lower alkylsulfonamido, or lower cycloalkyl, wherein $R^2$ and $R^7$ optionally may be taken together to form alkylene or alkenylene of 2 to 3 carbon atoms in an unsubstituted or optionally substituted 5- or 6-membered ring, wherein the optional substituents on the ring are halo, lower alkyl, or —CN, with the proviso that, when $R^7$ is hydroxyl or lower alkylsulfonamido, then X is not —NH— when Y is 2-imidazoline;

or a pharmaceutically acceptable salt thereof.

57. The composition of claim 56 wherein A is (R$^1$SO$_2$NR$^2$—), (R$^3$R$^{60}$NSO$_2$NR$^2$—), or (R$^3$R$^{60}$NCONR$^2$—); or a pharmaceutically acceptable salt thereof.

58. A composition suitable for administration to a mammal having a disease state that is alleviated by treatment with an alpha$_{1A/1L}$-adrenoceptor agonist, which composition comprises a therapeutically effective amount of a compound of the Formula:

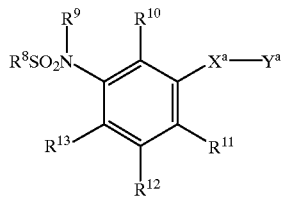

wherein:

$X^a$ is —NH—, —CH$_2$—, or —OCH$_2$—;

$Y^a$ is 2-imidazoline or 4-imidazole:

$R^8$ is lower alkyl, phenyl, or —NR$^{14}$R$^{15}$;

$R^9$, $R^{14}$, and $R^{15}$ are each independently H or lower alkyl;

$R^{10}$, $R^{11}$, $R^{12}$, and $R^{13}$ are each independently hydrogen, lower alkyl, —CF$_3$, lower alkoxy, halogen, phenyl, lower alkenyl, hydroxyl, lower alkylsulfonamido, or lower cycloalkyl, wherein $R^9$ and $R^{13}$ optionally may be taken together to form alkylene or alkenylene of 2 to 3 carbon atoms in a 5- or 6-membered ring, with the proviso that, when $R^7$ is hydroxyl or lower alkylsulfonamido, then X is not —NH— when Y is 2-imidazoline;

or a pharmaceutically acceptable salt thereof.

59. A composition suitable for administration to a mammal having a disease state that is alleviated by treatment with an alpha$_{1A/1L}$-adrenoceptor agonist, which composition comprises a therapeutically effective amount of a compound of the Formula:

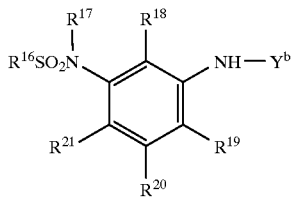

wherein:

$Y^b$ is 2-imidazoline;

$R^{16}$ is lower alkyl;

$R^{17}$ is H or lower alkyl;

$R^{18}$, $R^{19}$, $R^{20}$, and $R^{21}$ are each independently hydrogen, lower alkyl, —CF$_3$, lower alkoxy, or halogen;

or a pharmaceutically acceptable salt thereof.

60. A composition suitable for administration to a mammal having a disease state that is alleviated by treatment with an alpha$_{1A/1L}$-adrenoceptor agonist, which composition comprises a therapeutically effective amount of a compound of the Formula:

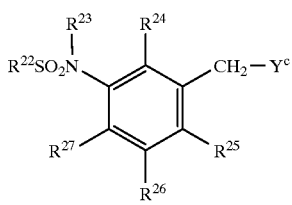

wherein:

$Y^c$ is 2-imidazoline or 4-imidazole;

$R^{22}$ is lower alkyl;

$R^{23}$ is H or lower alkyl;

$R^{24}$, $R^{25}$, $R^{26}$, and $R^{27}$ are each independently hydrogen, lower alkyl, lower alkoxy, halogen, phenyl, lower alkenyl, hydroxyl, or lower alkylsulfonamido;

or a pharmaceutically acceptable salt thereof.

61. A composition suitable for administration to a mammal having a disease state that is alleviated by treatment with an alpha$_{1A/1L}$-adrenoceptor agonist, which composition comprises a therapeutically effective amount of a compound of the Formula:

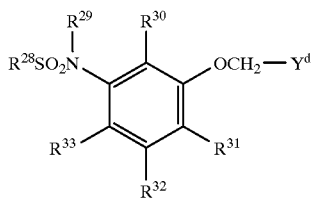

wherein:

$Y^d$ is 2-imidazoline or 4-imidazole;

$R^{28}$ is lower alkyl, or phenyl;

$R^{29}$, $R^{30}$, $R^{31}$, $R^{32}$, and $R^{33}$ are each independently hydrogen, lower alkyl, halogen, hydroxyl, or lower cycloalkyl;

or a pharmaceutically acceptable salt thereof.

62. The composition of claim 61 wherein $Y^d$ is 2-imidazoline, $R^{28}$ is methyl, $R^{30}$ is methyl, and $R^{33}$ is halogen; or a pharmaceutically acceptable salt thereof.

63. A composition suitable for administration to a mammal having a disease state that is alleviated by treatment with an alpha$_{1A/1L}$-adrenoceptor agonist, which composition comprises a therapeutically effective amount of a compound of the Formula:

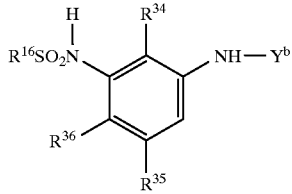

wherein:

$Y^b$ is 2-imidazoline;

$R^{16}$ is lower alkyl;

$R^{34}$, $R^{35}$, and $R^{36}$ are each independently H, Cl, Br, F, or lower alkyl;

or a pharmaceutically acceptable salt thereof.

64. A composition suitable for administration to a mammal having a disease state that is alleviated by treatment with an alpha$^{1A/1L}$-adrenoceptor agonist, which composition comprises a therapeutically effective amount of a compound of the Formula:

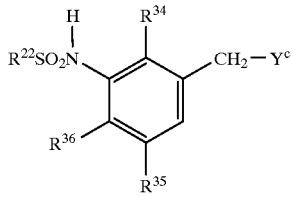

wherein:

$Y^c$ is 2-imidazoline or 4-imidazole;

$R^{22}$ is lower alkyl;

$R^{34}$, $R^{35}$, and $R^{36}$ are each independently H, Cl, Br, F, or lower alkyl;

or a pharmaceutically acceptable salt thereof.

65. A composition suitable for administration to a mammal having a disease state that is alleviated by treatment with an alpha$_{1A/1L}$-adrenoceptor agonist, which composition comprises a therapeutically effective amount of a compound of the Formula:

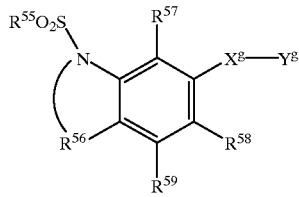

wherein:

$X^g$ is —NH—, —CH$_2$—, or —OCH$_2$—;

$Y^g$ is 2-imidazoline or 4-imidazole;

$R^{55}$ is lower alkyl or phenyl;

$R^{56}$ forms part of an unsubstituted or optionally substituted 5- or 6-membered ring, wherein the optional substituents on the ring are halo, lower alkyl, or —CN and $R^{56}$ is (CH$_2$)$_k$ wherein k is 1 or 2, CH═CH, CH═CHCH$_2$, or CH$_2$CH═CH;

$R^{57}$, $R^{58}$, and $R^{59}$ are each independently hydrogen, lower alkyl, —CF$_3$, lower alkoxy, halogen, phenyl, lower alkenyl, hydroxyl, lower alkylsulfonamido, or lower cycloalkyl;

or a pharmaceutically acceptable salt thereof.

66. A composition suitable for administration to a mammal having a disease state that is alleviated by treatment with an alpha$_{1A/1L}$-adrenoceptor agonist, which composition comprises a therapeutically effective amount of a compound of the Formula:

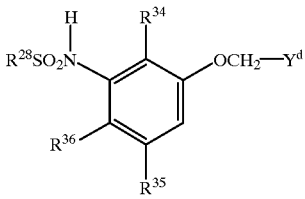

wherein:

$Y^d$ is 2-imidazoline or 4-imidazole;

$R^{28}$ is lower alkyl;

$R^{34}$, $R^{35}$, and $R^{36}$ are each independently H, Cl, Br, F, or lower alkyl;

or a pharmaceutically acceptable salt thereof.

67. A composition suitable for administration to a mammal having a disease state that is alleviated by treatment with an alpha$_{1A/1L}$-adrenoceptor agonist, which composition comprises a therapeutically effective amount of a compound of the Formula:

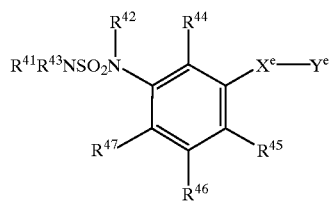

wherein:

$X^e$ is —NH—, —CH$_2$—, or —OCH$_2$—;

$Y^e$ is 2-imidazoline or 4-imidazole;

$R^{41}$, $R^{42}$, and $R^{43}$ are each independently H, phenyl, or lower alkyl, $R^{44}$, $R^{45}$, $R^{46}$, and $R^{47}$ are each independently hydrogen, lower alkyl, —CF$_3$, lower alkoxy, halogen, phenyl, lower alkenyl, hydroxyl, lower alkylsulfonamido, or lower cycloalkyl, wherein $R^{42}$ and $R^{47}$ optionally may be taken together to form alkylene or alkenylene of 2 to 3 carbon atoms in a 5- or 6-membered ring;

or a pharmaceutically acceptable salt thereof.

68. A method for treating a mammal having a disease state that is alleviated by treatment with an alpha$_{1A/1L}$-adrenoceptor agonist, which comprises administering a therapeutically effective amount of a compound of the Formula:

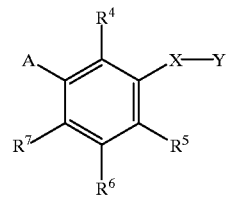

wherein:

A is $R^1{}_q(R^3R^{60}N)_m(Z)(NR^2)_m$;

m and q are each 0 or 1, with the proviso that when q is 1, m is 0 and when q is 0, m is 1;

Z is C═O or SO$_2$;

n is 1 with the proviso that, when Z is C=O, m is 1;

X is —NH—, —CH$_2$—, or —OCH$_2$—;

Y is 2-imidazoline or 4-imidazole;

R$^1$ is H, lower alkyl, or phenyl, with the proviso that, when R$^1$ is H, m is 1;

R$^2$, R$^3$, R$^{60}$ are each independently H, lower alkyl, or phenyl;

R$^4$, R$^5$, R$^6$, and R$^7$ are each independently hydrogen, lower alkyl, —CF$_3$, lower alkoxy, halogen, phenyl, lower alkenyl, hydroxyl, lower alkylsulfonamido, or lower cycloalkyl, wherein R$^2$ and R$^7$ optionally may be taken together to form alkylene or alkenylene of 2 to 3 carbon atoms in an unsubstituted or optionally substituted 5- or 6-membered ring, wherein the optional substituents on the ring are halo, lower alkyl, or —CN, with the proviso that, when R$^7$ is hydroxyl or lower alkylsulfonamido, then X is not —NH— when Y is 2-imidazoline;

or a pharmaceutically acceptable salt thereof.

69. The method of claim 68 wherein A is (R$^1$SO$_2$NR$^2$—), (R$^3$R$^{60}$NSO$_2$NR$^2$—), or (R$^3$R$^{60}$NCONR$^2$—); or a pharmaceutically acceptable salt thereof.

70. A method for treating a mammal having a disease state that is alleviated by treatment with an alpha$_{1A/1L}$-adrenoceptor agonist, which comprises administering a therapeutically effective amount of a compound of the Formula:

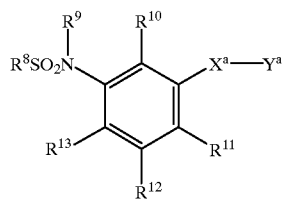

wherein:

X$^a$ is —NH—, —CH$_2$—, or —OCH$_2$—;

Y$^a$ is 2-imidazoline or 4-imidazole;

R$^8$ is lower alkyl, phenyl, or —NR$^{14}$R$^{15}$;

R$^9$, R$^{14}$ and R$^{15}$ are each independently H or lower alkyl;

R$^{10}$, R$^{11}$, R$^{12}$, and R$^{13}$ are each independently hydrogen, lower alkyl, —CF$_3$, lower alkoxy, halogen, phenyl, lower alkenyl, hydroxyl, lower alkylsulfonamido, or lower cycloalkyl, wherein R$^9$ and R$^{13}$ optionally may be taken together to form alkylene or alkenylene of 2 to 3 carbon atoms in a 5- or 6-membered ring, with the proviso that, when R$^7$ is hydroxyl or lower alkylsulfonamido, then X is not —NH— when Y is 2-imidazoline;

or a pharmaceutically acceptable salt thereof.

71. A method for treating a mammal having a disease state that is alleviated by treatment with an alpha$_{1A/1L}$-adrenoceptor agonist, which comprises administering a therapeutically effective amount of a compound of the Formula:

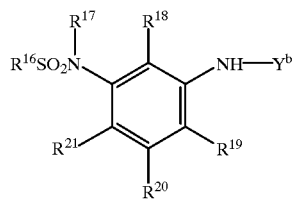

wherein:

Y$^b$ is 2-imidazoline;

R$^{16}$ is lower alkyl;

R$^{17}$ is H or lower alkyl;

R$^{18}$, R$^{19}$, R$^{20}$, and R$^{21}$ are each independently hydrogen, lower alkyl, —CF$_3$, lower alkoxy, or halogen;

or a pharmaceutically acceptable salt thereof.

72. A method for treating a mammal having a disease state that is alleviated by treatment with an alpha$^{1A/1L}$-adrenoceptor agonist, which comprises administering a therapeutically effective amount of a compound of the Formula:

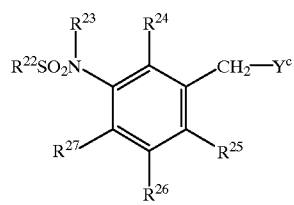

wherein:

Y$^c$ is 2-imidazoline or 4-imidazole;

R$^{22}$ is lower alkyl;

R$^{23}$ is H or lower alkyl;

R$^{24}$, R$^{25}$, R$^{26}$, and R$^{27}$ are each independently hydrogen, lower alkyl, lower alkoxy, halogen, phenyl, lower alkenyl, hydroxyl, or lower alkylsulfonamido;

or a pharmaceutically acceptable salt thereof.

73. A method for treating a mammal having a disease state that is alleviated by treatment with an alpha$_{1A/1L}$-adrenoceptor agonist, which comprises administering a therapeutically effective amount of a compound of the Formula:

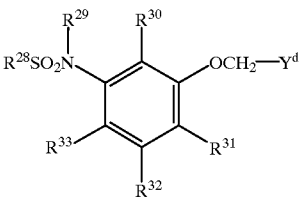

wherein:

Y$^d$ is 2-imidazoline or 4-imidazole;

R$^{28}$ is lower alkyl or phenyl;

R$^{29}$, R$^{30}$, R$^{31}$, R$^{32}$, and R$^{33}$ are each independently hydrogen, lower alkyl, halogen, hydroxyl, or lower cycloalkyl;

or a a pharmaceutically salt thereof.

74. The method of claim 73 wherein Y$^d$ is 2-imidazoline, R$^{28}$ is methyl, R$^{30}$ is methyl, and R$^{33}$ is halogen; or a pharmaceutically acceptable salt thereof.

75. A method for treating a mammal having a disease state that is alleviated by treatment with an alpha$_{1A/1L}$-adrenoceptor agonist, which comprises administering a therapeutically effective amount of a compound of the Formula:

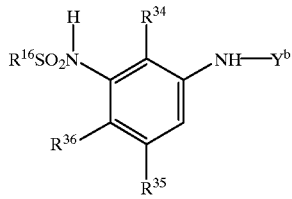

wherein:

$Y^b$ is 2-imidazoline;

$R^{16}$ is lower alkyl;

$R^{34}$, $R^{35}$, and $R^{36}$ are each independently H, Cl, Br, F, or lower alkyl;

or a pharmaceutically acceptable salt thereof.

76. A method for treating a mammal having a disease state that is alleviated by treatment with an alpha$_{1A/1L}$-adrenoceptor agonist, which comprises administering a therapeutically effective amount of a compound of the Formula:

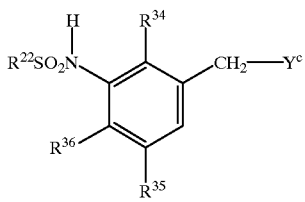

wherein:

$Y^c$ is 2-imidazoline or 4-imidazole;

$R^{22}$ is lower alkyl;

$R^{34}$, $R^{35}$, and $R^{36}$ are each independently H, Cl, Br, F, or lower alkyl;

or a pharmaceutically acceptable salt thereof.

77. A method for treating a mammal having a disease state that is alleviated by treatment with an alpha$_{1A/1L}$-adrenoceptor agonist, which comprises administering a therapeutically effective amount of a compound of the Formula:

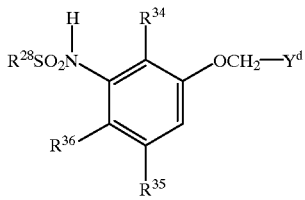

wherein:

$Y^d$ is 2-imidazoline or 4-imidazole;

$R^{28}$ is lower alkyl;

$R^{34}$, $R^{35}$, and $R^{36}$ are each independently H, Cl, Br, F, or lower alkyl;

or a pharmaceutically acceptable salt thereof.

78. A method for treating a mammal having a disease state that is alleviated by treatment with an alpha$_{1A/1L}$-adrenoceptor agonist, which comprises administering a therapeutically effective amount of a compound of the Formula:

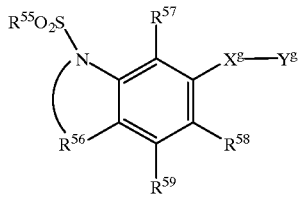

wherein:

$X^g$ is —NH—, —CH$_2$—, or —OCH$_2$—;

$Y^g$ is 2-imidazoline or 4-imidazolo;

$R^{55}$ is lower alkyl or phenyl;

$R^{56}$ forms part of an unsubstituted or optionally substituted 5- or 6-membered ring, wherein the optional substituents on the ring are halo, lower alkyl, or —CN and $R^{56}$ is (CH$_2$)$_k$ wherein k is 1 or 2, CH=CH, CH=CHCH$_2$, or CH$_2$CH=CH;

$R^{57}$, $R^{58}$, and $R^{59}$ are each independently hydrogen, lower alkyl —CF$_3$, lower alkoxy, halogen, phenyl, lower alkenyl, hydroxyl, lower alkylsulfonamido, or lower cycloalkyl;

or a pharmaceutically acceptable salt thereof.

79. A method for treating a mammal having a disease state that is alleviated by treatment with an alpha$_{1A/1L}$-adrenoceptor agonist, which comprises administering a therapeutically effective amount of a compound of the Formula:

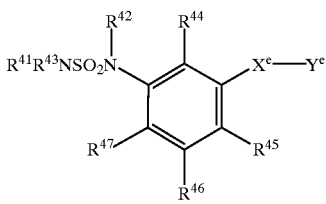

wherein:

$X^e$ is —NH—, —CH$_2$—, or —OCH$_2$—;

$Y^e$ is 2-imidazoline or 4-imidazole;

$R^{41}$, $R^{42}$, and $R^{43}$ are each independently H, phenyl, or lower alkyl;

$R^{44}$ $R^{45}$, $R^{46}$, and $R^{47}$ are each independently hydrogen, lower alkyl, —CF$_3$, lower alkoxy, halogen, phenyl, lower alkenyl, hydroxyl, lower alkylsulfonamido, or lower cycloalkyl, wherein $R^{42}$ and $R^{47}$ optionally may be taken together to form alkylene or alkenylene of 2 to 3 carbon atoms in a 5- or 6-membered ring;

or a pharmaceutically acceptable salt thereof.

80. A method for treating a mammal having urinary incontinence, which comprises administering a therapeutically effective amount of a compound of the Formula:

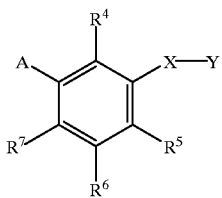

wherein:

A is $R^1_q(R^3R^{60}N)_m(Z)(NR^2)_n$;

m and q are each 0 or 1, with the proviso that when q is 1, m is 0 and when q is 0, m is 1;

Z is C=O or $SO_2$;

n is 1 with the proviso that, when Z is C=O, m is 1;

X is —NH—, —$CH_2$—, or —$OCH_2$—;

Y is 2-imidazoline or 4-imidazole;

$R^1$ is H, lower alkyl, or phenyl with the proviso that, when $R^1$ is H, m is 1;

$R^2$, $R^3$, and $R^{60}$ are each independently H or lower alkyl;

$R^4$, $R^5$, $R^6$, and $R^7$ are each independently hydrogen, lower alkyl, —CF, lower alkoxy, halogen, phenyl, lower alkenyl, hydroxyl, lower alkylsulfonamido, or lower cycloalkyl, wherein $R^2$ and $R^7$ optionally may be taken together to form alkylene or alkenylene of 2 to 3 carbon atoms in an unsubstituted or optionally substituted 5- or 6-membered ring, wherein the optional substituents on the ring are halo, lower alkyl, or —CN, with the proviso that, when $R^7$ is hydroxyl or lower alkylsulfonamido, then X is not —NH— when Y is 2-imidazoline:

or a pharmaceutically acceptable salt thereof.

81. The method of claim 80 wherein A is ($R^1SO_2NR^2$—), ($R^3R^{60}NSO_2NR^2$—), or ($R^3R^{60}NCONR^2$—); or a pharmaceutically acceptable salt thereof.

82. The method of claim 70, 71, 72, 73, 74, 75, 76, 77, 78, or 79 wherein the disease state is urinary incontinence.

83. The method of claim 70, 71, 72, 73, 74, 75, 76, 77, 78, or 79 wherein the disease state is nasal congestion.

84. The method of claim 70 wherein the disease state is selected from the group consisting of priapism, depression, anxiety, dementia, senility, Alzheimer's, deficiencies in attentiveness and cognition, and eating disorders.

85. The method of claim 84 wherein the eating disorders are obesity, bulimia, or anorexia.

* * * * *

UNITED STATES PATENT AND TRADEMARK OFFICE
CERTIFICATE OF CORRECTION

PATENT NO: 5,952,362

DATED: September 14, 1999

INVENTOR(S): Cournoyer et al.

It is certified that error appears in the above-identified patent and that said Letters Patent is hereby corrected as shown below:

In the Abstract, front page, lines 8-9, delete ", with the proviso that, when $R^1$ is H, m is 1".

Column 7, lines 63-64; delete ", with the proviso that, when $R^1$ is H, m is 1".

Column 39, lines 54-55, delete the incorrect chemical name "(N-[3-(3H-imidazol-4-ylmethyl)-2-methyl-phenyl]-methanesulfonamide)" and insert therefor the correct chemical name -- (N-[3-(4,5-dihydro-1H-imidazol-2-ylmethyl)-2-vinyl-phenyl]-methanesulfonamide) --.

Claim 1, column 125, lines 2-3; delete ", with the proviso that, when $R^1$ is H, m is 1".

Claim 56, column 130, lines 43-44, delete ", with the proviso that, when $R^1$ is H, m is 1".

Claim 68, column 135, lines 5-6, delete ", with the proviso that, when $R^1$ is H, m is 1".

Claim 80, column 139, lines 21-22, delete "with the proviso that, when $R^1$ is H, m is 1".

Signed and Sealed this

Seventeenth Day of October, 2000

*Attest:*

Q. TODD DICKINSON

*Attesting Officer*         *Director of Patents and Trademarks*